(12) United States Patent
White et al.

(10) Patent No.: US 10,400,043 B2
(45) Date of Patent: Sep. 3, 2019

(54) TREATMENT OF DIFFUSE LARGE-CELL LYMPHOMA WITH ANTI-CD20 ANTIBODY

(71) Applicant: Biogen Inc., Cambridge, MA (US)

(72) Inventors: Christine A. White, Rancho Santa Fe, CA (US); Antonio J. Grillo-Lopez, Rancho Santa Fe, CA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 15/856,922

(22) Filed: Dec. 28, 2017

(65) Prior Publication Data

US 2018/0118844 A1    May 3, 2018

Related U.S. Application Data

(60) Continuation of application No. 15/334,234, filed on Oct. 25, 2016, now abandoned, which is a continuation of application No. 14/310,167, filed on Jun. 20, 2014, now Pat. No. 9,504,744, which is a continuation of application No. 14/045,375, filed on Oct. 3, 2013, now Pat. No. 8,821,873, which is a division of application No. 09/628,187, filed on Jul. 28, 2000, now Pat. No. 8,557,244.

(60) Provisional application No. 60/148,286, filed on Aug. 11, 1999.

(51) Int. Cl.
| | | |
|---|---|---|
| A61K 39/395 | (2006.01) | |
| A61K 31/573 | (2006.01) | |
| A61K 31/704 | (2006.01) | |
| A61K 31/664 | (2006.01) | |
| C07K 16/28 | (2006.01) | |
| A61K 31/475 | (2006.01) | |
| A61K 31/675 | (2006.01) | |
| A61K 35/28 | (2015.01) | |
| A61K 35/545 | (2015.01) | |
| A61K 39/00 | (2006.01) | |

(52) U.S. Cl.
CPC ........ *C07K 16/2887* (2013.01); *A61K 31/475* (2013.01); *A61K 31/573* (2013.01); *A61K 31/664* (2013.01); *A61K 31/675* (2013.01); *A61K 31/704* (2013.01); *A61K 35/28* (2013.01); *A61K 35/545* (2013.01); *A61K 39/3955* (2013.01); *A61K 39/39558* (2013.01); *A61K 2039/505* (2013.01); *C07K 2317/24* (2013.01); *Y10S 424/801* (2013.01)

(58) Field of Classification Search
CPC ............ A61K 39/39558; A61K 39/395; A61K 31/573; A61K 31/704; A61K 31/664
USPC ................ 424/144.1, 130.1, 133.1
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,831,175 A | 5/1989 | Gansow et al. |
| 4,975,278 A | 12/1990 | Senter et al. |
| 5,099,069 A | 3/1992 | Gansow et al. |
| 5,124,471 A | 6/1992 | Gansow et al. |
| 5,145,677 A | 9/1992 | von Eichborn et al. |
| 5,165,922 A | 11/1992 | Hellstrom et al. |
| 5,225,535 A | 7/1993 | DeFreitas et al. |
| 5,225,539 A | 7/1993 | Winter |
| 5,246,692 A | 9/1993 | Gansow et al. |
| 5,250,732 A | 10/1993 | Kogan et al. |
| 5,286,850 A | 2/1994 | Gansoh et al. |
| 5,439,665 A | 8/1995 | Hansen et al. |
| 5,460,785 A | 10/1995 | Rhodes et al. |
| 5,500,362 A | 3/1996 | Robinson et al. |
| 5,530,101 A | 6/1996 | Queen et al. |
| 5,595,721 A | 1/1997 | Kaminski et al. |
| 5,633,425 A | 5/1997 | Lonberg et al. |
| 5,648,267 A | 7/1997 | Reff |
| 5,677,171 A | 10/1997 | Hudziak et al. |
| 5,677,180 A | 10/1997 | Robinson et al. |
| 5,686,072 A | 11/1997 | Uhr et al. |
| 5,691,135 A | 11/1997 | Braun et al. |
| 5,691,320 A | 11/1997 | von Borstel et al. |
| 5,693,780 A | 12/1997 | Newman et al. |
| 5,721,108 A | 2/1998 | Robinson et al. |
| 5,726,023 A | 3/1998 | Cheever et al. |
| 5,736,137 A | 4/1998 | Anderson et al. |
| 5,776,456 A | 7/1998 | Anderson et al. |
| 5,843,398 A | 12/1998 | Kaminiski et al. |
| 5,843,439 A | 12/1998 | Anderson et al. |

(Continued)

FOREIGN PATENT DOCUMENTS

| | | |
|---|---|---|
| AU | 56032/94 | 11/1993 |
| CA | 2461714 | 9/2002 |

(Continued)

OTHER PUBLICATIONS

Hill et al. (Blood, vol. 88, No. 3, Aug. 1, 1996, pp. 1046-1051).*

(Continued)

*Primary Examiner* — Yan Xiao

(74) *Attorney, Agent, or Firm* — Wendy M. Lee

(57) ABSTRACT

The present invention concerns methods for the treatment of diffuse large cell lymphoma by administration of an anti-CD20 antibody and chemotherapy. Particular embodiments include the administration of anti-CD20 antibody in combination with chemotherapy comprising CHOP (cyclophosphamide, hydroxydaunorubicin/doxorubicin, vincristine, and prednisone/prednisolone) and/or in combination with a transplantation regimen.

1 Claim, No Drawings

(56) References Cited

U.S. PATENT DOCUMENTS

| | | |
|---|---|---|
| 6,015,542 A | 1/2000 | Kaminiski et al. |
| 6,090,365 A | 7/2000 | Kaminiski et al. |
| 6,111,166 A | 8/2000 | van de Winkel |
| 6,120,767 A | 9/2000 | Robinson et al. |
| 6,183,744 B1 | 2/2001 | Goldenberg |
| 6,287,537 B1 | 9/2001 | Kaminiski et al. |
| 6,306,393 B1 | 10/2001 | Goldenberg |
| 6,399,061 B1 | 6/2002 | Anderson et al. |
| 6,399,649 B1 | 6/2002 | Anderson et al. |
| 6,455,043 B1 | 9/2002 | Grillo-Lopez |
| RE38,088 E | 4/2003 | Larka et al. |
| 6,565,827 B1 | 5/2003 | Kaminiski et al. |
| 6,652,852 B1 | 11/2003 | Robinson et al. |
| 6,682,734 B1 | 7/2004 | Anderson et al. |
| 6,893,625 B1 | 5/2005 | Robinson et al. |
| 7,381,560 B2 | 6/2008 | Anderson et al. |
| 7,422,739 B2 | 9/2008 | Anderson et al. |
| 7,682,612 B1 | 3/2010 | White et al. |
| 7,744,877 B2 | 6/2010 | Anderson et al. |
| 8,206,711 B2 | 6/2012 | White et al. |
| 8,329,172 B2 | 11/2012 | Grillo-Lopez |
| 8,557,244 B1 | 10/2013 | White et al. |
| 8,821,873 B2 | 9/2014 | White et al. |
| 9,296,821 B2 | 3/2016 | Grillo-Lopez |
| 9,504,744 B2 | 11/2016 | White et al. |
| 10,113,000 B2 | 10/2018 | Grillo-López |
| 2002/0009444 A1 | 1/2002 | Grillo-Lopez |
| 2002/0197255 A1 | 12/2002 | Anderson et al. |
| 2003/0018014 A1 | 1/2003 | Lerner |
| 2003/0021781 A1 | 1/2003 | Anderson et al. |
| 2003/0026804 A1 | 2/2003 | Grillo-Lopez |
| 2003/0082172 A1 | 5/2003 | Anderson et al. |
| 2003/0095963 A1 | 5/2003 | Anderson et al. |
| 2003/0147885 A1 | 8/2003 | Anderson et al. |
| 2003/0206903 A1 | 11/2003 | Grillo-Lopez |
| 2004/0167319 A1 | 8/2004 | Teeling et al. |
| 2004/0213784 A1 | 10/2004 | Grillo-Lopez et al. |
| 2005/0163708 A1 | 7/2005 | Robinson et al. |
| 2005/0186205 A1 | 8/2005 | Anderson et al. |
| 2006/0034835 A1 | 2/2006 | Adams et al. |
| 2008/0038261 A1 | 2/2008 | Grillo-Lopez |
| 2009/0074760 A1 | 3/2009 | Grillo-Lopez et al. |
| 2010/0080769 A1 | 4/2010 | Grillo-Lopez et al. |
| 2011/0165159 A1 | 7/2011 | Grillo-Lopez et al. |
| 2012/0251534 A1 | 10/2012 | Grillo-Lopez |
| 2012/0251535 A1 | 10/2012 | Grillo-Lopez |
| 2012/0258101 A1 | 10/2012 | Grillo-Lopez |
| 2012/0258102 A1 | 10/2012 | Grillo-Lopez |
| 2013/0273039 A1 | 10/2013 | Grillo-Lopez |
| 2013/0273041 A1 | 10/2013 | Grillo-Lopez et al. |
| 2014/0030263 A1 | 1/2014 | White et al. |
| 2014/0056887 A1 | 2/2014 | Grillo-Lopez |
| 2014/0302018 A1 | 10/2014 | White et al. |
| 2014/0363424 A1 | 12/2014 | Grillo-Lopez et al. |
| 2015/0183882 A1 | 7/2015 | Grillo-Lopez |
| 2016/0333106 A1 | 11/2016 | Grillo-Lopez |
| 2017/0037139 A1 | 2/2017 | White et al. |
| 2017/0037140 A1 | 2/2017 | Grillo-Lopez |

FOREIGN PATENT DOCUMENTS

| | | |
|---|---|---|
| EP | 0 125 023 A1 | 11/1984 |
| EP | 0 173 494 A2 | 3/1986 |
| EP | 0 274 394 A2 | 7/1988 |
| EP | 0 274 394 A3 | 1/1990 |
| EP | 0 125 023 B1 | 6/1991 |
| EP | 0 510 949 A2 | 10/1992 |
| EP | 0 682 040 A1 | 11/1995 |
| EP | 0 451 216 B1 | 1/1996 |
| EP | 0 669 836 B1 | 7/1996 |
| EP | 0 752 248 A1 | 1/1997 |
| EP | 0 682 040 B1 | 8/1999 |
| EP | 0 125 023 B2 | 3/2002 |
| EP | 1 974 747 B1 | 10/2008 |
| EP | 2000149 B1 | 5/2009 |
| JP | 5-508630 | 6/2014 |
| MX | PA01001530 A | 4/2002 |
| WO | WO 1987/002671 A1 | 5/1987 |
| WO | WO 1988/004936 A1 | 7/1988 |
| WO | WO 1989/000999 A1 | 2/1989 |
| WO | WO 1991/004320 A1 | 4/1991 |
| WO | WO 1991/017770 | 11/1991 |
| WO | WO 1992/007466 A1 | 5/1992 |
| WO | WO 1993/002108 A1 | 2/1993 |
| WO | WO 1994/008601 | 4/1994 |
| WO | WO 1994/0011007 | 5/1994 |
| WO | WO 1994/011026 A2 | 5/1994 |
| WO | WO 1995/03770 | 2/1995 |
| WO | WO 1996/018413 | 6/1996 |
| WO | WO 1998/042378 | 10/1998 |
| WO | WO 2000/009160 A1 | 2/2000 |
| WO | WO 2000/027428 A1 | 5/2000 |
| WO | WO 2000/027433 A1 | 5/2000 |
| WO | WO 2000/0067796 | 11/2000 |
| WO | WO 2000/074718 | 12/2000 |
| WO | WO 2001/010460 A1 | 2/2001 |
| WO | WO 2004/056312 A2 | 7/2004 |

OTHER PUBLICATIONS

"EDGAR Database" page from Internet Archive, https://web.archive.org/web/19970415001755/http:/www.sec.gov:80/edgarhp.htm (1 pg) ( Jun. 29, 2018).

"General Information on the EDGAR Database" page from Internet Archive, https://web.archive.org/web/19970605114044/http:/www.sec.gov:80/edaux/general.htm (3 pgs) ( Jun. 29, 2018).

"Important Information About EDGAR" page from Internet Archive, https://web.archive.org/web/19970605114237/http:/www.sec.gov:80/edaux/wedgar.htm (1 pg) ( Jun. 29, 2018).

"Search the EDGAR database" page from the Internet Archive, https://web.archive.org/web/19970605112818/http:/www.sec.gov:80/edaux/searches.htm (2 pgs) (Jun. 29, 2018).

10-K/A .txt file from EDGAR system, https://www.sec.gov/Archives/edgar/data/875045/0000936392-98-000361.txt (81 pgs) ( Jun. 29, 2018).

Affidavit of Christopher Butler dated Jul. 3, 2018 (11 pgs), in IPR2017-01095 re: U.S. Pat. No. 9,296,821, Grillo-López, "Combination Therapies for B-cell Lymphomas Comprising Administration of Anti-CD20 Antibodies".

"Affidavit of Professor Henry Miles Prince AM" (Unsworn copy; Federal Court of Australia, F. Hoffmann-La Roche AG and another (Applicants); Sandoz Pty Ltd (Respondent); No NSD 2265 of 2017; 97 pages and 185 pages; Annexures MP-1; MP2 and MP-12 to MP-18 provided); (Apr. 2018).

Berczi et al. Immune Modulating Agents "Hormones as Immune Modulating Agents" Kresina, T., New York:Marcel Dekker, Inc..:75-120 ( 1998).

Bezwoda et al., "Long-term results of a multicentre randomised, comparative phase III trial of CHOP versus CNOP regimens in patients with intermediate- and high-grade non-Hodgkin's lymphomas" Eur J Cancer 31A(6):903-911 ( 1995).

Biogen, Inc.'s Response to Petitioner's Additional Discovery (32 pages), in IPR2016-01614 re: U.S. Pat. No. 7,820,161, dated Jul. 26, 2017.

Business of the Business: Concurrent Infusions J. Oncology Practice 4(4): 171 (2008), 1 pg.

Charles Marwick, "Monoclonal Antibody Therapy of Lymphoma" The Journal of the American Medical Association 278(8):616-618 (Aug. 27, 1997).

ClinicalTrials.gov, "Combination Chemotherapy With or Without Monoclonal Antibody Therapy in Treating Older Patients With Non-Hodgkin's Lymphoma" (ECOG 4494 rituximab phase 3; NCT00003150; First Posted Feb. 16, 2004; Last Update Posted Jun. 21, 2013; 7 pages), ( 2017) https://www.clinicaltrials.gov/ct2/show/NCT00003150?term=ECOG+4494&intr=rituximab&phase=2&rank=1.

ClinicalTrials.gov, "Combination Chemotherapy With or Without Monoclonal Antibody Therapy in Treating Patients With Stage III or Stage IV Low-Grade Non-Hodgkin's Lymphoma" (ECOG 1496

(56) References Cited

OTHER PUBLICATIONS rituximab; NCT00003204; First Posted Jan. 27, 2003; Last Update Posted Feb. 27, 2013; 9 pages), ( 2017) https://www.clinicaltrials.gov/ct2/show/NCT00003204?term=ECOG+1496&intr=rituximab&rank=1.
Coiffier et al., "A multicenter, randomized phase II study of rituximab (MABTHERA) at two dosages inpatients relapsed or refractory intermediate grade lymphoma or in elderly patients in first-line therapy" British Journal of Haematology (Abstract P-0950), 102(1):238 (Jul. 1998).
Coiffier et al., "Rituximab in diffuse large B cell and mantle cell lymphomas" Annals of Oncology (Abstract 020), 9( SUPPL 3):27 ( 1998).
Coiffier, B., "Mabthera in aggressive lymphoma: An update on its efficacy and toxicity" Annals of Oncology (Abstracts of Satellite Symposia, Hoffmann-La Roche, Mabthera: Future Applications in CD20+ malignancies), 10( SUPPL 3):213 (Jun. 1, 1999).
Coiffier, B., "Treatment of aggressive non-Hodgkin's lymphoma" Semin Oncol 26(5 SUPPL 14):12-20 (Oct. 1999).
Coiffier, "Treatment of Non-Follicular Indolent Disseminated Lymphomas" British Journal of Haematology 102(1):271 (Abstract Hif-1088) ( 1998).
Czuczman et al., "IDEC-C2B8/CHOP chemolmmunotherapy In patients with low-grade lymphoma: Interim clinical and bcl-2 (PCR) results" Ann. Oncol (Abstract 191), 7( SUPPL 1):1 ( 1996).
Czuczman et al., "Rituximab in Combination with CHOP or Fludarabine in Low-Grade Lymphoma" Seminars in Oncology 29(1 SUPPL 2):36-40 ( 2002).
Dallegri et al., "Defective antibody-dependent tumour cell lysis by neutrophils from cancer patients" Clin Exp Immunol 77(1):58-61 (Jul. 1989).
Decision on Institution (DI) of Inter Partes Review (Paper 10), IPR2018-00285 re: U.S. Pat. No. 8,329,172 B2 (Grillo-López, et al., "Combination therapies for B-cell lymphomas comprising administration of anti-CD20 antibody"), entered Jul. 9, 2018 (32 pages).
Decision on Institution (DI) of Inter Partes Review (Paper 15), in IPR2018-00186 re: U.S. Pat. No. 9,296,821 Grillo-López, et al., "Combination therapies for B-cell lymphomas comprising administration of anti-CD20 antibodies", entered Jun. 14, 2018 (22 pages).
Declaration of Alaina Bird, dated Nov. 13, 2018 (4 pages), in IPR2018-00285 re: U.S. Pat. No. 8,329,172 B2, Grillo-López, "Combination therapies for B-cell lymphomas comprising administration of anti-CD20 antibodies".
Declaration of Ann Simpson, dated Jun. 6, 2018 (3 pages) in IPR2017-01095 re: U.S. Pat. No. 9,296,821, Grillo-López, "Combination therapies for B-cell lymphomas comprising administration of anti-CD20 antibodies".
Declaration of Daniel J. Knauss, dated Jul. 5, 2018, in Support of Petitioner's Combined Reply in IPR2017-0195, re: U.S. Pat. No. 9,296,821, Grillo-López, "Combination therapies for B-Cell lymphomas comprising administration of anti-CD20 antibodies," (4 pgs).
Declaration of Dr. Andrew John Davies, dated Aug. 31, 2017, submitted in U.S. Appl. No. 15/225,594, now U.S. Pat. No. 10/113,000 B2, dated Oct. 30, 2018 (14 pages).
Declaration of Dr. Leslie Oleksowicz in Support of Patent Owner Response, dated Nov. 13, 2018 (83 pages) in IPR2018-00285 re: U.S. Pat. No. 8,329,172, Grillo-López, "Combination therapies for B-cell lymphomas comprising administration of anti-CD20 antibodies".
"Declaration of Megan Raymond in Support of Patent Owner's Response" (Pfizer, Inc. vs. Biogen, Inc.; Case IPR2018-00186; U.S. Pat. No. 9,296,821 B2, Grillo-López, Combination Therapies for B-Cell Lymphomas Comprising Administration of Anti-CD20 Antibodies; 5 pages), (Mar. 13, 2018).
Declaration of Robert J. Soiffer, dated Sep. 10, 2018 (115 pages), in IPR2018-00285 re: U.S. Pat. No. 8,329,172, Grillo-López, "Combination therapies for B-cell lymphomas comprising administration of anti-CD20 antibodies".
Declaration of Sayem Osman, dated Oct. 8, 2018 (13 pages) in IPR2018-00186 re: U.S. Pat. No. 9,296,821 B2, Grillo-López, et al., "Combination therapies for B-cell lymphomas comprising administration of anti-CD20 antibodies".
"Declaration of Sharon Song" (Pfizer, Inc. vs. Biogen, Inc.; Case IPR2018-00285; U.S. Pat. No. 8,329,172, Grillo-López, Combination Therapies for B-Cell Lymphomas Comprising Administration of Anti-CD20 Antibody; 4 pages), (Apr 11, 2018).
"Declaration of Sharon Song" (Pfizer, Inc. vs. Biogen, Inc; Case IPR2018-00231; U.S. Pat. No. 9,504,744, White et al., Treatment of Diffuse Large-Cell Lymphoma with Anti-CD20 Antibody; 3 pages), (Mar. 19, 2018).
Declaration of Sylvia Hall-Ellis, Ph.D., dated Jul. 5, 2018, in Support of Petitioner's Reply Re: Petition for Inter Partes Review of U.S. Pat. No. 9,296,821—IPR2017-01095 (94 pgs).
Definition of myelosuppression—NCI Dictionary of Cancer Terms—National Cancer Institute, 1 page (Retrieved on Mar. 19, 2018) https://www.cancer.gov/publications/dictionaries/cancer-terms/def/myelosuppression.
Deposition Transcript of Brad S. Kahl. M.D. (168 pages), in IPR2017-01168, re: U.S. Pat. No. 8,821,873 B2, White et al., "Treatment of diffuse large-cell lymphoma with anti-CD20 antibody" (Apr. 14, 2018)., pp. 1-168.
Deposition Transcript of Peter McLaughlin, (213 pages) in IPR2017-01095 re: U.S. Pat. No. 9,296,821, Grillo-López, "Combination therapies for B-cell lymphomas comprising administration of anti-CD20 antibodies" (Apr. 18, 2018).
Declaration of Robert J. Soiffer M.D., (74 pages) in Pfizer, Inc. v. Biogen., IPR2017-01168 re: U.S. Pat. No. 8,821,873 B2, White et al., "Treatment of diffuse large-cell lymphoma with anti-CD20 antibody" (May 24, 2018).
Deposition Transcript of Robert J. Soiffer M.D., (85 pages) in Pfizer, Inc. v. Biogen., IPR2017-01168 re: U.S. Pat. No. 8,821,873 B2, White et al., "Treatment of diffuse large-cell lymphoma with anti-CD20 antibody"(Jun. 15, 2018).
Deposition Transcript of Robert J. Soiffer, M.D., (105 pages) in IPR2018-00285, re: U.S. Pat. No. 8,329,172 B2, Grillo-lópez et al., "Combination therapies for B-cell lymphomas comprising administration of anti-CD20 antibody" (Oct. 23, 2018).
Deposition Transcript of Robert J. Soiffer, M.D., (232 pages) in IPR2017-01168 Re: U.S. Pat. No. 8,821,873 B2, White et al., "Treatment of diffuse large-cell lymphoma with anti-CD20 antibody" (Jun. 15, 2018).
Deposition Transcript of Robert J. Soiffer, M.D., (76 pages) in IPR2018-00186, re: U.S. Pat. No. 9,296,821 B2, Grillo-López et al., "Combination Therapies for B-Cell Lymphomas Comprising Administration of Anti-CD20 Antibodies" (Sep. 27, 2018).
Deposition Transcript of Sylvia Hall-Ellis, Ph.D., (65 pages) in IPR2018-00285 re: U.S. Pat. No. 8,329,172 B2, Grillo-López et al., "Combination therapies for B-cell lymphomas comprising administration of anti-CD20 antibody" (Nov. 3, 2018).
EDGAR Filing Details, https://www.sec.gov/Archives/edgar/data/875045/0000936392-98-000361-index.html (1 pg) (Jun. 29, 2018).
EDGAR From Pick, Customized Forrns Selection page from Internet Archive, https://web.archive.org/web/19970605121538/http://www.sec.gov:80/edaux/formlynx.htm (1 pg) ( Jun. 29, 2018).
Final Written Decision (FWD) (Paper 59), IPR2017-01168 re: U.S. Pat. No. 8,821,873 B2, White, et al., "Treatment of Diffuse Large Cell Lymphoma with Anti-CD20 Antibody", entered Oct. 31, 2018 (39 pages).
Final Written Decision (FWD) in IPR2017-01095, for U.S. Pat. No. 9,296,821 B2, Grillo-López, "Combination Therapies for B-Cell Lymphomas Comprising Administration of Anti-CD20 Antibodies", dated Oct. 4, 2018 (72 pages).
Final Written Decision (FWD) 35 U.S.C. 318(a) and 37 C.F.R. 42.73, (Celltrion, Inc. and Pfizer, Inc. vs. Biogen, Inc. and Genentech, Inc.; Case IPR2016-01614; U.S. Pat. No. 7,820,161, Curd et al., Treatment of Autoimmune Diseases),:1-25 (Feb. 21, 2018).
Flinn et al., "Fludarabine and cyclophosphamide as first therapy for indolent lymphoproliferative disorders: response rates and toxicity" Blood (Abstract 2345), 88(10 SUPPL 1 (Part 1 of 2)):589a (Nov. 15, 1996).

(56) References Cited

OTHER PUBLICATIONS

Flinn et al., "Fludarabine and cyclophosphamide: a highly active and well tolerated regimen for patients with previously untreated indolent lymphomas" Blood (Abstract 1706), 92(10 SUPPL 1 (Part 1 of 2)):413a (Nov. 15, 1998).
Foon et al., Lymphomas, in Williams Hematology Fifth Edition "111" Beutler, E et al., eds., 1995,:1076-1096.
Freedman et al., "Autologous bone marrow transplantation in 69 patients with a history of low-grade B-eell non-Hodgkin's lymphoma" Blood 77(11):2524-2529 (Jun. 1, 1991).
Freedman et al., "Autologous Bone Marrow Transplantation in Poor-Prognosis Intermediate-Grade and High-Grade B-eell non-Hodgkin's Lymphomas in First Remission: A Pilot Study" Journal of Clinical Oncology 11(5):931-936 ( 1993).
Gandarillas et al., "Investigation of prognostic factors in low grade lymphomas" SANGRE (Including English translation (23 pgs)), 43(3 SUPPL 185-190) (Jun. 1998).
Genenteeh, Inc. and Biogen, Ine.'s Patent Owner Response (POR) (Celltrion, Inc. vs. Genentech,Inc. and Biogen, Inc., Case IPR2016-01614; U.S. Pat. No. 7,820,161, Curd et al., Treatment of Autoimmune Diseases; 70 pages (redacted)), (Jun. 2, 2017).
Genentech, Inc. The Access Excellence Collection of Science Updates, Genentech Wayback Machine Website, dated Jan. 23, 1998, pp. 2.
Genentech, Inc., Homepage, Genentech Waybaek Machine Website, dated Jan. 23, 1998., pp. 2.
Genenteeh, Inc., News, Genenteeh Waybaek Machine Website, https://web.arehive.org/web/19980123103005/http://www.gene.com:80/News/., retrieved Jan. 23, 1998., pp. 1.
Genentech, Inc., Recent Press Releases, Genentech Wayback Machine Website, retrieved Jan. 23, 1998., pp. 2.
Genentech, Inc., Search the Genentech Web Site, Genentech Wayback Machine Website, dated Jan. 23, 1998., pp. 1.
Genentech, Inc.'s Response to Petitioner's Additional Discovery, dated Jul. 26, 2017, IPR2016-01614 (U.S. Pat. No. 7,820,161)., pp. 27.
Gianni et al., "In Vivo Purging of Circulating CD34+ Progenitor Cells in Low-Grade Lymphoma with Rituximab and High-Dose Chemotherapy" Blood 92(10 SUPPL 1):119a (Abstract 481) ( 1998).
Grillo-López et al. Antibody, Immunoconjugates, and Radiopharmaceuticals, Ed. (Treatment Options for Patients with Relapsed Low-Grade Follicular Lymphoma: The Role of IDEC-C2B8 (3 pgs)), Stanley E. Order, ( 1995).
Grillo-López et al., "Pilot Efficacy Studies of Rituximab in Combination with Chemotherapy, Biologicals, or Radioimmunotherapy" Annals of Oncology 10( SUPPL 3):179 (Abstract 661) ( 1999).
Grossbard et al., "Monoclonal Antibody Therapy of Lymphoma" American Cancer Society Atlas of Clinical Oncology, Malignant Lymphomas:301-315 ( 2002).
Gutheil et al., "Phase II study of Rituximab (RITUXAN) in Patients With Previously Untreated Low-grade or Follicular Non-Hodgkin's Lymphoma" Annals of Oncology (Abstract 460), 10( SUPPL 3):127 (Jun. 1999).
Habermann et al., "Rituximab-CHOP Versus CHOP Alone or With Maintenance Rituximab in Older Patients With Diffuse Large B-Cell Lymphoma" Journal of Clinical Oncology 24(19):3121-3127 (Jul. 1, 2006).
Hagberg; Case No. 16-206868TVI-OTIR/05; Celltrion, Inc., Sandoz GmBH, Sandoz A/S vs. Biogen, Inc.; transcription and translation of audio recording of Judge Stole, Hans Erik Hagberg, Ingvild Hansen-Bauer, and Judge Arne Kolstad; 14 pages; Certification dated Apr. 9, 2018 attached. (Audio Recording Date Dec. 14, 2017).
Hashimoto et al., "Antibody-dependent cell-mediated cytotoxicity against influenza virus-infected cells" J Infect Dis 148(5):785-794 (Nov. 1983).
Hoffman, M., "Cladribine and fludarabine for the treatment of lymphoproliferative disorders" Cancer Investigation (Abstract 2), 14( SUPPL 1):2-3 ( 1996).
Howard et al., "Rituximab and CHOP Induction Therapy for Newly Diagnosed Mantle-Cell Lymphoma: Molecular Complete Responses Are Not Predictive of Progression-Free Survival" Journal of Clinical Oncology 20(5):1288-1294 (2002).
Judgement Granting Unopposed Motion to Dismiss the Petition and Terminate Proceeding with Prejudice, filed in IPR2018-00231 (Paper 11), for U.S. Pat. No. 9,504,744 B2, White et al., Treatment of diffuse large-cell lymphoma with anti-CD20 antibody, entered Jun. 6, 2018, 3 pages.
Khaled et al., "A randomized EPOCH vs. CHOP front-line therapy for aggressive non-Hodgkin's lymphoma patients: long-term results" Ann Oncol 10(12): 1489-1492 (Dec. 1999).
Lee et al., "Fatal cyclophosphamide cardiomyopathy: its clinical course and treatment" Bone Marrow Transplantation 18(3):573-577 (Sep. 1996).
Lenz et al., "Immunochemotherapy with Rituximab and Cyclophosphamide, Doxorubicin, Vincristine, and Prednisone Significantly Improves Response and Time to Treatment Failure, But Not Long-Term Outcome in Patients with Previously Untreated Mantle Cell Lymphoma: Results of a Prospective Randomized Trial of the German Low Grade Lymphoma Study Group (GLSG)" Journal of Clinical Oncology 23(9):1984-1992 ( 2005).
Lippman et al., "The prognostic significance of the immunotype in diffuse large-cell lymphoma: a comparative study of the T-cell and B-cell phenotype" Blood 72(2):436-441 (Aug. 1988).
Lowdell et al., "Less is More: The Role of Purging in Hematopoietie Stem Cell Transplantation" The Oneologist 2(4):268-274 ( 1997).
Maccio, Antionio and Madeddu, Clelia, "Cisplatin: an old drug with a newfound efficacy—from mechanisms of action to cytotoxicity" Expert Opinion on Pharmacotherapy 14(13):1839-1857 ( 2013).
Machine-Readable Cataloging ("MARC") record of Ex. 1304, Foon, K.A. and Fisher, R.I., Chapter 111: Lymphomas, in Williams Hematology, Fifth Edition, 1076-96 (Beutler, E. et al., eds., 1995) (2 pgs).
Machine-Readable Cataloging ("MARC") record of Ex. 1307, Dana et al., Long-Term Follow-up of Patients Low-Grade Malignant Lymphomas Treated with Doxorubicin-Based Chemotherapy or Chemoimmunotherapy, J. Clin. Oncl., 11(4):644-651 (2 pgs) (Apr. 1993).
Machine-Readable Cataloging ("MARC") record of Ex. 1310, Czuezman et al., IDEC-C2B8 and CHOP Chemoimmunotherapy of Low-Grade Lymphoma, Blood, 86 (10, Suppl. 1), 5521 (Abstract 206) (Nov. 15, 1995) (2 pgs).
Machine-Readable Cataloging ("MARC") record of Ex. 1313, Marcus et al., CVP chemotherapy plus rituximab compared with CVP as first-line treatment for advanced follicular Blood, 105(4): 1417-1423 (Feb. 15, 2005) (2 pgs).
Maloney et al., "Newer treatments for non-hodgkin's lymphoma: monoclonal antibodies" Oncology 12(10 SUPPL 8):63-76 (Oct. 1998).
Maloney, "Advances in Immunotherapy of Hematologic Malignancies" Curr Opin Hematol 5(4):237-243 ( 1998).
Maloney, "Antibody therapy has arrived. Now where does it fit?" Annals of Oncology 10(6):619-621 ( 1999).
McCoy et al., "A Novel Preparing Regimen for Autologous Transplant in Non-Hodgkin's Lymphomas: Long Term Experience with Etoposide and Thiotepa" Bone Marrow Transplantation 33:19-24 ( 2004).
McLaughlin et al., "Fludarabine, Mitoxantrone, and Dexamethasone: An Effective New Regimen for Indolent Lymphoma" Journal of Clinical Oncology 14(4):1262-1268 ( 1996).
McLaughlin et al., "Pivotal Phase III Clinical Trial (PII CT) of the Chimeric Anti-CD20 Antibody (MAB) IDEC-C2B8 in Patients (PTS) with Relapsed Low-Grade or Follicular Lymphoma (LG/F NHL): A Preliminary Report" Annals of Oncology (Abstract 194), 7(57 SUPPL 3) ( 1996).
McLaughlin et al., "Progress and Promise in the Treatment of Indolent Lymphomas" The Oncologist 7:217-225 ( 2002).
McLaughlin et al., "Safety of Fludarabine, Mitoxantrone, and Dexamethasone Combined with Rituximab in the Treatment of Stage IV Indolent Lymphoma" Seminars in Oncology 27 (6 SUPPL 12):37-41 (2000).

(56) References Cited

OTHER PUBLICATIONS

McLaughlin et al., "Stage I-II low-grade lymphomas: A prospective trial of combination chemotherapy and radiotherapy" Arm. Oncol 2( SUPPL 2): 137-140 (1991).
Nakamine et al., "Prognostic significance of clinical and pathologic features in diffuse large B-cell lymphoma" Cancer 71(10):3130-3137 (May 15, 1993).
National Cancer Institute, Cancer Therapy Evaluation Program, Common Toxicity Criteria Manual, Common Toxicity Criteria, Version 2.0 (32 pages), (Jun. 1, 1999).
Nguyen et al., "IDEC-C2B8 anti-CD20 phase II trial: results on bone marrow and peripheral blood tumor response in patients with low grade non-Hodgkin's lymphoma/lymphoproliferative disorders" Blood (Abstract 2277), 90(10 SUPPL 1):511a (1997).
Niitsu, N., "Non-Hodgkin's lymphoma in the elderly: a guide to drug treatment" Drugs & Aging 14(6):447-457 (Jun. 1999).
OCLC record of EX. 1310, Czuczman et al., IDEC-C2B8 and CHOP Chemoirnmunotherapy of Low-Grade Lymphoma, Blood, 86(10, Suppl. 1):55a (Abstract 206) (Nov. 15, 1995), pp. 3.
OCLC record of Ex. 1313, Marcus et al., CVP chemotherapy plus rituximab compared with CVP as first-line treatment for advanced follicular lymphoma, Blood, 105(4): 1417-1423 (Feb. 12, 2005).
OCLC record of Ex. 1307, Dana et al., Long-Term Follow-Up of Patients with Low-Grade Malignant Lymphomas Treated with Doxorubiem-Based Chemotherapy or Chemoinununotherapy., J. Clin. Oncol., 11(4):644-651., pp. 3 (Apr. 1993).
Online Computer Library Center's ("OCLC"), Connexion database record of EX. 1304, Foon, K.A. & Fisher, R.I., Chapter 111: Lymphomas, in Williams Hematology, Fifth Edition, 1076-96 (Beutler, F. et al., eds., 1995), pp. 2.
Patent Owner Preliminary Response (POPR) (Pfizer, Inc. vs. Biogen, Inc., Case IPR2018-00285; U.S. Pat. No. 8,329,172, Grillo-López, Combination Therapies for B-Cell Lymphomas Comprising Administration of Anti-CD20 Antibody; 82 pages; Patent Owner's Exhibit List Attached), (Apr. 11, 2018).
Patent Owner Preliminary Response (POPR) (Pfizer, Inc. vs. Biogen, Inc.; Case IPR2018-00231; U.S. Pat. No. 9,504,744, White et al., Treatment of Diffuse Large-Cell Lymphoma with Anti-CD20 Antibody; 80 pages; Patent Owner's Exhibit List attached), (Mar. 19, 2018).
Patent Owner Preliminary Response (POPR) in IPR2018-00285 re: U.S. Pat. No. 8,329,172 B2, Grillo-López, et al., "Combination therapies for B-cell lymphomas comprising administration of anti-CD20 antibody", dated Apr. 11, 2018 (74 pages).
Patent Owner Response (POR) filed Feb. 26, 2018 by Pfizer in IPR2017-01168 re: U.S. Pat. No. 8,821,873, White,et al., "Treatment of Diffuse Large Cell Lymphoma with Anti-CD20 Antibody" (68 pages).
Patent Owner Response (POR) filed Oct. 8, 2018, in IPR2018-00186 re: U.S. Pat. No. 9,296,821, Grillo-López,et al., "Combination therapies for B-cell lymphomas comprising administration of anti-CD20 antibodies" (82 pages).
Patent Owner slides presented Jul. 24, 2018, at Oral Heating for IPR2017-01168, for U.S. Pat. No. 8,821,873, White, et al., "Treatment of Diffuse Large Cell Lymphoma with Anti-CD20 Antibody", (120 pages).
Patent Owner's Preliminary Response (POPR) Under 37 C.F.R. 42.107, (Pfizer, Inc. vs. Biogen, Inc.; Case IPR2018-00186; U.S. Pat. No. 9,296,821 B2, Grillo-López, Combination Therapies for B-Cell Lymphomas Comprising Administration of Anti-CD20 Antibodies; 76 pages), (Mar. 19, 2018).
Petition for Inter Partes Review in U.S. Pat. No. 8,329,172 B2, IPR2018-00285 (Grillo-López, et al., "Combination therapies for B-eell lymphomas comprising administration of anti-CD20 antibody"), dated Dec. 14, 2017 by Pfizer, Inc. (79 pages).
Petitioner slides at Oral Hearing (Jul. 24, 2018) for IPR2017-01168, for U.S. Pat. No. 8,821,873, White, et al., "Treatment of Diffuse Large Cell Lymphoma with Anti-CD20 Antibody", (28 pages).
Petitioner's Combined Reply in Support of its Petition for Inter Partes Reviews filed Jul. 5, 2018, in IPR2017-01095 re: U.S. Pat. No. 9,296,821,Grillo-López, "Combination therapies for B-eell lymphomas comprising administration of anti-CD20antibodies" regarding U.S. Pat. No. 9,296,821 (44 pages).
Petitioner's Reply to Patent Owner's Response (POPR) filed in IPR2017-01168, U.S. Pat. No. 8,821,873, White, et al., "Treatment of Diffuse Large Cell Lymphoma with Anti-CD20 Antibody", dated May 24, 2018 by Pfizer, Inc. (30 pages).
Physicians' Desk Reference "ADRIAMYCIN RDF, ADRIAMYCIN PFS" (product information), 52 edition, Montvale, NJ :Medical Economics Company, Inc.,:2237-2239 (1998).
Porcu et al., Current Problems in Cancer 22(5):283-368 (1998).
Press et al., "Immunotherapy of Non-Hodgkin's Lymphomas" Hematology:221-240 ( 2001).
Press Release, Genenteeh, Inc. "New Drug for Non-Hodgkin's Lymphoma Available Now," https://www.gene.com/media/press-release5/4835/1997-12-16/new-drug-for-non-hodgkins-lymphoma-avail, Dec. 16, 1997 (2 pgs.).
Rituxan (rituximab), BLA No. 103705, Drugs@FDA: FDA Approved Drug Products, available at https://www.accessdata.fda.gov/scripts/cder/daf/index.cfm?event=overview.process&ApplNo=103705., pp. 4 (Dec. 12, 2017).
Rituxan Full Prescribing Information, Genenteeh Waybaek Machine Website (website label), dated Jan. 23, 1998 (3 pgs).
Rossini et al., "Non-Hodgkin's lymphoma of the elderly. Prognostic factors and outcome" Reeenti Progressi in Medicina 82(5):262-265 ( 1991).
Sean Henahan, "Anti-CD20 Antibodies Combining Well in Lymphoma Patients" Inpharma (3 pgs), 1136(9) (May 1998).
Shipp et al., "Patterns of relapse in large-cell lymphoma patients with bulk disease: implications for the use of adjuvant radiation therapy" J Clin Oncol 7(5):613-618 (May 1989).
Solal-Celigny et al., "Recombinant Interferon ALFA-2b Combined with a Regimen Containing Doxorubicin in Patients with Advanced Follicular Lymphoma" The New England Journal of Medicine 329(22):1608-1614.
Solimando et al., "Doxorubicin-induced hypersensitivity reactions" Drug Intell Clin Pharm 18(10):808-811 (Oct. 1984).
Summerhayes, M., "Rituximab: a new modality in lymphoma treatment" European Hospital Pharmacy 5(3):126-133 (Sep. 1999).
Termination of the Proceeding in IPR2018-00186 (Paper No. 34), U.S. Pat. No. 9,296,821 B2, Grillo-López, "Combination Therapies for B-Cell Lymphomas Comprising Administration of Anti-CD20 Antibodies", entered Nov. 8, 2018 (5 pages).
The CALGB Newsletter, Quarterly Newsletter of the Cancer and Leukemia Group B, vol. 7, No. 1, Spring 1998, "Rituxan," p. 4-5.
Tirelli et al., "CHOP is the standard regimen in patients > or=70 years of age with intermediate-grade and high-grade non-Hodgkin's lymphoma: results of a randomized study of the European Orgamzation for Research and Treatment of Cancer Lymphoma Cooperative Study Group" J Clin Oncol 16(1):27-34 (Jan. 1998).
Translation of transcription of Steinar Aamdal Testimony; Oslo District Court; Court case No. 16-206868TVI-OTIR/05, pp. 1-63 (Testimony Date Dec. 13, 2017).
Turgeon, M. Clinical Hematology: Theory and Procedures (re: lymphocytes), 4th edition, Philadelphia: Lippincott Williams & Wilkins,:221 ( 2005).
Understanding Maintenance Therapy, Caneer.net, http://www.cancer.net/navigating-cancer-care/how-cancer-treated/understanding-maintenance-therapy (3 pgs) ( Jul. 21, 2017).
Velasquez et al., "Risk classification as the basis for clinical staging of diffuse large-cell lymphoma derived from 10-year survival data" Blood 74(2):551-557 (Aug. 1, 1989).
Vidal et al., "Rituximab maintenance improves overall survival of patients with follicular lymphoma-Individual patient data meta-analysis" European Journal of Cancer 76:216-225 ( 2017).
von Mehren et al., "Monoclonal Antibody Therapy for Cancer" Annual Review of Medicine 54:343-369 ( 2003).
Vose et al., "Phase II Study of Rituximab in Combination with CHOP Chemotherapy in Patients with Previously Untreated Intermediate- or High-Grade Non Hodgkin's Lymphoma (NHL)" Annals of Oncology (Abstract 195), 10( SUPPL 3):58 ( 1999).
Waldmann et al., "Emerging Therapies: Spectrum of Applications of Monoclonal Antibody Therapy" Hematology:394-408 (2000).

(56) References Cited

OTHER PUBLICATIONS

Weijl et al., "Free radicals and antioxidants in chemotherapy induced toxicity" Cancer Treatment Reviews 23:209-240 (1997).
Wendum et al., "Follicular large-cell lymphoma treated with intensive chemotherapy: an analysis of 89 cases included in the LNH87 trial and comparison with the outcome of diffuse large B-cell lymphoma. Groupe d'Etude des Lymphomes de l'Adulte" J Clin Oncol 15(4):1654-1663 (Apr. 1997).
Whelan et al., "Fludarabine phosphate for the treatment of low grade lymphoid malignancy" Br J Cancer 64(1):120-123 (Jul. 1991).
Yuen, A, "Progress in the non-Hodgkin's lymphomas" Annals of Oncology 10( SUPPL 6):S19-S22 (1999).
Zucca et al., "Management of rare forms of lymphoma" Current Opinion in Oncology 10(5):377-384 (1998).
"A randomized, phase III trial to determine the effect of consolidation with rituximab (IDEC C2B8-MabThera) in patients with CD20+ follicular or mantle cell lymphoma having received induction therapy with rituximab weekly x4," Minutes Protocol SAKK 35/98, Swiss Group for Clinical Cancer Research, Dec. 18, 1998, Activation Date Jan. 7, 1998, pp. 1-27.
"Cytoxan®, Etophose®, Leukeran®, Mepron®, Oncovin®," Physicians' Desk Reference (52nd ed. 1998), Published by Medical Economics Company, Inc. (11 pages).
"Dictionary of Cancer Terms," National Cancer Institute at the National Institutes of Health, http://www.cancergov.dictionary?CdrID=45735, 1 pp, printed May 22, 2012.
"GlaxoSmithKline and Genmab Announce Results from a Study of Arzerra in Rituximab Refractory Follicular NHL," PharmaLive.com, pp. 1-2, Aug. 17, 2009. Obtained online at http://www.pharmalive.com/News/Print.cfm?articleid=645905.
"Phase II Trial of CHOP Followed by Rituximab, a Chimeric Monoclonal Anti-CD20 Antibody, for Treatment of Newly Diagnosed Follicular Non-Hodgkin's Lymphoma: SWOG 9800," Oncology Review Article, Mar. 1, 2002, pp. 1-2.
"Rituxan™ (Rituximab)" Physicians' Desk Reference (53rd ed. 1999), Published by Medical Economics Company (11 pages).
"Understanding Maintenance Therapy," Approved by the Cancer. Net Editorial Board, Aug. 2015, ASCO Website Printout, retrieved Jul. 1, 2016, pp. 1-3.
"Vincristine," Wikipedia, the free encyclopedia, retrieved Jul. 23, 2015, https://en.wikipedia.org/wiki/Vincristine (3 pages).
[unknown author] "IDEC Pharmaceuticals Announces Positive Preliminary Results for Pivotal Trial of IDEC-C2B8" *The Free Library* May 21, 1996. [retrieved again on Aug. 2, 2010 Retrieved from http://www.thefreelibrary.com/IDEC+PHARMACEUTICALS+ANNOUNCES+POSITIVE+PRELIMINARY+RESULTS+FOR . . . -a018307934.
[unknown author] "IDEC Pharmaceuticals Announces Positive Preliminary Results for Pivotal Trial of IDEC-C2B8" The Free Library May 21, 1996. pp. 1-3 Retrieved from http://www.thefreelibrary.com/IDEC+PHARMACEUTICALS+ANNOUNCES+POSITIVE+PRELIMINARY+RESULTS+FOR . . . -a018307934 as retrieved on Aug. 2, 2010.
[unknown author] "Non-progressing, low-grade NHL: Risk reduction demonstrated in NCI-sponsored trial using up to 16 doses of RITUXAN following CVP in NHL" [retrieved on Aug. 25, 2010]. pp. 1-6 Retrieved from http://www.rituxan.com/lymphoma/hcp/indications/E1496/index.m.
"Biological Therapy for Cancer Treatment", Stanford Cancer Center, https://web.archive.org/web/20131617382400/http://cancer.stanford.edu/information/cancerTreatment/methods/biological.html, 2009, pp. 1-8 (Retrieved Dec. 2, 2014).
"Lymphomas: New Recognitions and Therapy Strategies", Wolfgang Hiddemann, Martin Dreyling, Harald Stein editors, Georg Thieme Verlag, Stuttgart, New York, pp. 78-81 (2005), English translation and original in German.
"NCI—Cooperative Group—Industry Relationship Guidelines", updated May 29, 2008 http://ctep.cancer.gov/industrycollaborations2/guidelines.htm, retrieved Aug. 25, 2015, pp. 1-3.
"Treatment of intermediate or high-grade malignant NHL," ed. Junliang Ma, Modern Oncology Manual, 1st ed., Liaoning Science and Technology Press, Jan. 1996, p. 343 (partial English translation included).
1999 NCI Cancer Toxicity Criteria Manual, Common Toxicity Criteria, Version 2.1, Jun. 1, 1999, available at https://ctep.cancer.gov/protocoldevelopment/electronic_applications/docs/ctcmanual_v4_10-4-99.pdf (retrieval date unavailable) (32 pages).
2011 RITUXAN (Rituximab) full prescribing information, pp. 1-8 (Initial US Approval Nov. 1997, Revised Jan. 2011).
62 Federal Register 115, Jun. 16, 1997, pp. 32619.
62 Federal Register 32, Food and Drug Administration, Advisory Committees; Tentative Schedule of Meetings for 1997, Feb. 18, 1997, pp. 7237-7240.
Adams R. A., et al., "Direct implantation and serial transplantation of human acute lymphoblastic leukemia in hamsters, SB-2", Cancer Res., 1968, vol. 28, No. 6, pp. 1121-1125.
Adams R. A.. "Formal discussion: the role of transplantation in the experimental investigation of human leukemia and lymphoma.", Cancer Res, 1967, vol. 27, pp. 2479-2482.
Aguiar-Bujanda, et al., "Critical appraisal of rituximab in the maintenance treatment of advanced follicular lymphoma," Cancer Management and Research, 2015, vol. 7, pp. 319-330.
Aisenberg A. C., "Coherent view of non-Hodgkin's lymphoma." J Clin Oncol., 1995, vol. 13, pp. 2656-2675.
Alas S., et al., "Inhibition of interleukin 10 by rituximab results in down-regulation of bcl-2 and sensitization of B-cell non-Hodgkin's lymphoma to apoptosis", Clin. Cancer Res., 2001, vol. 7, No. 3, pp. 709-723.
Alas S., et al., "Potentiation of fludarabine cytotoxicity on non-Hodgkin's lymphoma by pentoxifylline and rituximab", Anticancer Res., 2000, vol. 20, No. 5A, pp. 2961-2966.
Alas S., et al., "Rituximab modifies the cisplatin mitochondrial signaling pathway, resulting in apoptosis in cisplatin-resistant non-Hodgkin's lymphoma", Clin. Cancer Res., 2002, vol. 8, No. 3, pp. 836-845.
Al-Ismail, "Combination chemotherapy Including Epirubicin for the Management of Non-Hodgkin's Lymphoma", European J. Cancer and Clinical Oncology, 1987, vol. 23, pp. 1379-1384.
Almasri N. M., et al. *Am. I Hematol.* 40: 259-63, 1992. Reduced expression of CD20 antigen as a characteristic marker for chronic lymphocytic leukemia.
Amit A. G., et al., "Three-dimensional structure of an antigen-antibody complex at 2.8 A resolution," *Science* 233(4765): 747-53 (1986).
Anderson K. C., et al. *Blood* 63(6): 1424-33, 1984. Expression of human B cell-associated antigens on Leukemias and lymphomas: a model of human B cell differentiation.
Anderson K. C., et al. *Blood* 69(2): 597-604, 1987. Hematologic engraftment and immune reconstitution Eost transplantation with anti-B 1 purged autologous bone marrow.
Anderson, et al. Second IBC Int'l. Conference on Antibody Engineering, San Diego, Dec. 16-18, 1991. Immunoreactivity and effector function associated with a chimeric anti-CD20 antibody (abstract of presentation).
Anderson, et al., "Targeted anti-cancer therapy using rituximab, a chimeric anti-CD20 antibody (IDEC-C2B8) in the treatment of non-Hodgkin's B-cell lymphoma," Biochem. Soc. Trans. 25(2): 705-08, 1997.
Appelbaum F.R. *Hem. Onc. Clin. N Amer.* 5(5): 1013-25, 1991. Radiolabeled monoclonal antibodies in the treatment of non-Hodgkin's lymphoma.
Arber, et al., "The 2016 revision to the World Health Organization classification of myeloid neoplasms and acute leukemia," Blood, 2016, vol. 127, No. 20, pp. 2391-2405.
Arber, et al., "Bone marrow biopsy involvement by non-Hodgkin's lymphoma: frequency of lymphoma types, patterns, blood involvement, and discordance with other sites in 450 specimens," Am. Journ. Surg. Pathol., Dec. 2005, vol. 29, No. 12, pp. 1549-1557.
Archived ECOG website, Jun. 8, 1998, retrieved from parent URL http://web.archive.org/web/19981212013740/httplecog.dfci.harvard.edu on Mar. 19, 2015 and Mar. 20, 2015, pp. 1-109.

(56) References Cited

OTHER PUBLICATIONS

Ardeshna, et al., "Long-term effect of a watch and wait policy versus immediate systemic treatment for asymptomatic advanced-stage non-Hodgkin lymphoma: a randomised controlled trial," Lancet, 2003, 362:516-5222.
Arico, et al., "Long term survival after heart transplantation for doxorubicin induced cardiomyopathy", Arch Dis Child 66, 1991, pp. 985-986.
Armitage, et al., "Bone Marrow Transplantation," Clinical Oncology, Abeloff, et al., Eds. 1995, 295-305.
Armitage J. O., et al. Cancer 50: 1695-1702, 1982. Predicting therapeutic outcome in patients with diffuse histiocytic lymphoma treated with cyclophosphamide, adriamycin, vincristine and prednisone (CHOP).
Armitage J. O., et al. I Clin. Oncol. 16(8): 2780-95, 1998. New approach to classifying non-Hodgkin's lymphomas: clinical features of the major histologic subtypes. Non-Hodgkin's Lymphoma Classification Project.
Armitage J. O., "Treatment of Non-Hodgkin's Lymphoma." N Engl. J. Med. 328(14): 1023-30 (Apr. 1993).
Arranz R., et al. *J. Clin. Oncol.* 16(4): 1538-46, 1998. Role of interferon alfa-2b in the induction and maintenance treatment of low-grade non-Hodgkin's lymphoma: results from a prospective, multicenter trial with double randomization.
Aviles, et al., "Interferon Alpha 2b as Maintenance Therapy in Low Grade Malignant Lymphoma Improves Duration of Remission and Survival", Leukemia and Lymphoma, 1996, vol. 20, pp. 495-499.
Aviles, et al., "Maintenance therapy with interferon alfa 2b in patients with diffuse large cell lymphoma", Investigational New Drugs, 1992, vol. 10, pp. 351-355.
Aviles, A., "The role of Interferon as Maintenance Therapy in Malignant Lymphoma", Medical Oncology, 1997, vol. 14, pp. 153-157.
Aviles, et al., "Long-Term Results in Patients with Low-Grade Nodular Non-Hodgkin's Lymphoma: A randomized trial comparing chemotherapy plus radiotherapy with chemotherapy alone," Acta Oncologica, 1991, vol. 30, No. 3, pp. 329-333.
Azogui, et al. *J. Immunol.* 131: 1205-08, 1983. Inhibition of IL-2 production after human allogeneic bone marrow transplantation.
Badger C.C., et al. *Cancer Res.* 46: 6223-28, 1986. Experimental radioimmunotherapy of murine lymphoma with $^{131}$I-labeled anti-T-cell antibodies.
Bagley, et al., "Advanced Lymphosarcoma: Intensive Cyclical Combination Chemotherapy with Cyclophosphamide, Vincristine, and Prednisone," Annals of Internal Medicine, 1972, 76:227-234.
Belhadj K., et al. *Ann. Oncol.* 15: 504-10, 2004. Efficiency of in vivo purging with rituximab prior to autologous peripheral blood progenitor cell transplantation in B-cell non-Hodgkin's lymphoma: a single institution study.
Bennett, et al., "Cancer Insurance Policies in Japan and the United States," W. J. Med, 1998, 168(1):17-22.
Bentley, et al., "Low-grade non-Hodgkin's lymphoma—Biology and therapeutic approaches", *Australian and New Zealand Journal of Medicine* 27, 1997, pp. 150-155.
Berinstein N., et al. *Proc. Amer. Assn. Cancer Res.* 38: 85, abst. No. 567, Mar. 1997. IDEC-C2B8 (rituximab) levels correlate with response in low-grade or follicular non-Hodgkin's lymphoma (LG-F-NHL).
Berinstein N. L., et al. *Ann. Oncol.* 9: 995-1001, 1998. Association of serum rituximab (IDEC-C2B8) concentration and anti-tumor response in the treatment of recurrent low-grade or follicular non-Hodgkin's lymphoma.
Berinstein, "Principles of maintenance therapy," *Leukemia Res.* 30 Suppl. 1: S3-10 (2006).
Berkahn, et al., "In vivo purging with rituximab prior to collection of stem cells for autologous transplantation in chronic lymphocytic leukemia," *J. Hemathother. Stem Cell Res.* 11(2): 315-20 (2002).
Beychok S. (in) *Cells of Immunoglobulin Synthesis*, B. Pernis, et al., eds. New York: Academic Press, 1979, pp. 69-88. Comparative aspects of in vitro and cellular assembly of immunoglobulins.

Bhan A. K., et al. *J. Exp. Med.* 154: 737-49, 1981. Stages of B cell differentiation in human lymphoid tissue.
Bierman, et al., "High-dose therapy with autologous hematopoietic rescue for follicular low-grade non-Hodgkin's lymphoma," J. Clin. Oncol. 15(2):445-50 (1997).
Bierman P. J., et al. (in) Hoffman, R., ed., *Hematology*, 2d. ed., Churchill Livingstone, 1995, Chapter 81, pp. 1278-98. Clinical manifestations and staging of and therapy for non-Hodgkin's lymphomas.
*Biogen IDEC Inc. v. Corixa Corp.*, Case No. 01-CV-1637 IEG (RBB), Order Granting Patentees' Motion for Reconsideration, etc. (S.D. Cal., Jan. 22, 2004).
*Biogen IDEC Inc. v. Corixa Corp.*, Case No. 01-CV-1637 IEG [Doc. Nos. 635, 552, 486] (S.D. Cal. Jan. 22, 2004).
*Biogen IDEC Inc. v. Corixa Corp.*, Case No. 01-CV-1637 TEG (RBB), Stipulation of Dismissal of Claims and Counterclaims with Prejudice and Order (S.D. Cal., May 13, 2004).
Biogen's Patent Owner Preliminary Response filed Apr. 15, 2015 in Response to Petition Inter Partes Review of U.S. Pat. No. 8,329,172 dated Dec. 15, 2014 (U.S. Appl. No. 11/840,956, Antonio J. Grillo-Lopez, Combination Therapies for B-Cell Lymphomas Comprising Administration of Anti-Cd20 Antibody, filed Aug. 18, 2007) pp. 1-69.
*Biological Therapies: Using the Immune System to Treat Cancer*, National Cancer Institute, http://web.archive.org/web/19980216091909/http://cancernet.nci.nih.gov/clinpdq/therapy/Biological_Therapies:_Using_the_Immune_System_to_Treat_Cancer.html (archived Feb. 16, 1998) pp. 1-5.
Bishop, et al, "A Randomized Trial of High Dose Cyclophosphamide, Vincristine Prednisone ,and Plus or Minus Doxorubicin (CVP Versus CAVP) With Long-Terra Follow-Up in Advanced Non-Hodgkin's Lymphoma," Leukemia 1987, vol. 1, No. 6, pp. 508-513.
Blackwelder, William C., "'Proving the Null Hypothesis' in Clinical Trials", Controlled Clinical Trials, 1982, vol. 3, pp. 345-353.
Bodkin, et al., "Pharmacokinetic analysis of serum concentrations of the chimeric anti-CD20 antibody IDEC-C2B8 in patients with relapsed B cell lymphoma", Proc Annu Meet Am Assoc Cancer Res 36:365 (#2175), Mar. 1995.
Boon, "Toward a genetic analysis of tumor rejection antigens," *Adv. Cancer Res.* 58: 177-210 (1992).
Bosly A., et al. *Nouv. Rev. Fr. Hematol.* 32(1): 13-16, 1990. Interleukin-2 after autologous bone marrow transplantation as consolidative immunotherapy against minimal residual disease.
Boulianne G.L., et al. *Nature* 312: 643-46, 1984. Production of functional chimeric mouse/human antibody.
Brice, et al., "Comparison in low-tumor-burden follicular lymphomas between an initial no-treatment policy, prednimustine, or interferon alfa: a randomized study from the Group d'Etude des Lymphomas Folliculaires," *J. Clin Oncol.*, 1997, 15(3): 1110-1117.
Brown S.L., et al., "Treatment of B-cell lymphomas with anti-idiotype antibodies alone and in combination with alpha interferon"; Blood 73:651-661, 1989.
Brunner K.T., et al. *Immunology* 14(2): 181-96, 1968. Quantitative assay of the lytic action of immune lymphoid cells on Cr-labelled allogeneic target cells in vitro; inhibition by is antibody an by drugs.
Buchsbaum D. J., et al. *J Rad. Oncol. Biol. Phys.* 18: 1033-41, 1990. A comparison of $^{131}$I labeled monoclonal antibody 17-1A treatment to external beam irradiation on the growth of LS174T human colon carcinoma xenografts.
Buchsbaum D. J., et al. *Cancer Res.* 50: 993s-999s, 1990. Comparative binding and preclinical localization and therapy studies with radiolabeled human chimeric and murine 17-1A monoclonal antibodies.
Buchsbaum D. J., et al. *Cancer Res.* 52: 637-642, 1992. Improved delivery of radiolabeled anti-B1 monoclonal antibody to Raji lymphoma xenografts by predosing with unlabeled anti-B1 monoclonal antibody.
Buchsbaum D. J., et al. *Cancer Res.* 52: 6476-81, 1992. Therapy with unlabeled and $^{131}$I labeled pan-B-cell monoclonal antibodies in nude mice bearing Raji Burkitt's lymphoma xenografts.
Buchsbaum D. J., et al. *Li Rad. Oncol. Biol. Phys.* 25(4): 629-38, 1993. Comparison of $^{131}$I and $^{90m}$Y-labeled monoclonal antibody 17-1A for treatment of human colon cancer xenografts.

(56) References Cited

OTHER PUBLICATIONS

Buske, et al., "Monoclonal Antibody Therapy for B Cell Non-Hodgkin's Lymphomas: Emerging Concepts of a Tumour-targeted Strategy", European Journal of Cancer, vol. 35(4), 1999, pp. 549-557.
Byrd, et al., "Old and New Therapies in Chronic Lymphocytic Leukemia: Now Is the Time for a Reassessment of Therapeutic Goals", Seminars in Oncology, vol. 25, No. 1 Feb. 1998; pp. 65-74.
Byrd J.C. Cancer Biother. Radiopharm. 14(4)L 323, 1999. Rituximab therapy in patients with chronic lymphocytic leukemia.
Byrd J.C., et al. Blood 92(10 Suppl. 1): 106a, abst. No. 432 Nov. 1998. Rituximab therapy in hematologic malignancy patients with circulating blood tumor cells.: association with increased infusion-related side effects and rapid tumor lysis.
Byrd J.C., et al. Blood 92(10 Suppl. 1): 106a, abst. No. 433 Nov. 1998. Rituximab therapy in previously treated Waldenstrom's Macroglobulinemia: Preliminary evidence of activity.
Byrd J.C., et al. J Clin. Oncol. 17(3): 791-795, Mar. 1999. Rituximab therapy in hematologic malignancy patients with circulating blood tumor cells: association with increased infusion-related side effects and rapid blood tumor clearance.
Byrd J.C., et al. J. Clin. Oncol. 19(8): 2153-64, 2001. Rituximab using a thrice weekly dosing schedule in B-cell chronic lymphocytic leukemia and small lymphocytic lymphoma demonstrates clinical activity and acceptable toxicity.
Cabanillas et. al., "Clinical, Biologic, and Histologic Features of Late Relapses in Diffuse Large Cell Lymphoma", Blood, Feb. 1992, vol. 79, No. 4, pp. 1024-1028.
Cabanillas, F., et al., "Anti-CD20 Antibody (MAB), IDEC-C2B8: Clearance of BCL-2 t(14;18) positive cells from peripheral blood (PB) and bone marrow (BM) in patients (PTS) with relapsed low-grade or follicular lymphoma (LG/F NHL)" Blood 88(10):91a (#351), Nov. 1996.
Caligiuri M.A., et al. J Clin. Oncol. 9(12): 2110-19, 1991. Extended continuous infusion low-dose recombinant interleukin-2 in advanced cancer: prolonged immunomodulation without significant toxicity.
Caligiuri M.A., et al. J. Clin. Invest. 91(1): 123-32, 1993. Selective modulation of human natural killer cells in vivo after prolonged infusion of low dose recombinant interleukin 2.
Caligiuri M.A. Semin. Oncol 20(6 Suppl 9): 3-10, 1993. Low-dose interleukin-2 therapy: rationale and potential clinical applications.
Calvert J. E., et al. Semin. Hematol. 21(4): 226-243, 1984. Cellular events in the differentiation of antibody-secreting cells.
Campbell, et al., "B-Lymphocyte Responses," Clinical Oncology, Abeloff, et al., Eds., Published by Churchill Livingstone, Inc. 1995, 100-126.
cancer.gov, "Combination Chemotherapy with or without Monoclonal Antibody Therapy in Treating Patients with Stage III or Stage IV Low-Grade Non-Hodgkin's Lymphoma", updated Mar. 3, 2015, retrieved from http://www.cancer.gov/clinicaltrials/search/view?cdrid=653666&version=HealthProfessional&protocolsearchid=13923514, pp. 1-4.
CancerNetwork, "Understanding Maintenance Therapy," approved Aug. 2015, http://www.cancer.net/navigating-cancer-care/how-cancer-treated/understanding-maintenance-therapy retrieved Jul. 21, 2017 (3 pages).
CancerNetwork, "Lymphoma—Non-Hodgkin", copyright 2005-2012, pp. 1-6; www.cancer.net/cancer-types/lymphoma-non-hodgkin/subtypes.
CancerNetwork, "Rituximab Effective in Patients with Bulky NHL," Issue 2, vol. 8. Feb. 1, 1999, http://www.cancernetwork.com/articles/rituximab-effective-patients-bulky-nhl, pp. 1-3.
Canellos, et al., "Chemotherapy of the Non-Hodgkin's Lymphomas," Cancer 1987, vol. 42, No. 2, pp. 932-940.
Carlson, R. "Rituximab plus CHOP: a new approach for non-Hodgkin's lymphoma?" Inpharma No. 1116:7-8 (Dec. 6, 1997) (Chemotherapy Foundation Symposium XV, New York, US, Nov. 1997).

Carrasquillo J.A., et al. J NucL Med. 26: 67, abst. No. 276, 1985. Improved imaging of metastatic melanoma with high dose 9.2.27 In-111 monoclonal antibody.
Catovsky D., et al. Eur J. Cancer 31A(13/14): 2146-54, 1995. Key issues in the treatment of chronic lymphocytic leukemia (CLL).
Cayeux S., et al. Blood 74(6): 2270-77, 1989. T-cell ontogeny after autologous bone marrow transplantation: failure to synthesize interleukin-2 (IL-2) and lack of CD2– and CD3– mediated proliferation by both CD4– and CD8+ cells even in the presence of exogenous IL-2.
Chemocare.com, "Oncovin" 2013, pp. 1-6; www.chemocare.com/chemotherapy/drug-info/Oncovin.aspx.
Chen J. J., et al. J Immunol. 143(3): 1053-57, 1989. Tumor idiotype vaccines. VI. Synergistic antitumor effects with combined "internal image" anti-idiotypes and chemotherapy.
Chen, et al., "Synergistic Anti-proliferative Effect of Metformin and Sorafenib on Growth of Anaplastic Thyroid Cancer Cells and their Stem Cells," Oncology Reports 2014, vol. 33, pp. 1994-2000.
Cheson B.D., et al. Blood 87: 4990-97, 1996. National Cancer Institute-specified working group guidelines for chronic lymphocytic leukemia: revised guidelines for diagnosis and treatment.
Cheson, "Current Approaches to Therapy for Indolent Non-Hodgkin's Lymphoma," Nutritional Outlook, Review Article, Oct. 2, 1998, pp. 1-16.
Cheson, "Radioimmunotherapy of non-Hodgkin lymphomas," Blood 101(2): 391-8 (2003), Epub Sep. 19, 2002.
Cheson, B., et al., "Report of an International Workshop to Standardize Response Criteria for Non-Hodgkin's Lymphomas", J Clin Oncol 17(4):1244-53, Apr. 1999.
Chinn P., et al. Proc. Ann. Mtg. Am. Assn. Cancer Res. 33: 337, abst. No. 2012, 1992. Production and characterization of radiolabeled anti-CD20 monoclonal antibody: potential application to treatment of B-cell lymphoma.
Chinn P.C., et al. Int. J Oncol. 15(5): 1017-25, Nov. 1999. Preclinical evaluation of 90Y-labeled anti-CD20 monoclonal antibody for treatment of non-Hodgkin's lymphoma.
Chinn, et al., "A Y-labeled anti-CD20 monoclonal antibody conjugated to MX-DTPA, a high-affinity chelator for yttrium," Proc. Am. Assn. Cancer Res. 1999, 40: 574, abst. No. 3786 (1 page).
Chisesi et. al., "Randomized Study of Chlorambucil (CB) Compared to Interferon (Alfa-2b) Combined with CB in Low-Grade Non-Hodgkin's Lymphoma: An interim report of a randomized study", Eur. J. Cancer, 1991, vol. 27, Supp. 4, pp. S31-S33.
Chomczynki P., et al. Anal. Biochem. 162: 156-59, 1987. Single-step method of RNA isolation by acid guanidinium thiocyanate-phenol-chloroforin extraction.
Chow K. U., et al. Haematologica 87: 33-43, 2002. Anti-CD20 antibody (IDEC-C2B8, rituximab) enhances efficacy of cytotoxic drugs on neoplastic lymphocytes in vitro: role of cytokines, complement, and caspases.
Chow, et al., "Oncogene-specific formation of chemoresistant murine hepatic cancer stems cells," Hepatology, 2012, 56(4), pp. 1331-1341.
Clark E. A., et al. J Cell. Biochem. (Suppl. 9A): 63, 1985. Anti-Bp35 antibody induces human B cell proliferation: implications for in vivo immunotherapy.
Clark E. A., et al. Proc. Nat'l Acad. Sci. USA 82(6): 1766-70, 1985. Role of the Bp35 cell surface polypeptide in human B-cell activation.
Classon B. J., et al. J. Exp. Med. 169(4): 1497-1502, 1989. The primary structure of the human leukocyte antigen CD37, a species homologue of the rat MRC OC-44 antigen.
Clendeninn, N. J., et al., "Phase I/II trials of CAMPATH-1H, a humanized anti-lymphocyte monoclonal antibody (MoAb), in non-Hodgkin's lymphoma (NHL) and chronic lymphocytic leukemia (CLL).", Blood, Nov. 1992, vol. 80, No. 10, Supplement 1, Abstract #624, p. 158a.
Clinical Review of BLA Reference No. BLA 97-0260 and BLA 97-0244, pp. 1-40 with cover page signed: Nov. 1997; the source is available on the Internet (as of Nov. 28, 2013) at the following (URL): http://www.fda.gov/downloads/Drugs/DevelopmentApprovalProcess/HowDrugsareDevelopedandApproved/ApprovalApplications/TherapeuticBiologicApplications/ucm113330.pdf.

(56) References Cited

OTHER PUBLICATIONS

Clinical Trials (PDQ®); "Phase III Randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma" http://www.cancer.gov/clinicaltrials/search/view?cdrid=65935 &version—HealthProfessional; First Published: Jan. 1, 1998; Last Modified: Aug. 27, 2010; Retrieved: Jan. 14, 2013; pp. 1-6.
Clinical Trials (PDQ®); "Phase III randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma"; First Published: Jan. 1, 1998; Last Modified: Aug. 27, 2010; http://www.cancer.gov/clinicaltrials/search/view?cdrid=65935 &version=HealthProfessional; pp. 1-7 (Retrieved Jan. 17, 2013).
ClinicalTrials.gov report on the NCT00003204 (ECOG 1496) Clinical Trial (Jan. 27, 2014) http://clinicaltrials.gov/show/NCT00003204 pp. 1-5 (retrieved Dec. 2, 2014).
ClinicalTrials.gov, "Combination Chemotherapy With or Without Monoclonal Antibody Therapy in Treating Patients With Stage III or Stage IV Low-Grade Non-Hodgkin's Lymphoma", First Received: May 2, 2000; Last updated: Feb. 26, 2013; Last verified: Feb. 26, 2013 pp. 1-4; http://clinicaltrials.gov/show/NCT00003204.
Cogliatti S.B., et al. *Sw. Med. Weekly* 192: 607-17, 2002. Who is *WHO* and what was *REAL*?
Cohen, et al., "Retreatment with rituximab alone induces sustained remission in a patient with follicular lymphoma with multiple extranodal sites of involvement, relapsing soon after primary treatment with fludarabine-rituximab," *Hematol. J.* 4(2): 151-3 (2003).
Cohen, et al. *Leuk. Lymphoma* 43(7): 1485-87, 2002. Large B-cell lymphoma manifesting as an invasive cardiac mass: sustained local remission after combination of methotrexate and rituximab.
Coiffier B. *Ann. Oncol.* 83(Suppl 1): S73-S74, 2004. New treatment strategies in lymphomas: aggressive lymphomas.
Coiffier, et al. *Blood* 92(6): 1927-32, 1998. Rituximab (anti-CD20 monoclonal antibody) for the treatment of patients with relapsing or refractory aggressive lymphoma: a multicenter phase II study.
Coiffier, et al. *N Engl. J. Med.* 346(4): 235-42, 2002. CHOP chemotherapy plus rituximab compared with CHOP alone in elderly patients with diffuse large-B-cell lymphoma.
Coiffier, et al., "A multicenter, randomized phase II study of rituximab (chimeric anti-CD20 mAb) at two dosages in patients with relapsed or refractory inteiniediate or high-grade NHL (IHG-NHL) or in elderly patients in first-line therapy," Blood Nov. 15, 1997, vol. 90, No. 10, pp. 510a, Abstract 2271.
Coiffier, "Rituximab in combination with CHOP improves survival in elderly patients with aggressive non-Hodgkin's lymphoma," *Semin. Oncol.* 29(2 Suppl. 6): 18-22 (2002).
Coiffier, B., "What treatment for elderly patients with aggressive lymphoma?," Annals of Oncology, 1994, vol. 5, pp. 873-875.
Coleman M., et al. *Blood* 102(11 pt. 1): 29a, abst. No. 29, 2003. The BEXXAR® therapeutic regimen (tositumomab and Iodine 1-131 tositumomab) produced durable complete remissions in heavily pretreated patients with non-Hodgkin's lymphoma (NHL), rituximab relapsed/ refractory disease, and rituximab-naive disease.
Coleman, "Glucocorticoids in cancer therapy," Biotherapy, 1992, No. 4, pp. 37-44.
Collins, "The Lunch", https://www.gene.com/stories/the-lunch?topic—hematology, pp. 1-10, retrieved Aug. 7, 2017 (as cited by Examiner in Aug. 14, 2017 OA for U.S. Appl. No. 13/524,837).
Colombat P., et al. *Blood* 97: 101-06, 2001. Rituximab (anti-CD20 monoclonal antibody) as single first-line therapy for patients with follicular lymphoma with a low tumor burden: clinical and molecular evaluation.
Comella, et al., "Combination chemotherapy (CVP or CHOP)-radiotherapy approach in early stage non-Hodgkin's lymphomas," Tumori, vol. 68, No. 2, pp. 137-142, (1982).
Commission Decision of "MabThera—Rituximab" and MabThera EU Summary of Product Characteristics (SmPC) Jun. 2, 1998 (39 pages).

Cope. *Oncology* 8(4): 100, 1994. Antibody shows promise in treating B-cell lymphoma.
Curti B.D. *Crit. Rev. Oncol. Hematol.* 14(1): 29-39, 1993. Physical barriers to drug delivery in tumors.
Czuczman, et al., "Chemoimmunotherapy of Low-Grade Lymphoma with the Anti-CD20 Antibody IDEC-C2B8 in Combination with CHOP Chemotherapy," Cancer Investigation (abstract 53) 14(Suppl. 1):59-61 (1996).
Czuczman, et al., "IDEC-C2B8/CHOP chemoimmunotherapy in patients with low grade lymphoma: Clinical and bcl-2 (PCR) results," *I Mol. Med.* 75(7): B231, abstract #258 (1997).
Czuczman, et al., "IDEC-C2B8/CHOP chemoimmunotherapy in patients with low-grade lymphoma: Interim clinical and bcl-2 (PCR) results," Annals of Oncology, 1996, vol. 7, Suppl. 1, pp. 56-57.
Czuczman, et al., "Prolonged Clinical and Molecular Remission in Patients With Low-Grade or Follicular Non-Hodgkin's Lymphoma Treated With Rituximab Plus CHOP Chemotherapy: 9-Year Follow-Up," J. Clin. Oncol. 2004, vol. 22, No. 23, pp. 4711-4716.
Czuczman M., et al. *Blood* 94(10 Supp. 1): 99a, abst. No. 432, 1999. Rituximab/CHOP chemoimmunotherapy in patients (PTS) with low grade lymphoma (LG/F NHL): progression free survival (PFS) after three years (median) follow-up.
Czuczman M.S., et al. *J. Clin. Oncol.* 17(1): 268-76, Jan. 1999. Treatment of patients with low-grade B-cell lymphoma with the combination of chimeric anti-CD20 monoclonal antibody and CHOP chemotherapy.
Czuczman M.S., et al., "IDEC-C2B8 (Rituximab) alone and in combination with CHOP in the treatment of low-grade B-cell lymphoma", Cancer Invest 16 (1 Suppl):21-22 (#17), 1998.
Czuczman M.S., et al., "IDEC-C2B8 and CHOP chemoimmunotherapy of low-grade lymphoma", Blood 86(10 suppl 1):55a (#206), Nov. 1995.
Czuczman M.S., et al., "IDEC-C2B8/CHOP Chemoimmunotherapy in Patients with Low-Grade Lymphoma: Clinical BCL-2 (PCR) Final Results", Nov. 1996, Blood 88, vol. 10, abstract 1799, pp. 453a, Nov. 1996.
Czuczman, M.S., et al., "Rituxan™/CHOP Chemo immunotherapy in patients with low-grade or follicular (LG/F) non-Hodgkin's lymphoma (NHL)", J Immunotherapy 20(5):401, Sep. 1997.
Czuczman, M.S., et al., "IDEC-C2B8 clears bcl-2 (t14;18) in patients (pts) with relapsed low grade or follicular lymphoma (LG/F NHL)", Proc Annu Meet Am Assoc Cancer Res 38:84 (#565), Mar. 1997.
Czuczman, M.S., et al., "Phase II Clinical Trial of IDEC-C2B8/CHOP Combination Therapy in Low Grade Lymphoma: Preliminary Results", Proc Am Soc Clin Oncol 14:401 (#1261), Mar. 1995.
Czuczman, M.S., et al., "The Anti-CD20 Antibody (MAB) IDEC-C2B8 Clears Lymphoma Cells Bearing the t(14;18) Translocation (bcl-2) from the Peripheral Blood (PB) and Bone Marrow (BM) of a Proportion of Patients (PTS) with Low-Grade or Follicular (LG/F) Non-Hodgkin's Lymphoma (NHL)", J. Ann Oncol 7(5 Suppl):111 (#532P), Nov. 1996.
Czuczman, Myron, "IDEC-C2B8/CHOP Chemoiivimunotherapy in Patients With Low-Grade Lymphoma: Clinical and BCL-2 (PCR) Final Results" presentation at the 38th Annual Meeting of the American Society of Hematology in Orlando, Florida, Dec. 610, 1996, pp. 1-15 (Exhibit D).
Dallaire, B.K., et al., "IDEC-C2B8 (RITUXIMAB): Biology and preclinical studies", J Mol Med, Jul. 1997, vol. 75, No. 7, abstract #256, pp. B230-B231.
Dana, et al., "Long-Tenn Follow-Up of Patients With Low-Grade Malignant Lymphomas Treated With Doxorubicin-Based Chemotherapy or Chemoimmunotherapy" *J. Clinical Oncology*, vol. 11, No. 4 (Apr.) 1993, pp. 644-651.
Dana et. al., "A Randomized Study of Alpha-Interferon Consolidation in Patients with Low-Grade Lymphoma Who Have Responded to Pro-Mace-Mopp (Day 1-8) (SWOG 8809)", Proceedings of ASCO, May 16-19, 1998, vol. 17, Abstract 10, p. 3a.
Davis, et al., "Retreatments with Rituxan (rituximab, IDEC-C2B8) have significant efficacy, do not cause HAMA, and are a viable minimally toxic alternative in relapsed or refractory non-Hodgkin's lymphoma (abstract)," *Blood* 90(10 Suppl. 1 Part 1): 509a (1997).

(56) References Cited

OTHER PUBLICATIONS

Davis, et al., "Rituximab Anti-CD20 Monoclonal Antibody Therapy in Non-Hodgkin's Lymphoma: Safety and Efficacy of Re-Treatment," *J. Clin. Oncol.* 18: 3135-3143 (2000).
Davis, et al., "Anti-Idiotype Antibodies Can Induce Long-Term Complete Remissions in Non-Hodgkin's Lymphoma Without Eradicating the Malignant Clone", *Blood*, vol. 92, No. 4 (Aug. 15), 1998: pp. 1184-1190.
Davis T., et al. *Blood* 90(10 Suppl. 1): 509a, abst No. 2269, Nov. 1997. Retreatments with RITUXAN™ (Rituximab, Idec-C2B8) have significant efficacy, do not cause HAMA, and are a viable minimally toxic alternative in relapsed or refractory non-Hodgkin's lymphoma (NHL).
Davis T., et al.. *Proc. Amer. Soc. Clin. Oncol.* 17: abst. No. 39, May 1998. Combination immunotherapy of low grade or follicular (LG/F) non-Hodgkin's lymphoma (NHL) with rituximab and alpha interferon: interim analysis.
Davis T. A., et al. Blood 86(10 Suppl. 1): 273a, abst. No. 1080, 1995. Yttrium labeled antiCD20 therapy for recurrent B cell lymphoma.
Davis T. A., et al. *Blood* 92(10 Suppl. 1): 414a, abst. No. 1710, Nov. 1998. Rituximab: phase II (PII) retreatment (ReRx) study in patients (PTS) with low grade or follicular (LG/F) NHL.
Davis T. A., et al. *Blood* 92(10 Suppl. 1): 414a, abst. No. 1711, Nov. 1998. Rituximab: first report of a phase II (PII) trial in NHL patients (PTS) with bulky disease.
Davis T. A., et al. *Clin. Cancer Res.* 5(3): 611-15, 1999. Therapy of B-cell lymphoma with anti-CD20 antibodies can result in the loss of CD20 antigen expression.
Davis T. A., et al. *I Clin. Oncol.* 17(6): 1851-57, 1999. Single-agent monoclonal antibody efficacy in bulky non-Hodgkin's lymphoma: results of a phase II trial of rituximab.
Davis T. A., et al. *Proc. Amer. Assn. Cancer Res.* 39: 435, abst. No. 2964, 1998. Therapy of B cell lymphoma with anti-CD20 can result in relapse with loss of CD20 expression.
DECISION Institution of Inter Partes Review, IPR2015-00418 re: U.S. Pat. No. 8,329,172 (U.S. Appl. No. 11/840,956, Antonio J. Grillo-Lopez, "Combination Therapies for B-Cell Lymphomas Comprising Administration of Anti-Cd20 Antibody"), entered Jul. 13, 2015 (35 pages).
DECISION Institution of Inter Partes Review (Paper 12), IPR2017-01094 re: U.S. Pat. No. 8,557,244 (White, et al., "Treatment of Aggressive Non-Hodgkin's Lymphoma with Anti-CD20 Antibody"), entered Oct. 2, 2017 (18 pages).
DECISION Institution of Inter Partes Review (Paper 6), IPR2017-01168 re: U.S. Pat. No. 8,821,873 (White, et al., "Treatment of Diffuse Large Cell Lymphoma with Anti-CD20 Antibody"), entered Nov. 6, 2017 (14 pages).
DECISION Institution of Inter Partes Review (Paper 8), IPR2017-01167 re: U.S. Pat. No. 8,557,244 (White, et al., "Treatment of Aggressive Non-Hodgkin's Lymphoma With Anti-Cd20 Antibody"), entered Nov. 6, 2017 (14 pages).
DECISION Institution of Inter Partes Review (Paper 9), IPR2017-01166 re: U.S. Pat. No. 8,329,172, (Grillo-Lopez, "Combination Therapies for B-Cell Lymphomas Comprising Administration of Anti-CD20 Antibody"), entered Nov. 13, 2017 (30 pages).
DECISION Institution of Inter Partes Review (Paper No. 12), IPR2017-01093 re: U.S. Pat. No. 8,329,172 (Grillo-Lopez, "Combination Therapies for B-Cell Lymphomas Comprising Administration of Anti-CD20 Antibody"), entered Oct. 6, 2017 (26 pages).
DECISION Institution of Inter Partes Review (Paper No. 12), IPR2017-01095 re: U.S. Pat. No. 9,296,821 (Grillo-Lopez, "Combination Therapies for B-Cell Lymphomas Comprising Administration of Anti-CD20 Antibodies"), entered Oct. 6, 2017 (35 pages).
Declaration of Christopher Butler re: ECOG Protocols Active as of May 19, 1998, signed on Oct. 11, 2016 (4 pages), (ECOG's Active Protocols: ECOG Protocols Active as of May 19, 1998, Internet Archive, Wayback Machine, http://web.archive.org/web/19980519084342/http://ecog.dfci.harvard.edu/~ecogdba/active_reports/Lymphoma.html; Revised: May 19, 1998; 1 page (Retrieved Mar. 4, 2013)).
Declaration of Dr. Izidore Lossos, dated Mar. 15, 2017 (62 pages) in Inter Partes Review No. IPR2017-01094 re: U.S. Pat. No. 8,557,244, White, et al., "Treatment of Aggressive Non-Hodgkin's Lymphoma with Anti-CD20 Antibody".
Declaration of Dr. Izidore Lossos, dated Mar. 15, 2017 (63 pages in Inter Partes Review No. IPR2017-01093 re: U.S. Pat. No. 8,329,172, Grillo-Lopez, "Combination Therapies for B-Cell Lymphomas Comprising Administration of Anti-CD20 Antibody".
Declaration of Dr. Izidore Lossos, dated Mar. 15, 2018 (82 pages) in Inter Partes Review No. IPR2017-01095 re: U.S. Pat. No. 9,296,821, Grillo-Lopez, "Combination Therapies for B-Cell Lymphomas Comprising Administration of Anti-CD20 Antibodies".
Declaration of Dr. Walter Longo, dated Mar. 3, 2017 (17 pages) in Inter Partes Review No. IPR2017-01093 re: U.S. Pat. No. 8,329,172, Grillo-Lopez, "Combination Therapies for B-Cell Lymphomas Comprising Administration of Anti-CD20 Antibody".
Declaration of Dr. Walter Longo, dated Mar. 3, 2017 (22 pages) in Inter Partes Review No. IPR2017-01094 re: U.S. Pat. No. 8,557,244, White, et al., "Treatment of Aggressive Non-Hodgkin's Lymphoma with Anti-CD20 Antibody".
Declaration of Dr. Walter Longo, dated Mar. 3, 2017 (22 pages) in Inter Partes Review No. IPR2017-01095 re: U.S. Pat. No. 9,296,821, Grillo-Lopez, "Combination Therapies for B-Cell Lymphomas Comprising Administration of Anti-CD20 Antibodies".
Declaration of Howard Ozer, M.D., Ph.D., dated Apr. 25, 2017 (91 pages) in Inter Partes Review No. IPR2017-01167 re: U.S. Pat. No. 8,577,244, White, et al., "Treatment of Aggressive Non-Hodgkin's Lymphoma with Anti-CD20 Antibody".
Declaration of Howard Ozer, M.D., Ph.D., dated Apr. 28, 2017 (95 pages) in Inter Partes Review No. IPR2017-01168 re: U.S. Pat. No. 8,821,873, White, et al., "Treatment of Diffuse Large Cell Lymphoma with Anti-CD20 Antibody".
Declaration of Howard Ozer, M.D., Ph.D., dated Apr. 3, 2017 (103 pages) in Inter Partes Review No. IPR2017-01166 re: U.S. Pat. No. 8,329,172, Grillo-Lopez, "Combination Therapies for B-Cell Lymphomas Comprising Administration of Anti-CD20 Antibody".
Declaration of Howard Ozer, M.D., Ph.D., dated Dec. 1, 2017 (110 pages) in Inter Partes Review No. IPR2018-00186 re: U.S. Pat. No. 9,296,821, Grillo-Lopez, "Combination Therapies for B-Cell Lymphomas Comprising Administration of Anti-CD20 Antibodies".
Declaration of Howard Ozer, M.D., Ph.D., dated Dec. 1, 2017 (114 pages) in Inter Partes Review No. IPR2018-00231 re: U.S. Pat. No. 9,504,744, White, et al., "Treatment of Diffuse Large-Cell Lymphoma with Anti-CD20 Antibody".
Declaration of Mark "Kip" Benyunes, dated Jun. 2, 2011 (7 pages) in Inter Partes Review No. IPR2017-01166 re: U.S. Pat. No. 8,329,172, Grillo-Lopez, "Combination Therapies for B-Cell Lymphomas Comprising Administration of Anti-CD20 Antibody".
Declaration of Michael J. Grossbard, M.D., in Support of the Petition for Inter Partes Review of U.S. Pat. No. 8,329,172 (U.S. Appl. No. 11/840,956, Antonio Grillo-Lopez, filed Aug. 18, 2007), dated Dec. 5, 2014 pp. 1-107.
Declaration of Prof Dr. M. H. J Van Oers, in European Patent No. EP 15150112.9, dated Jul. 5, 2017 (5 pages).
Declaration of Scott Bennett, Ph.D., dated Apr. 26, 2017 (169 pages) in Inter Partes Review No. IPR2017-01167 re: U.S. Pat. No. 8,577,244, White, et al., "Treatment of Aggressive Non-Hodgkin's Lymphoma with Anti-CD20 Antibody".
Declaration of Scott Bennett, Ph.D., dated Apr. 27, 2017 (196 pages) in Inter Partes Review No. IPR2017-01168 re: U.S. Pat. No. 8,821,873, White, et al., "Treatment of Diffuse Large Cell Lymphoma with Anti-CD20 Antibody".
Declaration of Scott Bennett, Ph.D., dated Apr. 6, 2017 (70 pages) in Inter Partes Review No. IPR2017-01166 re: U.S. Pat. No. 8,329,172 , Grillo-Lopez, "Combination Therapies for B-Cell Lymphomas Comprising Administration of Anti-CD20 Antibody".
Declaration of Scott Bennett, Ph.D., dated Nov. 28, 2017 (30 pages) in Inter Partes Review No. IPR2018-00231 re: U.S. Pat. No. 9,504,744, White, et al., "Treatment of Diffuse Large-Cell Lymphoma with Anti-CD20 Antibody".

(56) References Cited

OTHER PUBLICATIONS

Declaration of Steiner Aamdal, Professor Emeritus in Oslo District Court, case No. 16-206868TVI-OTIR dated Nov. 13, 2017, pp. 1-18.
Declaration of Sylvia D. Hall-Ellis, Ph.D., dated Nov. 27, 2017 (124 pages) in Inter Partes Review No. IPR2018-00186 re: U.S. Pat. No. 9,296,821, Grillo-Lopez, "Combination Therapies for B-Cell Lymphomas Comprising Administration of Anti-CD20 Antibodies".
Definition of consolidation Therapy, NCI Dictionary of Cancer Terms—National Cancer Institute, http://www.cancer.gov/publicications/dictionaries/cancer-terms?CdrID=45654, retrieved Oct. 9, 2017 (1 page).
Definition of Maintenance Therapy, NCI Dictionary of Cancer Terms—National Cancer Institute, http://www.cancer.gov/publicications/dictionaries/cancer-terms?CdrID=45768, retrieved Nov. 17, 2015 (1 page).
Demidem A., et al. *Cancer Biother. Radiopharm.* 12(3): 177-86, 1997. Chimeric anti-CD20 (IDEC-C2B8) monoclonal antibody sensitizes a B cell lymphoma cell line to cell killing by cytotoxic drugs.
Demidem, et al., Chimeric anti-CD20 antibody (IDEC-C2B8) is apoptotic and sensitizes drug resistant human B cell lymphomas and AIDS related lymphomas to the cytotoxic effect of CDDP, VP-16 and toxins *FASEB J9(3):A206*, Abstract #1197, 1995.
DeNardo G.L., et al. *Cancer Res.* 50(3 Suppl.): 1014s-1016s, 1990. Fractionated radioimmunotherapy of B-cell malignancies with $^{131}$I-Lym-1.
DeNardo G.L., et al. *I.J. Rad. Oncol. Biol.Phys.* 11(2): 335-48, 1985. Requirements for a treatment plan in system for radioimmunotherapy.
DeNardo S.J., et al. *Antibody Immunoconj. Radiopharm.* 1(1): 17-33, 1988. Pilot studies of radioimmunotherapy of B cell lymphoma and leukemia using 1-131 Lym-1 monoclonal antibody.
DeNardo S.J., et al. *Cancer* 73(3 Suppl.): 1023-32, 1994. The biologic window for chimeric L6 radioimmunotherapy.
DeNardo, et al., "A Revolution in the treatment of Non-Hodgkin's Lymphoma," Cancer Biotherapy and Radiopharmaceuticals 1998, 13(4):213-223.
DeVita, et al., "Chapter 44: Hodgkin's Disease and the Non-Hodgkin's Lymphomas," in Cancer: Principles & Practice of Oncology, Second Edition, eds. DeVita, Hellman, and Rosenberg, 1985, pp. 1623-1709.
Di Gaetano N., et al. *Br. I Haematol.* 114(4): 800-09, 2001. Synergism between fludarabine and rituximab revealed in a follicular lymphoma cell line resistant to the cytotoxic activity of either drug alone.
Dickson S. *Gen. Engr. News* 5(3): 1, Mar. 1985. Scientists produce chimeric monoclonal Abs.
Dillman R. O. I Clin. OncoL 12(7): 1497-1515, 1994. Antibodies as cytotoxic therapy.
Dillman RO, et al., "Therapy of chronic lymphocytic leukemia and cutaneous T-cell lymphoma with T101 monoclonal antibody." J Clin Oncol, 1984, vol. 2, pp. 881-891.
Dillman, "Monoclonal Antibodies for Treating Cancer," Annals of Internal Medicine 1989, 111:592-603.
Dixon, et al., "Effect of Age on Therapeutic Outcome in Advanced Diffuse Histiocytic Lymphoma: The Southwest Oncology Group Experience," Mar. 1986, vol. 4, No. 3, pp. 295-305.
Documents from European Oppositions pertaining to EP Application No. 08005921.5 (Antonio Grillo-Lopez, filed Aug. 11, 1999) (Patent No. EP 1974747), available at http://register.epo.org/application?number=EP08005921&lng-en&tab=doclist pp. 1-52.
Dudeja, et al., "Synergy of Water Soluable Prodrug Triptolide (minnelide) with Gemcitabine and Nab-paclitaxel in Pancreatic Cancer," Journal of Clinical Oncology 2016, vol. 34, No. 4_suppl., p. 259.
E1496 Forms Packet, initially dated Mar. 1993, last revised Jul. 2005, (1 page).
E1496 Protocol Accrual on Study Dates, dated Aug. 23, 2016 (4 pages).

Eary J.F., et al. *J Nucl. Med.* 31(8): 1257-68, 1990. Imaging and treatment of B-cell lymphoma.
ECOG E1496 Trial Results "Non-Progressing Low-grade NHL after CVP—RITUXAN® (Rituximab)", Study date Mar. 9, 2009, pp. 1-7, (Retrieved Dec. 2, 2010) http://www.rituxan.com/lymphoma/hcp/indications/E1496/index.m.
ECOG E1496, Activation of Protocol E1496, Randomized Phase III Study in Low Grade Lymphoma Comparing Cyclophosphamide/Fludarabine to Standard Therapy Followed by Maintenance Anti-CD20 Antibody, Activation Date: Mar. 19, 1998 pp. 1-47.
ECOG E4494 Protocol Accrual on Study Dates, dated Aug. 23, 2016 (3 pages).
ECOG E4494, Activation of Protocol E4494, A Phase III Trial of CHOP versus CHOP and Chimeric Anti-CD20 Monoclonal Antibody (IDEC-C2B8) in Older Patients with Diffuse Mixed, Diffuse Large Cell and Immunoblastic Large Cell Histology Non-Hodgkin's Lymphoma, Activation Date: Dec. 12, 1997 pp. 1-61.
ECOG Institutions by Name, http://web.archive.org/web/19980519084032/http://ecog.dfci.harvard.edu/~ecogdba/general/insts_byname.html (archived May 19, 1998) pp. 1-10 (retrieved Dec. 4, 2014).
ECOG's Active Protocols: ECOG Protocols Active as of May 19, 1998, Internet Archive, Wayback Machine, http://web.archive.org/web/19980519084342/http://ecog.dfci.harvard.edu/~ecogdba/active_reports/Lymphoma.html; Revised: May 19, 1998; 1 page (Retrieved Mar. 4, 2013).
Einfeld D.A., et al. *EMBO J.* 7: 711-17, 1988. Molecular cloning of the human B cell CD20 receptor predicts a hydrophobic protein with multiple transmembrane domains.
Eisenbeis C.F., et al. *Clin. Cancer Res.* 10: 6101-10, 2004. Combination immunotherapy of B-cell non-Hodgkin's lymphoma with rituximab and interleukin-2: a preclinical and phase I study.
Electronic Data Gathering, Analysis, and Retrieval (EDGAR): EDGAR filer manual: Guide for electronic filing with the U.S. Securities and Exchange Commission; Release 5.10, Sep. 1996 [excerpts] (21 pages).
Endo K. *Jpn. J Cancer Chemother.* 26: 744-48, 1999. Current status of nuclear medicine in Japan.
Engert A., et al. *Ann. Hematol.* 77(suppl. 2): S180, abst. No. 717, 1998. Multicenter phase II study of the monoclonal anti-CD20 antibody rituximab (IDEC-C2B8) in patients with inteimediate/high grade non-Hodgkin's lymphoma.
Expert Report of Professor Marinus H. J. Van Oers in Oslo District Court, Case No. 16-206868TV1-OTIR/05, dated Nov. 27, 2017, pp. 1-17.
Ezdinili, et al., "The Effect of Intensive Intermittent Maintenance Therapy in Advanced Low-Grade Non-Hodgkin's Lymphoma," Cancer 1987, 60:156-216.
FDA Clinical Review of Rituximab dated Sep. 29, 2006, pp. 1-110.
FDA FOIA Response Letter, dated Aug. 26, 2016, (3 pages).
FDA label of Doxorubicin Hydrochloride for injection USP, pp. 1-22, 2010.
Federico, et al., "R-CVP Versus R-CHOP Versus R-FM for the Initial Treatment of Ptients with Advanced-Stage Follicular Lymphoma: Results of the FOLL05 Trial Conducted by the Fondazione Italiana Linformi," Journal of Clinical Oncology 2013, 31(12):1506-1513.
Feenstra, et al., "Drug-Induced Heart Failure," Journal of the American College of Cardiology 1999, vol. 33, No. 5, pp. 1152-1162.
Feugier, et al., "Long-Term Results of the R-CHOP Study in the Treatment of Elderly Patients With Diffuse Large B-Cell Lymphoma: A Study by the Groupe d'Etude des Lymphomes de l'Adult"; Journal of Clinical Oncology, vol. 23, No. 18, Jun. 20, 2005, pp. 4117-4126.
Feugier, "A Review of rituximab, the first anti-CD20 monoclonal antibody used in the treatment of B non-Hodgkin's lymphomas," Future Oncology 2015, 11(9):1327-1342.
Fisher D.C.; et al. *Blood* 92: 247a, abst. No. 1010, 1998. Phase 1 trial with CD40-activated follicular lymphoma cells: a novel cellular vaccine strategy for B cell malignancies.
Fisher, et al., "Comparison of a Standard Regimen (CHOP) with Three Intensive Chemotherapy Regimens for Advanced Non-

(56) References Cited

OTHER PUBLICATIONS

Hodgkin's' Lymphoma," New England Journal of Medicine, Apr. 1993, vol. 328, No. 14, pp. 1002-1006.
Flinn I. W., et al. *Blood* 92(10 Suppl. 1): 648a, abst. No. 2678, Nov. 1998. In vivo purging and adjuvant immunotherapy with rituximab during PBSC transplant for NHM [sic].
Flinn, I. W., et al., "Immunotherapy with rituximab during peripheral blood stem cell transplantation for non-Hodgkin's lymphoma." Biol Blood Marrow Transplant. 2000;6(6):628-32.
Foon et. al., "Lymphomas", Williams Hematology, 5$^{th}$ edition, Ch. 111, Part ix, Beutler, Lichtman, Coller, & Kipps, McGraw-Hill, Inc., 1995, pp. 1076-1096.
Foon KA, et al., "Effects of monoclonal antibody therapy in patients with chronic lymphocytic leukemia." Blood, 1984, vol. 64, pp. 1085-1093.
Foon KA, "Laboratory and Clinical Applications of Monoclonal Antibodies for Leukemias and Non-Hodgkin's Lymphomas." Curr. Probl. Cancer 13(2): 57-128 (Mar/Apr. 1989).
Foran J. M., et al. *Br. I Haematol.* 102(1): 149, 1998 Immunotherapy of mantle cell lymphoma (MCL), lymphoplasmacytoid lymphoma (LPC) and Waldentrom's macroglobulinemia (WM), and small lymphocytic leukemia (SLL) with rituximab (IDECC2B8): preliminary results of an ongoing international multicentre trial.
Foran J. M., et al., "European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma", J Clin Oncol., Jan. 2000, vol. 18, No. 2, pp. 317-324.
Foran, et al., "Immunotherapy of recurrent follicular lymphoma (FL) with Rituximab (IDECCB8): Preliminary results of an ongoing UK multicentre trial," British Journal of Hematology, vol. 102, No. 1, p. 243, (1998).
Ford B. *The Cal-Gab: Quarterly Newsletter of the Cancer and Leukemia Group B* 7(1): 4-5, Spring 1998. Rituxan™ (Rituximab).
Ford S. M., et al. *Highlights in Oncology Practice* 16(2): 40-50, 1998. Immunotherapeutic approaches to treatment of B-cell neoplasms: focus on unconjugated antibodies.
Forstpointner, et al., "Maintenance therapy with rituximab leads to a significant prolongation of response duration after salvage therapy with a combination of rituximab, fludarabine, cyclophosphamide, and mitoxantrone (R-FCM) in patients with recurring and refractory follicular and mantle cell lymphomas: results of a prospective randomized study of the German Low Grade Lymphoma Study Group (GLSG)," Blood, 2006, vol. 108, No. 13, pp. 4003-4008.
Freedman A.S., et al., "Autologous bone marrow transplantation in B-cell non-Hodgkin's lymphoma: very low treatment-related mortality in 100 patients in sensitive relapse", J. Clin Oncol., May 1990, vol. 8, No. 5, pp. 784-791.
Freedman, et al., "High-Dose Therapy and autologous Bone Marrow Transplantation in Patients with Follicular Lymphoma During First Remission," Blood, 1996, vol. 88, No. 7, pp. 2780-2786.
Fridik M.A., et al. *Ann. Hematol.* 74(1): 7-10, 1997. First-line treatment of Waldenstrom's disease with cladribine.
Friedberg J. W., et al. *Expert Rev. Anticancer Ther.* 4(1): 18-26, 2004. Iodine-131 tositumomab (Bexxaro): radioimmunoconjugate therapy for indolent and transformed B-cell non-Hodgkin's lymphoma.
Full prescribing infoonation for Rituxan (rituximab). Revised Feb. 2010, pp. 1-35.
Gallagher CJ, et al., "Follicular lymphoma: Prognostic factors for response and survival.", 1986, J Clin Oncol, vol. 4, pp. 1470-1480.
Gallmeier, et al., "Inhibition of Ataxia Telangiectasia- and Rad3-Related Function Abrogates the In Vitro and In Vivo Tumorigenicity of Human Colon Cancer Cells Through Depeletion of CD133+ Tumor-Initiating Cell Fraction," Stem Cells, 2011, 39:418-429.
Garcia-Conde J., et al. "Study to Evaluate the Efficacy and Safety of Rituximab (IDEC-C2B8) and CVP Chemotherapy in Low-Grade or Follicular B-Cell Lymphoma After Relapse. Preliminary Results At a Follow Up Period of 3 Months," Blood, vol. 94, No. 10 Suppl. 1 Part 2, p. 261 b Nov. 15, 1999.

Ghielmini, et al., "Prolonged treatment with rituximab in patients with follicular lymphoma significantly increases event-free survival and response duration compared with the standard weekly X4 schedule", Blood, 2004, vol. 103, No. 12, pp. 4416-4423.
Gianni A.M., et al. *Blood* 102: 749-55, 2003. Long-term remission in mantle cell lymphoma following high-dose sequential chemotherapy and in vivo rituximab-purged stem cell autografting (R-HDS regimen).
Ginaldi L., et al. *I Clin. Pathol.* 51: 364-69, 1998. Levels of expression of CD19 and CD20 in chronic B Leukemias.
Gisselbrecht et. al., "Treatment of low-grade non-Hodgkin's lymphomas", Non-Hodgkin's Lymphoma, Solal-Céligny, Brousse, Reyes, Gisselbrecht & Coiffier, Manson Publishing Ltd., 1993, pp. 317-336.
Gisselbrecht, et al., "Rituximab maintenance therapy after autologous stem-cell transplantation in patients with relapsed CD20(+) diffuse large B-cell lymphoma: final analysis of the collaborative trial in relapsed aggressive lymphoma", J. Clin. Oncol, Dec. 2012, vol. 30, No. 36, pp. 4462-4469.
Gladstone, D. E. et al., "High-dose cyclophosphamide and rituximab without stem cell transplant: a feasibility study for low grade B-cell, transformed and mantle cell lymphomas." Leuk Lymphoma. Nov. 2011; 52(11):2076-81.
Golay J., et al. *Haematologica* 88: 1002-12, 2003. Rituximab-mediated antibody-dependent cellular cytotoxicity against neoplastic B cells is stimulated strongly by interleukin-2.
Golay J. T., et al. *J. Immunol.* 135(6): 3795-801, 1985. The CD20 (Bp35) antigen is involved in activation of B cells from the G0 to the 01 phase of the cell cycle.
Goldenberg D. M., et al. *J. Clin. Oncol.* 9(4): 548-64, 1991. Imaging and therapy of gastrointestinal cancers with radiolabeled antibodies.
Goldenberg, et al., "Characterization of New, Chimeric and Humanized, Anti-CD20 Monoclonal Antibodies, cA20 and hA20, with Equivalent Efficacy to Rituximab In-Vitro and in Xenografted Human Non-Hodgkin's Lymphoma", Poster Session: Biologic Therapy of Lymphomas: Laboratory Investigations, 2004, 1 page.
Gonzalez-Barca, et al., "Low-dose subcutaneous interleukin-2 in patients with minimal residual lymphoid neoplasm disease," Eur. J. Hemat. 62(4): 231-238 (1999).
Gopal, et al., "Clinical applications of anti-CD20 antibodies", J. Lab Clin Med; 134:, 1999, pp. 445-450.
Gordon L. I., et al. *Blood* 94(10 Suppl. 1): 91a, abst. No. 396, 1999. ZEVALIN™ (IDEC Y2B8) radioimmunotherapy of rituximab refractory follicular non-Hodgkin's lymphoma (NHL): interim results.
Gordon L. I., et al. *I Immunother.* 22(5): 459, 1999. Update on IDEC-Y2B8 (ZEVALIN™) radioimmunotherapy of B-cell NHL.
Gordon, et al., "Comparison of a Second-Generation Combination Chemotherapeutic Regimen (m-BACOD) with a Standard Regimen (CHOP) for Advanced Diffuse Non-Hodgkin's Lymphoma," New Engl. J. Med. 1992, vol. 327, No. 19, pp. 1342-1349.
Gottlieb et al. "Chemotherapy of malignant lymphoma with adriamycin", Cancer Research 33:3024-3028 (Nov. 1973).
Greenberger J. S., et al. *Cancer Res.* 45(2): 758-67, 1985. Effects of monoclonal antibody and complement treatment of human marrow on hematopoiesis in continuous bone marrow culture.
Greiner J. W., et al. *Science* 235(4791): 895-98, 1987. Recombinant interferon enhances monoclonal antibody-targeting of carcinoma lesions in vivo.
Gribben J. G., et al. *N Engl. I Med.* 325(22): 1525-32, 1991. Immunologic purging of marrow assessed by PCR before autologous bone marrow transplantation for B-cell lymphoma.
Gribben J. G., et al., "Detection of residual lymphoma cells by polymerase chain reaction in peripheral blood is significantly less predictive for relapse than detection in bone marrow." Blood, 1994, vol. 83, pp. 3800-3807.
Grillo-Lopez A.J., et al. *Ann. Oncol.* 7(3 Suppl.): 57, abst. No. 195, 1996. Treatment (rx) of relapsed non-Hodgkin's lymphoma (NHL) using the 90-yttrium (90-Y) labeled anti-CD20 monoclonal antibody (MAB) IDEC-Y2B8: a phase I clinical trial (PI CT).
Grillo-Lopez A.J., et al. *Antibody Immunoconj. Radiopharm.* 8: 60, abst. No. 10, 1995. Treatment options for patients with relapsed low-grade or follicular lymphoma: the role of IDEC-C2B8.

(56) References Cited

OTHER PUBLICATIONS

Grillo-Lopez A.J., et al. *Blood* 86(10 Suppl. 1): 55a, abst. No. 207, 1995. Phase I study of IDEC-Y2B8: 90-yttrium labeled anti-CD20 monoclonal antibody therapy of relapsed non-Hodgkin's lymphoma.
Grillo-Lopez A.J., et al. *Br. J. Haematol.* 93(Suppl. 2): 283, abst. No. 1072, 1996. IDECC2B8 chimeric anti-CD20 antibody (MAB): safety and clinical activity in the treatment of patients (PTS) with relapsed low-grade or follicular (IWF:A-D) non-Hodgkin's lymphoma (NHL).
Grillo-Lopez A.J. IBC Int'l. Conference on Antibody Engineering, La Jolla, Dec. 1994. IDEC-C2B8 chimeric antibody and IDEC-Y2B8 radiolabeled antibody phase I and II studies in patients with non-Hodgkin's lymphoma (abstract of presentation).
Grillo-López, A.J., et al., Anti-CD20 Chimeric Antibody, IDEC-C2B8: Safety and Clinical Activity in the Treatment of Relapsed Low Grade or Follicular (IWF: A-D) Lymphomas (LG-F/NHL), 25th Annual Meeting of the International Society for Experimental Hematology, Exp Hematol Abstract 691, vol. 24, No. 9, Aug. 1996, pp. 1150.
Grillo-López, A.J., et al., "Development of Response Criteria (RC) for Low-Grade or Follicular Lymphomas (LG/F NHL) and Application in a 166 Patient Study", 26th Annual Meeting of the International Society for Experimental Hematology, Exp Hematol, Aug. 1997, vol. 25, No. 8, Abstract 17, p. 732.
Grillo-López, A.J., et al., "IDEC-C2B8 (RITUXIMAB): Clinical Activity in Poor Prognosis Subgroups of Relapsed Low-Grade or Follicular Lymphoma", 26th Annual Meeting of the International Society for Experimental Hematology, Exp Hematol Abstract 406, vol. 25, No. 8, Aug. 1997, pp. 846.
Grillo-López, A.J., et al., "IDEC-C2B8: Clinical development of a chimeric anti-CD20 antibody for the treatment of patients (pts) with relapsed low-grade or follicular NHL", Abstract 190, Ann Oncol 7(1 Suppl):56, Mar. 1996.
Grillo-López, et al., "Monoclonal Anti-CD20 Antibody (IDEC-C2B8) Therapy of B-Cell Non-Hodgkin's Lymphoma—Pre Clinical Development and Early Clinical Results", Proc Eighth Nci/Eortc Symposium on New Drugs in Cancer Therapy, p. 112 (#175) Mar. 1994.
Grillo-López, et al., "Overview of the Clinical Development of Rituximab: First Monoclonal Antibody Approved for the Treatment of Lymphoma", Seminars in Oncology, vol. 26, No. 5, Suppl 14 (Oct. 1999); pp. 66-73.
Grillo-López, et al., "Overview of the safety and efficacy of IDEC-C2B8 including activity in patient populations with poor prognosis low grade or follicular NHL, (LG/F NHL)", J. Mol. Med. Abstract 259, vol. 75, No. 7, Jul. 1997, pp. B231-B232.
Grillo-López, et al., "Preclinical and Early Clinical Development of the Anti-CD20 Monoclonal Antibody IDEC-C2B8", Ninth International Conference on Monoclonal Antibody Immunoconjugates for Cancer, Antibody Immunoconjugates, and Radiopharmaceuticals, vol. 7, No. 1, Abstract 64, Spring 1994.
Grillo-López, et al., "Response criteria (RC) for NHL: Importance of "normal" lymph node (LN) size and correlations with response." Blood 92(10 Suppl 1):412a (#1701), Nov. 1998.
Grillo-López, et al., "Rituxan™: Anti CD20 monoclonal antibody for the treatment of lymphoma." Exp Hematol 26(8):746 (#233), Aug. 1998.
Grillo-López, "IDEC-C2B8: Initial Phase II Results in Patients with B-Cell Lymphoma", Journal of Immunotherapy with Emphasis on Tumor Immunology, vol. 16, No. 3, Oct. 1994, pp. 236.
Grillo-López, "Rituximab (IDEC-C2B8): Development of an anti-CD20 monoclonal antibody (MAB) for the treatment of non-Hodgkin's lymphoma." Ann Hematol 77(Suppl 1):A7 (#26), 1998.
Grillo-López, "Rituximab: An Insider's Historical Perspective", Seminars in Oncology, vol. 27, No. 6, Suppl 12 (Dec. 2000); pp. 9-16.
Grillo-López, et al., "Clinical activity of the monoclonal antibody (MAB) IDEC-C2B8 in patients (pts) with relapsed low-grade or follicular NHL (R-LG/F NHL)", Eur J Cancer 33(S8):S260-S261 (#1179), Sep. 1997.
Grillo-López, AJ "The First Antibody Therapy for Cancer: a Personal Experience", Expert Review of Anticancer Therapy Retrospective, 2013, vol. 13, No. 4, pp. 399-406.
Grillo-Lopez, et al., "IDEC-C2B8 Rituxan (rituximab)" presentation at Biological Response Modifiers Committee Review in Bethesda, Maryland, Jul. 25, 1997, pp. 1-77 (Exhibit A).
Grossbard M. L. "The McLaughlin et al Article Reviewed", Dec. 1998, Oncology, pp. 1769-1770.
Grossbard M. L. and Multani, P.S., "Clinical Status and Optimal Use of Rituximab for B-Cell Lymphomas", *Oncology* vol. 12(12); 1998, pp. 1-2, as published online by www.cancernetwork.com.
Grossbard M. L., et al. *Blood* 80(4): 863-78, 1992. Monoclonal antibody-based therapies of leukemia and lymphoma.
Grossbard, et al., "Clinical Status and Optimal Use of Rituximab for B-Cell Lymphomas," Published on Psychiatric Times, www.psychiatrictimes.com, Review Article, Dec. 1, 1998, pp. 1-3.
Guan, et al., "Rituximab in combination with CHOP, an effective and well-tolerated salvage regimen for diffuse large B-Cell Lymphoma", Chinese Journal of Clinical Oncology, vol. 4, No. 4, pp. 264-267, (2007).
Gupta and Lister, "Current Management of Follicular Lymphoma", Current Opinion in Oncology, 1996, vol. 8, pp. 360-365.
Gura T. *Science* 278: 1041-42, 1997. Systems for identifying new drugs are often faulty.
Habeiniann, et al., "Rituximab-CHOP versus CHOP alone or with maintenance rituximab in older patients with diffuse large B-cell lymphoma", [PUBMED Abstract] *J Clin Oncol* 24 (19): 3121-7, 2006.
Habermann, et al., "Rituximab-CHOP versus CHOP with or without maintenance rituximab in patients 60 years of age or older with diffuse large B-cell lymphoma (DLBCL): an update" [Abstract] *Blood* 104 (11): A-127, 2004.
Hagenbeek A., et al. *I Clin. Oncol.* 16(1): 41-47, 1998. Maintenance of remission with human recombinant interferon alfa-2a in patients with stages III and IV low-grade malignant non-Hodgkin's lymphoma. European Organization for Research and Treatment of Cancer Lymphoma Cooperative Group.
Hainsworth et al. "Rituximab as First-Line and Maintenance Therapy for Patients With Indolent Non-Hodgkin's Lymphoma", J. Clinical Oncology, 2002, vol. 20, pp. 4261-4267.
Hainsworth, et al., "Rituximab Induction and Maintenance Therapy in Patients (pts) with Previously Untreated Low-Grade Non-Hodgkin's Lymphoma (NHL): Preliminary Results of a Minnie Pearl Cancer Research Network Phase II Trial" *Proceedings of the ASCO*, vol. 18 (Abstract #105) 1999, p. 29a ; with e-mail from Ascopubs [ascobus@asco.org] dated Mar. 11, 2013, 1 pg., stating that the 1999 Program Proceedings vol. 18 was made available to the public on May 15, 1999.
Hainsworth J.D., et al. *Blood* 95: 3052-56, 2000. Rituximab monoclonal antibody as initial systemic therapy for patients with low-grade non-Hodgkin lymphoma.
Hainsworth, et al., "Maximizing Therapeutic Benefit of Rituximab: Maintenance Therapy Versus Re-Treatment at Progression in Patients with Indolent Non-Hodgkin's Lymphoma—A Randomized Phase II Trial of the Minnie Pearl Cancer Research Network," Journal of Clinical Oncology, 2005, vol. 23, No. 6, pp. 1088-1095.
Haioun, et al., "Survival Benefit of High-Dose Therapy in Poor-Risk Aggressive Non-Hodgkin's LymphomaL Final Analysis of the Prospective LNH87-2 Protocol—A Groupe d'Etude. des Lymphomes de l'Adute Study," Aug. 2000, vol. 18, No. 16, pp. 3025-3030.
Hall, et al., "Mechanisms of Action of, and Modes of Resistance to, Alkylating Agents Used in the Treatment of Haematological Malignancies," Blood Reviews, 1992, No. 6, pp. 163-173.
Hancock, et al., "A monoclonal antibody against the c-erbB-2 protein enhances the cytotoxicity of cis-diamrninedichloroplatinum against human breast and ovarian tumor cell lines," *Cancer Res.* 51(17): 4575-80 (1991).
Haq, et al., "Doxorubicin-Induced Congestive Heart Failure in Adults," Cancer 1985, vol. 56, No. 6, pp. 1361-1365.

(56) References Cited

OTHER PUBLICATIONS

Harris N. L., et al. *Blood* 54(5): 1361-92, 1994. A revised European-American classification of lymphoid neoplasms: a proposal from the International Lymphoma Study Group.
Harris N. L., et al. *J Clin. Oncol.* 17(12): 3835-49, 1999. World Health Organization classification of neoplastic diseases of the hematopoietic and lymphoid tissues: report of the Clinical Advisory Committee meeting—Airlie House, Virginia, Nov. 1997.
Hartwell L. H., et al. *Science* 278: 1064-68, 1997. Integrating genetic approaches into the discovery of anticancer drugs.
Haskell, et al., Chapter 89: Intermediate-And High Grade Lymphomas in Cancer Treatment, 4th Edition, W. B. Saunders Company, Ed. Jonathan Berek, 1995, pp. 1014-1016.
Hekman A., et al. *Ann. Rept. Netherlands Cancer Inst., Amsterdam*, pp. 47-48, 1993. Immunotherapy.
Herold M., et al. *Ann. Hematol.* 79: 332-335, 2000. Successful treatment and re-treatment of resistant B-cell chronic lymphocytic leukemia with the monoclonal anti-CD20 antibody rituximab.
Hickish, et al., "Molecular monitoring of low grade non-Hodgkin's lymphoma by gene amplification", Br. J. Cancer, 1991, vol. 64, pp. 1161-1163.
Hiddemann, et al., "New Aspects in the Treatment of Advanced Low-Grade Non-Hodgkin's Lymphomas: Prednimustine/Mitoxantrone Versus Cyclophosphamide/Vincristine/Prednisone Followed by Interferon Alfa Versus Observation Only—A Preliminary Update of the German Low-Grade Lymphoma Study Group", Seminars in Hematology, 1994, vol. 31, No. 2, Suppl 3, pp. 32-35.
Hiddemann W., et al. *Blood* 88(11): 4085-89, 1996. Lymphoma classification—the gap between biology and clinical management is closing.
Hiddemann, "Non-Hodgkin's Lymphomas—Current Status of Therapy and Future Perspectives",*European Journal of Cancer* vol. 31A (13/14) 1995, pp. 2141-2145.
Hiddemann, et al. "Lymphomas: New Recognitions and Therapy Strategies", Ch. 11, C.H. Beck, Thieme Georg Verlag, 2005, pp. 78-81 (Translated).
Hiddemann, et al., "Frontline therapy with rituximab added to the combination f cyclophosphamide, doxorubicin, vincristine, and prednisone (CHOP) significantly improves the outcome for patients with advanced-stage follicular lymphoma compared with therapy with Chiop alone: results of a prospective randomized study of the German Low-Grade Lymphoma Study Group," Blood, 2005, vol. 106, No. 12, pp. 3725-3732.
Hillmen P., et al. *Semin. Oncol.* 31(1 suppl. 2): 22-26, 2004. Advancing therapy for chronic lymphocytic leukemia—the role of rituximab.
Hochster, et al., "Maintenance rituximab after cyclophosphamide, vincristine, and prednisone prolongs progression-free survival in advanced indolent lymphoma: Results of the randomized phase III ECOG 1496 Study," *J Clin. Oncol.* 27(10): 1607-1614 (2009).
Hochster, et al., "Maintenance Rituximab After CVP Results in Superior Clinical Outcome in Advanced Follicular Lymphoma (FL): Results of the E1496 Phase III Trial From the Eastern Cooperative Oncology Group and the Cancer and Leukemia Group B," *Blood*, vol. 106, No. 11, pt. 1, Nov. 1, 2005 (Nov. 1, 2005), p. 106A.
Hochster, et al., "Prolonged Time to Progression (TTP) in Patients With Low Grade Lymphoma (LGL) Treated With Cyclophosphamide (C) and Fludarabine (F) [ECOG 1491]," American Society of Clinical Oncology Program/Proceedings, Thirty Fourth Annual Meeting May 16-19, 1998, Los Angeles, California, vol. 17, Abstract 66, (5 pages).
Hochster, H. S., et al., "Results of E1496: A phase III trial of CVP with or without maintenance rituximab in advanced indolent lymphoma (NHL)", Journal of Clinical Oncology, 2004 ASCO Annual Meeting, vol. 22, No. 14S (Jul. 15 Supplemental), 2004: 6502, pp. 1-2.
Hoerni, et al., "Maintenance Immunotherapy with BCG in Non-Hodgkin's Malignant Lymphomas: a Progress Report of a Randomized Trial", Recent Results in Cancer Research, 1980, vol. 80, pp. 92-97.

Hoerni, et al., "Successful Maintenance Immunotherapy by BCG of Non-Hodgkin's Malignant Lymphomas: Results of a Controlled Trial", British J. Hematology, 1979, vol. 42, pp. 507-514.
Hooijberg E., et al. *Cancer Res.* 55: 2627-34, 1995. Eradication of large human B cell tumors in nude mice with unconjugated CD20 monoclonal antibodies and interleukin 2.
Hoppe, et al., "The Treatment of Advanced Stage Favorable Histology Non-Hodgkin's Lymphoma: A Preliminary Report of a Randomized Trial Comparing Single Agent Chemotherapy, Combination Chemotherapy, and Whole Body Irradiation," Blood 1981, vol. 58, No. 3, pp. 592-598.
Horning S., "Treatment Approaches to the Low-Grade Lymphomas," Blood 1994, vol. 83, No. 4, pp. 881-884.
Horning S.J., et al. *Blood* 100(11 part 1): 357a, abst. no. 1385, 2002. Rituximab treatment failures: tositumomab and Iodine I 131 tositumomab (Bexxar®) can produce meaningful durable responses.
Horning, "Natural History of and Therapy for Indolent Non-Hodgkin's Lymphomas," Seminars in Oncology, 1993, vol. 20, No. 5, Suppl. 5, pp. 75-88.
Horning, et al., "The natural history of initially untreated low-grade non-Hodgkin's lymphomas," N Engl J. Med, 1984, 311(23):1471-1475.
Horning, S., et al., "Response criteria (RC) and quality assurance (QA) of responses in the evaluation of new therapies for patients (pts) with low-grade lymphoma (LG NHL)", Proc Am Soc Clin Oncol 16:18a (#62), May 1997.
Houts, et al., "Nonmedical Costs to Patients and Their Families Associated with Outpatient Chemotherapy," Cancer 1984, 54:2388-2392.
Howard, et al., "Rituximab and CHOP Induction Therapy for Newly Diagnosed Mantle-Cell Lymphoma: Molecular Complete Responses are not Predictive of Progression-Free Survival," Journal of Clinical Oncology, 2002, vol. 20, No. 5, pp. 1288-1294.
Hultin, et al., "CD20 (pan-B cell) antigen is expressed at a low level on a subpopulation of human T lymphocytes", Cytometry 14(2), 1993, pp. 196-204 (Abstract only), www.ncbi.nlm.nih.gov/pubmed/7679964.
Hurwitz E, et al., "A Synergistic Effect Between Anti-Idiotype Antibodies and Antineoplastic Drugs in The Therapy of A Murine B-Cell Tumor." Intl. J. Cancer 37(5): 739-45 (May 1986).
IDEC and Genentech joint press release, "IDEC Pharmaceuticals and Genentech Announce Positive Final Results", Dec. 9, 1996, pp. 1-5.
IDEC Pharmaceuticals Corp. and Genentech, Inc., Product insert for Rituxan® approved by U.S. Food and Drug Administration on Nov. 26, 1997.
IDEC Phamiaceuticals Corp., press release dated Dec. 9, 1996. IDEC Pharmaceuticals and Genentech announce positive final results for pivotal phase III trial of IDEC-C2B8 as single agent.
IDEC Pharmaceuticals Corp., U.S. Securities and Exchange Commission Form S-1 Registration Statement, 1991.
IDEC Pharmaceuticals Corporation, Clinical Study Report: 102-01-04, "Pivotal Phase III Multi-Center Study to Evaluate the Safety and Efficacy of Once Weekly Times Four Dosing of IDEC-C2B8 (IDEC-102) in Patients with Relapsed Low-grade or Follicular B-cell Lymphoma," Initiated Apr. 25, 1995, Report dated Jan. 15, 1997 (241 pages).
IDEC Pharmaceuticals Corporation, Form 10-K/A for the Fiscal Year ended Dec. 31, 1997, filed with the U.S. Securities and Exchange Commission (49 pages).
IDEC Phamiaceuticals Filing Details on the EDGAR system, Mar. 3, 1998, retrieved from https://www.sec.gov/Archives/edgar/data/875045/0000936392-98-000361-index.html on Mar. 21, 2017 (1 page).
*IDEC Pharmaceuticals v. Corixa Corp.*, Case No. 01-1637-IEG [Doc. Nos. 486, 584] (S.D. Cal.) Oct. 14, 2003.
Imrie K., et al. *Curr. Oncol.* 6(4): 228-35, 1999. Use of rituximab in the treatment of lymphoma: an evidence summary.
Information Disclosure Statement Form PTO-1449 considered by examiner on May 10, 2010 in U.S. Appl. No. 11/840,956 (Antonio J. Grillo-Lopez, Combination Therapies for B-Cell Lymphomas Comprising Administration of Anti-Cd20 Antibody, filed Aug. 18, 2007), pp. 1-31.

(56) References Cited

OTHER PUBLICATIONS

International Non-Hodgkin's Lymphoma Prognostic Factors Project, "A Predictive Model for Aggressive Non-Hodgkin's Lymphoma," *N Engl. J Med* 329(14): 987-994 (1993).
Intron®A, Interferon alfa-2b, recombinant for Injection, Product Information, revised Nov. 1997, pp. 1-37.
Jaffe, et al., "Introduction and overview of the classification of the lymphoid neoplasms," World Health Organization Classification of Tumors of Haematopoietic and Lymphoid Tissues, Swerdlow, et al., editors, 4th edition, Lyon, France 2008 pp. 158-166.
Jain R. K. *Sci. Am.* 271(1): 58-65, 1994. Barriers to drug delivery in solid tumors.
James, J. S. and Dubs, G., "FDA approves new kind of lymphoma treatment. Food and Drug Administration" *AIDS Treat News* (No. 284): 2-3, 1997, 1 pg. (Abstract only).
Janakiraman N., et al. *Blood* 92(10 Suppl. 1): 337a, abst. No. 1384, Nov. 1998. Rituximab: correlation between effector cells and clinical activity in NHL.
Janeway, et al., Chapter 9: The Humoral Immune Response in Immunobiology: The Immune System in Health and Disease, 1999, 4th Edition, (4 pages).
Jazirehi A. R., et al. *Oncogene* 24: 2121-43, 2005. Cellular and molecular signal transduction pathways modulated by rituximab (rituxan, anti-CD20 mAb) in non-Hodgkin's lymphoma: implications in chemosensitization and therapeutic intervention.
Jensen M., et al. *Ann. Hematol.* 77: 89-91, 1998. Rapid tumor lysis in a patient with B-cell chronic lymphocytic leukemia and lymphocytosis treated with an anti-CD20 monoclonal antibody (IDEC-C2B8, rituximab).
Johnson, et al., "Patterns of Survival in Patients with Recurrent Follicular Lymphoma: A 20-Year Study from a Single Center," Journal of Clinical Oncology, 1995, vol. 13, No. 1, pp. 140-147.
Jones, et al., "Improved Complete Remission Rates and Survival for Patients with Large Cell Lymphoma Treated with Chemoimmunotherapy", Cancer, 1983, vol. 51, pp. 1083-1090.
Jordan, et al., "Comparison of the Effects of Vinblastine, Vicristine, Vindesine, and Vinepidine on Microtubule Dynamics and Cell Proliferation in Vitro," Cancer Research, 1985, vol. 45, pp. 2741-2747.
Juweid M., et al. *Cancer Res.* 55(23 Suppl.): 5827s-5831s, 1995. Estimates of red marrow. dose by sacral scintigraphy in radioimmunotherapy patients having non-Hodgkin's lymphoma and diffuse bone marrow uptake.
Juweid M., et al. *Cancer Res.* 55(23 Suppl.): 5899s-5907s, 1995. Treatment of non-Hodgkin's lymphoma with radiolabeled murine, chimeric, or humanized LL2, an anti-CD22 monoclonal antibody.
Kaminski M., et al. *Antibody Immunoconj. Radiopharm.* 3(1): abst. No. 83, 1990. Radioimmunotherapy of advanced B-cell lymphoma with non-bone marrow ablative doses of 131-I MB-1 antibody.
Kaminski M., et al. *Antibody Immunoconj. Radiopharm.* 4(1): 36, abst. No. 66, 1991. Phase I trial results of 131-1 antibody radioimmunotherapy (RAIT) of B-cell lymphoma.
Kaminski M., et al. *J. Clin. Oncol.* 10(11): 1696-1711, 1992. Imaging, dosimetry and , radioimmunotherapy with iodine 131-labeled anti-CD37 antibody in B-cell lymphoma.
Kaminski M., et al. *Proc. Amer. Soc. Clin. Oncol.* 9: 271, abst. No. 1051, 1990. Radioimmunodetection (RID) and non-marrow ablative radioimmunotherapy (RIT) of B-cell lymphoma with 131-I MB-1 antibody.
Kaminski M., et al. Proc. Third Conf. on Radioimmunodetection and Radioimmunotherapy of Cancer, Princeton NJ, Nov. 15-17, 1990 (published at Antibody Immunoconj. Radiopharm. 4: 387, 1991), abst. No. 144. 131-1 anti-B1: Initial clinical evaluation in B-cell lymphoma.
Kaminski M.S., et al. *Antibody Immunoconj. Radiopharm.* 5(3): 345, abst. No. 57, 1992. Initial clinical radioimmunotherapy results with $^{131}$I-anti-B1 (anti-CD20) in refractory B-cell lymphoma.
Kaminski M.S., et al. *Blood* 76(10 Suppl. 1): 355a, abst. No. 1409, 1990. Phase I evaluation of 131-1 MB-1 antibody radioimmunotherapy (RIT) of B-cell lymphoma.

Kaminski M.S., et al. *Blood* 78(10 Suppl. 1): 43a, abst. No. 161, 1992. Radioimmunotherapy (RIT) of refractory B-cell lymphoma with 131-I-anti-B1 (anti-CD20) antibody: promising early results using non-marrow ablative radiation doses.
Kaminski M.S., et al. *J Clin. Oncol.* 14(7): 1974-81, 1996. Iodine-131-anti-B1 radioimmunotherapy for B-cell lymphoma.
Kaminski M.S., et al. *N. Engl. J Med.* 329: 459-65, 1993. Radioimmunotherapy of B-cell lymphoma with [$^{131}$I]anti-B1 (anti-CD20) antibody.
Kaplan EL, et al., "Nonparametric estimation from incomplete observations." J Am Stat Assoc, 1958, vol. 53, pp. 457-481.
Keating M., et al. *Semin. Oncol.* 27(6 suppl. 12): 86-90, 2000. High-dose rituximab therapy in chronic lymphocytic leukemia.
Kennedy, et al., "Incidence and nature of CD20-negative relapses following rituximab therapy in aggressive B-cell non-Hodgkin's lymphoma: a retrospective review," *Br. .1 Haematol.* 119(2): 412-6 (2002).
Khan, et al., "A Phase 2 Study of Rituximab in Combination with Recombinant Interleukin-2 for Rituximab-Refractory Indolent Non-Hodgkin's Lymphoma," Clin Cancer Res 12(23):7046-7053 (2006).
Kimby, et al., "Chlorambucil/prednisone vs. CHOP in symptomatic low-grade non-Hodgkin's lymphomas: A randomized trial from the Lymphoma Group of Central Sweden," Ann. Oncol. 1994, vol. 5, supp. 2, pp. 67-71.
Kimby, "Beyond immunochemotherapy: combinations of rituximab with cytokines interferon-alpha2a and granulocyte colony stimulating factor," *Semin. Oncol.* 29(2 Suppl. 6): 7-10 (2002).
Kimura, et al., "VII Medicaments for hematologic diseases 'lymphoid malignancy'; 177. Drug therapies for non-Hodgkin's lymphoma" Medicine vol. 24, No. 10 (1987), pp. 2194-2197 (English translation of Japanese Office Action dated Dec. 25, 2012, filed in corresponding JP Patent Application No. 2000-564662, attached).
King and Younes, "Rituximab: review and clinical applications focusing on non-Hodgkin's lymphoma," *Expert Rev. Anticancer Ther.* 1(2): 177-86 (2001).
Kinoshita T., et al. *J. Clin. Oncol.* 16(12): 3916, Dec. 1998. CD20-negative relapse in B-cell lymphoma after treatment with Rituximab.
Klarnet J.P., et al. *.1 Immunol.* 138(11): 4012-17, 1987. Antigen-driven T cell clones can proliferate in vivo, eradicate disseminated leukemia, and provide specific immunologic memory.
Knox S.J., et al. *Clin. Cancer Res.* 2: 457-70, 1996. Yttrium-90-labeled anti-CD20 monoclonal antibody therapy of recurrent B-cell lymphoma.
Knox S.J., et al. *I Immunother.* 16(2): 161, abst. No. 51, 1994. $^{90}$Y-anti-CD20 monoclonal antibody therapy (IDEC-Y2B8) for recurrent B cell lymphoma.
Knox S.J., et al. *I.J. Rad. Oncol. Biol.Phys.* 32: 215, 1995. $^{90}$Y-anti-CD20 monoclonal antibody therapy for recurrent B cell lymphoma.
Kohler and Milstein, "Derivation of Specific Antibody-Producing Tissue culture and Tumor Lines by Cell Fusion", European J. Immunology, 1976, vol. 6, pp. 511-519.
Kola, et al., "Can the pharmaceutical industry reduce attrition rates?" Nature Review, 2004, vol. 3, pp. 711-715.
Konopleva, et al., "The anti-apoptotic genes Bcl-X1 and Bcl-2 are over-expressed and contribute to chemoresistance of non-proliferating leukemic CD34+ cells," British Journal of Haematology, 2002, 118, pp. 521-534.
Koo, et al., "Methylation-dependent loss of RIP3 expression in cancer represses programmed necrosis in response to chemotehrapeutics," Cell Research, 2015, 25-707-725.
Kuzel T., et al. *Cancer Biother.* 8(1): 3-16, 1993. A phase I escalating-dose safety, dosimetry and efficacy study of radiolabeled monoclonal antibody LYM-1.
Kwak et. al., "Biological response modifiers", The Non-Hodgkin's Lymphomas, 2$^{nd}$ edition, Ch. 32, Ian T. MaGrath, Arnold, 1997, pp. 699-714.
Langmuir V.K. *NucL Med. Biol.* 19(2): 213-55, 1992. Radioimmunotherapy: clinical results and dosimetric considerations.
Larson S. M., et al. *Nucl. Med. Biol.* 16: 153-58, 1989. Comparison of bone marrow dosimetry and toxic effect of high dose $^{131}$I-labeled monoclonal antibodies administered to man.

(56) References Cited

OTHER PUBLICATIONS

Lauria F., et al. *Bone Marrow Transplant.* 18(1): 79-85, 1996. Immunologic and clinical modifications following low-dose subcutaneous administration of rIL-2 in non-Hodgkin's lymphoma patients after autologous bone marrow transplantation.
Lazzarino, M., et al "Immunochemotherapy with rituximab, vincristine and 5-day cyclophosphamide for heavily pretreated follicular lymphoma." Oncology. 2005;68(2-3):146-53.
Lefrak, et al., "A clinicopathologic analysis of adriamycin cardiotoxicity" *Cancer* 32(2) 1973, pp. 302-314 (Abstract only).
Leget, et al., "Use of rituximab, the new FDA-approved antibody", *Current Opinion in Oncology* 10, 1998, pp. 548-551.
Leichner P. K., et al. *Front. Rad. Ther. Oncol.* 24: 109-20, 1990. Dosimetry and treatment planning in radioimmunotherapy.
Leichner P. K., et al. *Med. Phys.* 20(2): 529-34, 1993. Tumor dosimetry in radioimmunotherapy: methods of calculation for beta particles.
Leonard et. al., "Monoclonal Antibody Therapy of Lymphoma", American Cancer Society Atlas of Clinical Oncology Malignant Lymphomas, Ch. 18, Michael L. Grossbard, BC Decker Inc. 2002, pp. 301-315.
Lepage, et al., "Treatment of Low-Grade Non-Hodgkin's Lymphomas: Assessment of Doxorubicin in a Controlled Trial," Hematological Oncology, 1990, vol. 8, pp. 31-39.
Levy R., et al. *Fed. Proc.* 42: 2650-56, 1983. Tumor therapy with monoclonal antibodies.
Li Tongdu (chief translator), Clinical Oncology, Anhui Science and Technology Publication, vol. 28-3, pp. 34-45, 1996 and English translation.
Ling N. R., et al. (in) *Leucocyte Typing III: White Cell Differentiation Antigens*, A.J. McMichael, et al., eds., Oxford: Oxford Univ. Pr., 1987, pp. 302-335. B-cell and plasma cell antigens: new and previously defined clusters.
Link B.K., et al. *Proc. Amer. Soc. Clin. OncoL* 17: 3a, abst. No. 7, 1998. Phase II pilot study of the safety and efficacy of rituximab in combination with CHOP chemotherapy in patients with previously untreated intermediate- or high-grade NHL.
Link M. P., et al. *I Immunol.* 137(9): 3013-18, 1986. A unique antigen on mature B-cells defined by a monoclonal antibody.
Lipton J. M., et al. *Blood* 60(5 Suppl. 1): 170a, abst. No. 609, 1992. Distribution of B1, CALLA, 02 microglobulin and Ia on hematopoiesis supporting cells (HSC) in short and long-tem cultures.
Lister, "The management of follicular lymphoma," Annals of Oncology, Supplement 2, vol. 2, pp. 131-135, (1991).
Litman, et al., "The multidrug-resistant phenotype associated with overexpression of the new ABC half-transporter, MXR (ABCG2)," Journal of Cell Science, 2000, No. 113, pp. 2011-2021.
Liu A. Y., et al., *J. Immunol.* 139(10): 3521-26, Nov. 1987. Production of a mouse-human chimeric monoclonal antibody to CD20 with potent Fc-dependent biologic activity.
LoBuglio AF, et al., "Mouse/human chimeric monoclonal antibody in man: Kinetics and Immune response." PNAS, 1989, vol. 86, pp. 4220-4224.
Lonberg N., et al. *Nature* 368: 856-59, 1994. Antigen-specific human antibodies from mice comprising four distinct genetic modifications.
Longo Dl, "Immunotherapy for Non-Hodgkin's Lymphoma." Curr. Opin. Oncol. 8(5): 353-59 (Sep. 1996).
Lopez-Guillermo et al. "The clinical significance of molecular response in indolent follicular lymphomas", Blood 91(8):2955-2960 (Apr. 15, 1998).
Lowman H. B. Slides presented at IBC Antibody Engineering Conference, Dec. 2, 2003. Differential activities in a series of humanized anti-CD20 antibodies.
Luce, et al., "Combined Cyclophosphamide, Vincristine, and Prednisone Therapy of Malignant Lymphoma," Cancer, 1971, vol. 28, No. 2, pp. 306-317.
Lum L. G., et al. *Blood* 69(2): 369-80, 1987. The kinetics of immune reconstitution after human marrow transplantation.

MabThera® Summary of Product Characteristics; Date of first authorization: Jun. 2, 1998; Date of latest renewal: Jun. 2, 2008, pp. 1-94.
Macedo, et al., "Standard CHOP with Reduced Dose of Doxorubicin (mini-CHOP) for Elderly Patients with Intermediate and High Grade Non-Hodgkin's Lymphoma (NHL)," Blood, 1994, 84 (10 Suppl. 1):644a, pp. 1-3.
Macey D. J., et al. *Front. Rad. Ther. Oncol.* 24: 123-31, 1990. A treatment planning program for radioimmunotherapy.
Macklis R. M., et al. *Antibody Immunoconj. Radiother.* 5(3): abst. No. 39, 1992. Induction of programmed cell death in malignant lymphomas after radioimmunotherapy.
Macklis R. M., et al. *Cancer* 73(3 Suppl.): 966-73, 1994. Radiobiologic studies of low-doserate $^{90}$Y-lymphoma therapy.
Maddy A.H., et al. *Immunol.* 68(3): 346-52, 1989. The role of cell maturation in the generation of phenotypic heterogeneity in B-cell chronic lymphocytic leukemia.
Madjd, et al., "CD44+ cancer cells express higher levels of the anit-apoptotic protein Bcl-2 in breast tumours," Cancer Immunity, 2009, vol. 9, pp. 1-7.
Maloney D. C., et al. *Blood* 90(6): 2188-2195, 1997. IDEC-C2B8 (Rituximab) anti-CD20 monoclonal antibody therapy in patients with relapsed low-grade non-Hodgkin's lymphoma.
Maloney D. G., et al. *Blood* 80(6): 1502-1510, 1992. Monoclonal anti-idiotype antibody therapy of B-cell lymphoma: the addition of a short course of chemotherapy does not interfere with the antitumor effect nor prevent the emergence of idiotype-negative variant cells.
Maloney D. G., et al. *Blood* 88(10: Suppl. 1): 637a, abst. No. 2635, 1996. The anti-tumor effect of monoclonal anti-CD20 antibody (mAb) therapy includes direct anti-proliferative activity and induction of apoptosis in CD20 positive non-Hodgkin's lymphoma (NHL) cell lines.
Maloney D. G., et al. *I Clin. Oncol.* 15(10): 3266-74, Oct. 1997. IDEC-C2B8: results of a phase 1 multiple-dose trial in patients with relapsed non-Hodgkin's Lymphoma.
Maloney D. G., et al., "Phase I clinical trial using escalating single-dose infusion of chimeric anti-CD20 monoclonal antibody (IDEC-C2B8) in patients with recurrent B-cell lymphoma," Blood 84(8): 2457-66, 1994.
Maloney, et al., "IDEC-C2B8: Results of a Phase I Multiple-Dose Trial in Patients with Relapsed Non-Hodgkin's Lymphoma", Journal of Clinical Oncology, vol. 15, No. 10, Oct. 1997, pp. 3266-3274.
Maloney, et al., "Newer Treatments for Non-Hodgkin's Lymphoma: Monoclonal Antibodies", Oncology vol. 12, No. 10, Oct. 2, 1998, pp. 1-21 http://www.cancernetwork.com/display/article/10165/72098 (Retrieved 1998).
Maloney, D. G., et al., "Chimeric Anti-CD20 (IDEC-C2B8) Monoclonal Antibody Therapy of Low-Grade Lymphoma", Cancer Invest 15(1 Suppl):78-79 (#70), 1997.
Maloney, D. G., et al., "IDEC-C2B8 Anti-CD20 Antibody: Results of Long-Term Follow-Up of Relapsed NHL Phase II Trial Patients", Blood 86(10):54a (#205), Nov. 1995.
Maloney, D. G., et al., "IDEC-C2B8: Final report on a Phase II trial in relapsed non-Hodgkin's lymphoma", Blood 84(10) Supplement 1:169a (#661), 1994.
Maloney, D. G., et al., "Initial Report on a Phase I/II Multiple Dose Clinical Trial of IDEC-C2B8 (Chimeric Anti-CD20) in Relapsed B-Cell Lymphoma", Proc Am Soc Clin Oncol 13:304 (#993) Mar. 1994.
Maloney, D. G., et al., "Phase I Clinical Trial Using Escalating Single Dose Infusion of Chimeric Anti-CD20 Monoclonal Antibody (IDEC-C2B8) in Patients with Recurrent B-Cell Lymphoma)", Blood 82(10 Suppl 1): 445a (#1763), Nov. 1993.
Maloney, D. G., et al., "Phase I/II Clinical Trials of IDEC-C2B8 (Chimeric Anti-CD20 Antibody) in Relapsed B-Cell Lymphoma", Cancer Investigation, vol. 13, Suppl 1, pp. 31-32 (#24), 1995.
Maloney, et al., "A Phase II Trial of CHOP Followed by Rituximab Chimeric Monoclonal Anti-CD20 Antibody for Treatment of Newly Diagnosed Follicular Non-Hodgkin's Lymphoma: SWOG 9800," Blood, Annual Meeting Program and Abstracts Issue, Dec. 7-11, 2001, 43rd Annual Meeting, vol. 98, No. 11, abstract #3502, pp. 1-3.

(56) References Cited

OTHER PUBLICATIONS

Mange, et al., "Immunotherapy with rituximab following high-dose therapy and autologous stem-cell transplantation for mantle cell lymphoma," Semin. Oncol. 29(1 Suppl. 2): 56-69 (2002).
Marcus, et al., "CVP chemotherapy plus rituximab compared with CVP as first-line treatment for advanced follicular lymphoma," Blood, 2005, vol. 105, No. 4, pp. 1417-1423.
Marcus, et al., "Phase III Study of R-CVP Compared with Cyclophosphamide, Vincristine, and Prednisone Alone in Patients with Previously Untreated Advanced Follicular Lymphoma," Journal of Clinical Oncology, 2008, vol. 26, No. 28, pp. 4579-4586.
Mariuzza et al. Science. 233: 747-53, 1986. Three-dimensional structure of an antigen-antibody complex at 2.8 A resolution.
Marquez S.D., et al. I.J. Rad. Oncol. Biol. Phys. 39: 327, abst. No. 2173, 1997. Hematological toxicity in radioimmunotherapy is predicted both by the computed absorbed whole body dose (cGy) and by the administered dose (mCi).
Martelli, et al., "Current Guidelines for the Management of Aggressive Non-Hodgkin's Lymphoma", Drugs 1997, 53(6): 957-972.
Marti G. E., et al. Ann. N.Y. Acad. Sci. 651: 480-83, 1992. CD20 and CD5 expression in B-chronic lymphocytic leukemia.
Marx J. L. Science 229(4712): 455-56, 1985. Antibodies made to order.
Masucci G., et al. Med. Oncol. Tumor Pharmacother. 8(3): 207-20, 1991. Chemotherapy and immunotherapy of colorectal cancer.
Mazza P., et al. Bone Marrow Trans. 23: 1273-78, 1999. Analysis of feasibility of myeloablative therapy and autologous peripheral stem cell (PBSC) transplantation in the elderly: an interim report.
McKelvey, et al., "Hydroxyldaunomycin (Adriamycin) Combination Chemotherapy in Malignant Lymphoma," Cancer, 1976, No. 4, pp. 1484-1493.
McLaughlin, et al., "Management of Patients with Nodular Lymphoma", UT M.D. Anderson Clinical Conference on Cancer, 1984, vol. 27, pp. 301-312.
McLaughlin, et al., "Rituximab in Indolent Lymphoma: The Single-Agent Pivotal Trial", Semin Oncol 26(5, 14 Suppl):79-87, Oct. 1999.
McLaughlin P, et al., "Fludarabine phosphate in lymphoma: an important new therapeutic agent" in Advances in Lymphoma Research, Boston, MA, Cabanillas F, Rodriguez, MA, Kluwer Academic Publishers, 1996, pp. 3-14.
McLaughlin P, et al., "A Phase III (PIII) pivotal trial of IDEC-C2B8 in patients (pts) with relapsed low-grade or follicular lymphoma." J Mol Med 75(7):B231 (#257), Jul. 1997.
McLaughlin P., et al. Blood 92(10 Suppl. 1): 414a-415a, abst. No. 1712, Nov. 1998. Efficacy controls and long-term follow-up for relapsed or refractory, low-grade or follicular (R-LG/F) NHL.
McLaughlin P., et al. J Clin. Oncol. 16(8): 2825-33, Aug. 1998. Rituximab chimeric-antiCD20 monoclonal antibody therapy for relapsed indolent lymphoma: half of patients respond to a four-dose treatment program.
McLaughlin P., et al. J. Clin Oncol. 16(8): 2825-2833, Aug. 1998. "Rituximab chimeric-anti-CD20 monoclonal antibody therapy for relapsed indolent lymphoma: half of patients respond to a four-dose treatment program" (Previously submitted); with e-mail from publisher Glenn Landis dated Nov. 5, 2012, 1 page, stating the official publication date thereof was Aug. 1, 1998.
McLaughlin P., et al. Oncology 12(12): 1763-81, 1998. Clinical status and optimal use of rituximab for B-cell lymphomas.
McLaughlin P., et al., "IDEC-C2B8 (Rituximab): Clinical activity in clinically-chemoresistant (CCRD) low-grade or follicular lymphoma (LG/F NHL) and in patients (pts) relapsing after anthracycline therapy (ANTBRA-RX) or ABMT.", Proc Am Soc Clin Oncol, May 1997, vol. 16, Abstract #55, p. 16a.
McLaughlin P et al., "IDEC-C2B8 anti-CD20 antibody: Final report on a Phase III pivotal trial in patients (PTS) with relapsed low-grade or follicular lymphoma (LG/F NHL).", Blood 88(10):90a (#349), Nov. 1996.
McLaughlin P., et al., "Pharmacokinetics (PK) and Pharmacodynamics (PD) of the anti-CD20 antibody (MAB) IDEC-C2B8 in patients (PTS) with relapsed low-grade or follicular lymphoma (LG/F NHL)" Blood (Abstract #350) 88(10 Suppl 1, Part 1 of 2):90a (Nov. 1996).
McLaughlin P., et al., "Pivotal Phase III clinical trial (PIII CT) of the chimeric anti-CD20 antibody (MAB) IDEC-C2B8 in patients (PTS) with relapsed low-grade or follicular lymphoma (LG/F NHL): A preliminary report.", Ann Oncol 7 (3 Suppl):57 (#194), Jun. 1996.
McLaughlin P., et al., "Preliminary report on a Phase III pivotal trial of the anti-CD20 antibody (MAB) IDEC-C2B8 in patients (PTS) with relapsed low-grade or follicular lymphoma." Proc Am Soc Clin Oncol 15:417 (#1281), May 1996.
McLaughlin, P., et al., "Clinical Status and Optimal Use of Rituximab for B-Cell Lymphomas", Dec. 1998, Oncology, pp. 1763-1781.
McLaughlin, Peter, presentation titled "IDEC-C2B8 Anti-CD20 Antibody: Final Report on A Phase III Pivotal Trial in Patients (PTS) With Relapsed Low-Grade or Follicular Lymphoma (LG/F NHL)" presented at the 38th Annual Meeting of the American Society of Hematology in Orlando, Florida on Dec. 6-10, 1996 (21 pages)).
McLaughlin, Peter, presentation titled "Pharmacokinetics (PK) and Pharmacodynamics (PD) of the Anti-CD20 Antibody (MAB) IDEC-C288 in Patients (PTS) With Relapsed Low-Grade or Follicular Lymphoma (LG/F NHL)" presented at the 38th Annual Meeting of the American Society of Hematology in Orlando, Florida on Dec. 6-10, 1996 (21 pages).
McNeil, C. "Non-Hodgkin's Lymphoma Trials in Elderly Look Beyond CHOP", Journal of the National Cancer Institute, Feb. 18, 1998, vol. 90, No. 4, pp. 266-267.
Meeker, T. C., et al., "A clinical trial of anti-idiotype therapy for B cell malignancy", Blood 1985; 65: pp. 1349-1363.
Meredith R. F., et al. I Nucl. Med. 33(9): 1648-53, 1992. Dose fractionation of radiolabeled antibodies in patients with metastatic colon cancer.
Meyer, et al., "Randomized Phase II Comparison of Standard CHOP with Weekly CHOP in Elderly Patients with Non-Hodgkin's Lymphoma," Journal of Clinical Oncology, Sep. 1995, vol. 13, No. 9, pp. 2386-2393.
Meyer, R. M., et al. "A phase I trial of standard and cyclophosphamide dose-escalated CHOP with granulocyte colony stimulating factor in elderly patients with non-Hodgkin's lymphoma," Leukemia and Lymphoma, 1998, vol. 30, pp. 591-600.
Miller, et al., "Initial Chemotherapy of Clinically Localized Lymphomas of Unfavorable Histology," Blood, 1983, vol. 62, No. 2, pp. 413-418.
Miller, R.A., et al., "Treatment of B-Cell Lymphoma with monoclonal anti-idiotype antibody.", N Engl J Med 306(9): 517-522, 1982.
Mishell B.E., et al., eds. Selected Methods in Cellular Immunology, San Francisco: Freeman, 1980, p. 287-304. Modification and use of antibodies to label cell surface antigens.
Misset, et al., "Dose-finding study of docetaxel and doxorubicin in first-line treatment of patients with metastatic breast cancer", Annals of Oncology 10, 1999, pp. 553-560.
Monnereau, et al., "L'interféron alpha dans le traitement des lymphomes non hodgkiniens de faible malignité", Bulletin du Cancer, vol. 85, No. 10, 1998, pp. 855-865, in French with English translation, pp. 1-19.
Moreau, et al., "Peripheral blood stem cell transplantation as front-line therapy in patients aged 61 to 65 years: a pilot study," Bone Marrow Transplantation 1998, 21:1193-1196.
Morrison and Peterson, "Combination chemotherapy in the treatment of follicular low-grade lymphoma," Leuk. Lymphoma 10 Suppl.: 29-33 (1993).
Morrison S., et al. Proc. Nat'l Acad. Sci. USA 81: 6851-54, 1984. Chimeric human antibody molecules: mouse antigen-binding domains with human constant region domains.
Morrison S.L. Science 229: 1202-07, 1985. Transfectomas provide novel chimeric antibodies.
Morrison, et al., "Dose intensity of CHOP alone or with rituximab in diffuse large B-cell lymphoma (DLBCL) in patients >60 years of age: an analysis of the intergroup trial (CALGB 9793, ECOG-SWOG 4494)", [Abstract] Ann Oncol 16 (Suppl 5): A-224, v102, 2005.

(56) References Cited

OTHER PUBLICATIONS

Morrison, et al., "Maintenance rituximab (MR) compared to observation (OBS) after R-CHOP or CHOP in older patients (pts) with diffuse large B-cell lymphoma (DLBCL): An Intergroup E4494/C9793 update", [Abstract] *J Clin Oncol* 25 (Suppl 18): A-8011, 443s, 2007.
Mueller BM, et al., "Enhancement of antibody-dependent cytotoxicity with a chimeric anti-GD2 antibody." J Immunol, 1990, vol. 144, pp. 1382-1386.
Multani P.S., et al. *J. Clin. Oncol.* 16(11): 3691-3710, 1998. Monoclonal antibody-based therapies for hematologic malignancies.
Munro A. *Nature* 312: 597, 1984. Uses of chimeric antibodies.
Murray J. L., et al. *I Biol. Resp. Modifiers* 9(6): 556-63, 1990. Recombinant alpha-interferon enhances tumor targeting of an antimelanoma monoclonal antibody in vivo.
Murray J. L., et al. *J. NucL Med.* 26: 3328-29, 1985. The effect of radionuclide dose on imaging with indium-111-labeled anti P-97 monoclonal antibody.
Muzaffar S., et al. *I Pak. Med. Assn.* 47(4): 106-09, Apr. 1997. Immunophenotypic analysis of non-Hodgkin's lymphoma.
Nadler L.M., et al. *Cancer Res.* 40(9): 3147-54, 1980. Serotherapy of a patient with a monoclonal antibody directed against a human lymphoma-associated antigen.
Nadler L.M., et al. *J. Clin. Invest.* 67: 134-140, 1981. A unique cell surface antigen identifying lymphoid malignancies of B cell origin.
Nadler L.M., et al. *J. Clin. Invest.* 74(2): 332-40, 1984. B cell origin of non-T cell acute lymphoblastic leukemia. A model for discrete stages of neoplastic and normal pre-B cell differentiation.
Nadler L.M., et al. *Lancet* 2(8400): 427-31, 1984. Anti-B1 monoclonal antibody and complement treatment in autologous bone-marrow transplantation for relapsed B-cell non-Hodgkin's lymphoma.
Nakamura K., et al. *Oncology* 50(1): 35-40, 1993. Effect of alpha-interferon on anti-alpha fetoprotein-monoclonal-antibody targeting of hepatoma.
Neuberger M.S., et al. *Nature* 314: 268-70, 1985. A hapten-specific chimeric IgE antibody with human physiological effector function.
Nguyen D.T., et al. *Eur. I Haematol.* 62: 76-82, 1999. IDEC-C2B8 anti-CD20 (Rituximab) immunotherapy in patients with low-grade non-Hodgkin's lymphoma and lymphoproliferative.disorders: evaluation of response on 48 patients.
Nielsen B., et al. *Eur. J Haematol.* 48(3): 146-51, 1992. Interferon-a-induced changes in surface antigens in a hairy-cell leukemia (JOK-1), and a Burkitt's lymphoma cell line (Daudi) during in vitro culture.
Non-Hodgkin's Lymphoma Pathologic Classification Project. *Cancer* 49(10): 2112-35, 1982. National Cancer Institute sponsored study of classifications of non-Hodgkin's lymphomas.
Notice of Allowability dated Jun. 26, 2012 in U.S. Appl. No. 11/840,956 (Antonio Grillo-Lopez, filed Aug. 18, 2007), pp. 1-2.
O'Brien S. *Blood* 92(10 Suppl 1): 105a, abst. No. 431, 1998. Phase I/II study of rituxan in chronic lymphocytic leukemia (CLL).
O'Brien S., et al. *N. Engl. J. Med.* 330(5): 319-22, 1994. Lack of effect of 2chlorodeoxyadenosine therapy in patients with chronic lymphocytic leukemia refractory to fludarabine therapy.
O'Brien S.M., et al. *J. Clin. Oncol.* 19: 2165-70, 2001. Rituximab dose-escalation trial in chronic lymphocytic leukemia.
O'Brien, et al., "The natural history of low grade non-Hodgkin's lymphoma and the impact of a no initial treatment policy on survival," Q J. Med, 1991, 80(292):651-660.
Oettgen H.C., et al. *Hybridoma* 2(1): 17-28, 1983. Further biochemical studies of the human B-cell differentiation antigens B1 and 132.
Oncology Nursing Society, onsopcontent.ons.org/oes/online_ce?lymph?.05classification.htm, retrieved Feb. 25, 2003, Current therapies and future directions in the treatment of non-Hodgkin's lymphoma.
Onrust, et al., "Rituximab" *Drugs* 58(1), 1999, pp. 79-88.

Orura, et al., "Therapeutic future direction with new clinical trials for refractory lymphoid malignancies," Journal of Japan Lymphoreticular System Society, 1997, 37, 4, 285-296.
Ozato K., et al. *J. Immunol.* 126(1): 317-21, 1981. Monoclonal antibodies to mouse WIC antigens. III. Hybridoma antibodies reacting to antigens of the H-2b haplotype reveal genetic control of isotype expression.
Ozer, et al., "Recombinant interferon-alpha therapy in patients with follicular lymphoma," *Cancer* 82(10): 1821-30 (1998).
Palmieri, et al., "Maintenance therapy with recombinant interferon alpha-2B (αIFN) in prognostically unfavorable aggressive non-Hodgkin's lymphomas (NHL)" *Oncology Reports* 3: 1996, pp. 733-735.
Panka D. J., et al. *Proc. Nat'l. Acad. Sci.* 85: 3080-84, 1988. Variable region framework differences result in decreased or increased affinity of variant anti-digoxin antibodies.
Parker B.A., et al. *Cancer Res.* 50(3): 1022s-1028s, 1990. Radioimmunotherapy of human 13-cell lymphoma with $^{90}$Y-conjugated antiidiotype monoclonal antibody.
Patent Owner's Preliminary Response filed in Inter Partes Review No. IPR2015-00418 re: U.S. Pat. No. 8,329,172, (Grillo-Lopez, "Combination Therapies for B-Cell Lymphomas Comprising Administration of Anti-CD20 Antibody"), dated Jul. 10, 2017 (69 pages).
Patent Owner's Preliminary Response filed in Inter Partes Review No. IPR2017-01093 re: U.S. Pat. No. 8,329,172, (Grillo-Lopez, "Combination Therapies, for B-Cell Lymphomas Comprising Administration of Anti-CD20 Antibody"), dated Jul. 10, 2017 (78 pages).
Patent Owner's Preliminary Response filed in Inter Partes Review No. IPR2015-01094 re: U.S. Pat. No. 8,557,244, (White, et al., "Treatment of Aggressive Non-Hodgkin's Lymphoma with Anti-CD20 Antibody"), dated Jul. 5, 2017 (73 pages).
Patent Owner's Preliminary Response filed in Inter Partes Review No. IPR2015-01095 re: U.S. Pat. No. 9,296,821 (Grillo-Lopez, "Combination Therapies for B-Cell Lymphomas Comprising Administration of Anti-CD20 Antibodies"), dated Jul. 10, 2017 (79 pages).
Patent Owner's Preliminary Response filed in Inter Partes Review No. IPR2017-01166 re: U.S.U.S. Pat. No. 8,329,172, (Grillo-Lopez, "Combination Therapies for B-Cell Lymphomas Comprising Administration of Anti-CD20 Antibody"), dated Aug. 15, 2017 (61 pages).
Patent Owner's Preliminary Response filed in Inter Partes Review No. IPR2017-01167 re: U.S. Pat. No. 8,557,244 (White, et al., "Treatment of Aggressive Non-Hodgkin's Lymphoma with Anti-CD20 Antibody"), dated Aug. 8, 2017 (72 pages).
Patent Owner's Updated Mandatory Notices in Petition for Inter Partes Review of U.S. Pat. No. 8,329,172 dated May 11, 2015 (U.S. Appl. No. 11/840,956, Antonio J. Grillo-Lopez, Combination Therapies for B-Cell Lymphomas Comprising Administration of Anti-Cd20 Antibody, filed Aug. 18, 2007) pp. 1-4.
Patient Information SAKK protocol 35/98, revised Dec. 18, 1998 with English translation, pp. 1-5.
PDQ—NCI's Comprehensive Cancer Database, http://web.archive.org/web/19980116194104/http://cancernet.nci.nih.gov/pdq.htm (archived Jan. 16, 1998) pp. 1-2 (retrieved Dec. 4, 2014).
Pearson J. W., et al. *Cancer Res.* 49(18): 4990-95, 1989. Enhanced therapeutic efficacy of an immunotoxin in combination with chemotherapy against an intraperitoneal human tumor xenograft in athymic mice.
Peterson et. al., "Cyclophosphamide versus cyclophosphamide plus interferon alfa-2b in follicular low-grade lymphomas: an intergroup phase III trial (CALGB 8691 and EST 7486)", Proceedings of ASCO, May 17-20, 1997, vol. 16, Abstract 48, p. 14a.
Petition for Inter Partes Review of U.S. Pat. No. 8,329,172 IPR2015-00418 (Grillo-Lopez, "Combination Therapies for B-Cell Lymphomas Comprising Administration of Anti-CD20 Antibody"), dated Dec. 15, 2014 by Boehringer Ingelheim International GmbH and Boehringer Ingelheim Pharmaceuticals, Inc. (76 pages).
Petition for Inter Partes Review of U.S. Pat. No. 8,329,172, IPR2017-01166 (Grillo-Lopez, "Combination Therapies for B-Cell Lymphomas Cpmprising Administration of Anti-CD20 Antibody"), dated Apr. 21, 2017 by Pfizer, Inc. (67 pages).

(56) References Cited

OTHER PUBLICATIONS

Petition for Inter Partes Review of U.S. Pat. No. 8,557,244, IPR2017-01167 (White, et al., "Treatment of Aggressive Non-Hodgkin's Lymphoma with Anti-CD20 Antibody"), dated Apr. 27, 2017 by Pfizer, Inc. (63 pages).
Petition for Inter Partes Review of U.S. Pat. No. 8,821,873, IPR2017-01168 (White, et al., "Treatment of Diffuse Large Cell Lymphoma with Anti-CD20 Antibody"), dated Apr. 28, 2017 by Pfizer, Inc. (86 pages).
Petition for Inter Partes Review of U.S. Pat. No. 9,296,821, IPR2018-00186 (Grillo-Lopez, "Combination Therapies for B-Cell Lymphomas Comprising Administration of Anti-CD20 Antibodies"), dated Dec. 1, 2017 by Pfizer, Inc. (74 pages).
Petition for Inter Partes Review of U.S. Pat. No. 9,504,744, IPR2018-00231 (White, et al., "Treatment of Diffuse Large-Cell Lymphoma with Anti-CD20 Antibody"), dated Dec. 1, 2017 by Pfizer, Inc. (78 pages).
Petition for Inter Partes Review U.S. Pat. No. 8,329,172, IPR2017-01093 (Grillo-Lopez, "Combination Therapies for B-Cell Lymphomas Comprising Administration of Anti-CD20 Antibody"), dated Mar. 15, 2017 by Celltrion, Inc. (78 pages).
Petition for Inter Partes Review U.S. Pat. No. 8,557,244, IPR2017-01094 (White, et al., "Treatment of Aggressive Non-Hodgkin's Lymphoma with Anti-CD20 Antibody"), dated Mar. 15, 2017 by Celltrion, Inc. (81 pages).
Petition for Inter Partes Review U.S. Pat. No. 9,296,821, IPR2017-01095 (Grillo-Lopez, "Combination Therapies for B-Cell Lymphomas Comprising Administration of Anti-CD20 Antibodies"), dated Mar. 15, 2017 by Celltrion, Inc. (86 pages).
Petitioner's Request for Rehearing on the Institution Decision in Inter Partes Review of U.S. Pat. No. 8,329,172 dated Dec. 15, 2014 (U.S. Appl. No. 11/840,956, Antonio Grillo-Lopez, Combination Therapies for B-Cell Lymphomas Comprising Administration of Anti-Cd20 Antibody, filed Aug. 18, 2007) pp. 1-18.
Petryk et al., "Indolent B-Cell Lymphomas", American Cancer Society Atlas of Clinical Oncology Malignant Lymphomas, Ch. 6, Michael L. Grossbard, BC Decker Inc. 2002, pp. 94-111.
Petryk M., et al. *Oncologist* 6: 317-26, 2001. ASCO 2001: Critical commentaries: Hematologic malignancies.
Pettengell, et al., "Randomised study of rituximab in patients with relapsed or resistant follicular lymphoma prior to high-dose therapy as in vivo purging and to maintain remission following high-dose therapy", J. Clin. Oncol., 2010, vol. 18, Supp. 10, abstr. 8005, retrieved from http://meetinglibrary.asco.org/print/57934 on Feb. 10, 2016 (2 pages).
Pettengell, Ruth (on behalf of the EBMT Lymphoma Working Party), "Randomised study of rituximab (MabThera) in patients with relapsed or resistant follicular lymphoma prior to high dose therapy as in vivo purging and to maintain remission (NCT00005589)", slides presented by the European Group for Blood and Marrow Transplantation at the 2010 ASCO Annual Meeting (20 pages).
Pfreundschuh, et al., "CHOP-lie chemotherapy plus rituximab versus CHOP-like chemotherapy alone in young patients with good-prognosis diffuse large-B-cell lymphoma: a randomised controlled trial by the MabThera International Trial (MInT) Group", http://oncology.thelancet.com, vol. 7, May 2006, pp. 379-391.
Phase III Trial of CHOP versus CHOP and Chimeric Anti-CD20 Monoclonal Antibody (IDEC-C2B8) in Patients 60 Years of Older with Diffuse Mixed, Diffuse Large Cell and Immunoblastic Large Cell Histology Non-Hodgkin's Lymphoma; ECOG E4494, CALGB 9793; Suggested Patient Consent Form, 1997 (4 pages).
Pickup, "Clinical Pharmacokinetics pf Prednisone and Prednisolone," CliniCal Pharmacokinetics 1979, vol. 4, pp. 111-128.
Pietersz G. A., et al. *Immunol. Cell. Biol.* 65(2): 111-25, 1987. The use of monoclonal antibody conjugates for the diagnosis and treatment of cancer.
Pinter-Brown, et al., "Hodgkin and Non-Hodgkin Lymphoma," in Manual of Clinical Oncology, 6th Edition, Lippincott Williams & Wilkins publishing, Dennis A. Cascito, ed., 2009, pp. 431-470.

Piro L., et al. *Blood* 90(10 Suppl. 1): 510a, abst. No. 2272, 1997. Rituxantm (rituximab, IDEC-C2B8): Interim analysis of a phase II study of once weekly times 8 dosing in patients with relapsed low-grade or follicular non-Hodgkin's lymphoma.
Piro L.D., et al. *Ann. Oncol.* 10: 655-61, 1999. Extended Rituximab (anti-CD20 monoclonal antibody) therapy for relapsed or refractory low-grade or follicular non-Hodgkin's lymphoma.
Piro LD, "Cladribine in the treatment of low-grade non-Hodgkin's lymphoma." Semin Hematol, 1996, vol. 33, No. 1, SUPPL 1, pp. 34-39.
Pitini et al. "Interleukin-2 and Lymphokine-Activated Killer Cell Therapy in Patients with Relapsed B-Cell Lymphoma Treated with Rituximab," Clin Cancer Res 13(18):5497 (2007).
Polyak M. J., et al. *Blood* 99: 3256-62, 2002. Alanine-170 and praline-172 are critical determinants for extracellular CD20 epitopes; heterogeneity in the fine specificity of CD20 monoclonal antibodies is defined by additional requirements imposed by both amino acid sequence and quaternary structure.
Portlock, C.S. and Rosenberg, S.A., "Combination chemotherapy with cyclophosphamide, vincristine, and prednisone in advanced non-Hodgkin's lymphomas" *Cancer* 37(3); 1976, pp. 1275-1282.
Portlock, et al., "No initial therapy for stage III and IV non-Hodgkin's lymphomas of favorable histologic types," Ann Intern Med, 1979, 90(1):10-13.
Pott-Hoeck C., et al., "Purine analogs in the treatment of low-grade lymphomas and chronic lymphocytic Leukemias." Ann Oncol, 1995, vol. 6, pp. 421-433.
Poynton CH, et al., "Adverse reactions to Campath-1H monoclonal antibody." Lancet , 1993, vol. 341, p. 1037.
Preliminary Amendment filed Oct. 31, 2007 in U.S. Appl. No. 11/840,956 (Antonio Grillo-Lopez, filed Aug. 18, 2007), pp. 1-5.
Press O. W., et al. *Proc. Amer. Soc. Clin. Oncol.* 5: 221, abst. No. 864, 1986. Serotherapy of malignant B cell lymphomas with monoclonal antibody 1F5 (anti-CD20).
Press O. W. *Cancer I Sci. Amer.* 4(Suppl 2): S19-S26, Jul. 1998. Prospects for the management of non-Hodgkin's lymphomas with monoclonal antibodies and Immunoconjugates.
Press O. W., et al. *Adv. Exp. Med. Biol.* 303: 91-96, 1991. Radiolabeled antibody therapy of human B cell lymphomas.
Press O. W., et al. *Blood* 69(2): 584-91, 1987. Monoclonal antibody 1F5 (anti-CD20) serotherapy of human B cell lymphomas.
Press O. W., et al. *Cancer Res.* 49(17): 4906-12, 1989. Endocytosis and degradation of monoclonal antibodies targeting human B-cell malignancies.
Press O. W., et al. *J. Clin. Oncol.* 7(8): 1027-38, 1989. Treatment of refractory non-Hodgkin's lymphoma with radiolabeled MB-1 (anti-CD37) antibody.
Press O. W., et al. *Lancet* 346(8971): 336-40, 1995. Phase II trial of $^{131}$I-B1 (anti-CD20) antibody therapy with autologous stem cell transplantation for relapsed B cell lymphomas.
Press O. W., et al. *N Engl. I Med.* 329(17): 1219-23, 1993. Radiolabeled-antibody therapy of B-cell lymphoma with autologous bone marrow support.
Press O. W., et al. *Proc. Amer. Soc. Clin. Oncol.* 17, abst. No. 9, May 1998. A phase I/II trial of high dose iodine-131-anti-B1 (anti-CD20) monoclonal antibody, etoposide, cyclophosphamide, and autologous stem cell transplantation for patients with relapsed B cell lymphomas.
Price, et al., "Interferon Alfa-2b in Addition to Chlorambucil in the Treatment of Follicular Lymphoma: Preliminary Results of a Randomized Trial in Progress," Eur. J. Cancer, 1991, vol. 27, suppl 4, pp. S34-S36.
Printout of the "About the Internet Archive", https://archive.org/about retrieved Nov. 21, 2017, pp. 1-2.
Public Hearing Transcript, Biological Response Modifiers Advisory Committee, Center for Biological Evaluation and Research, Food and Drug Administration, nineteenth meeting Jul. 25, 1997, available at http://www.fda.gov/ohrms/dockets/ac/97/transcpt/3311t2.pdf pp. 1-201.
Rai K. R., et al. (in) R. Hoffman, R., ed., *Hematology*, 2d. ed., Churchill Livingstone, 1995, Chapter 83, pp. 1308-19. Chronic lymphocytic leukemia.

(56) References Cited

OTHER PUBLICATIONS

Randomized Phase III Study in Low Grade Lymphoma Comparing Cyclophosphamide/Fludarabine to Standard Therapy Followed by Maintenance Anti-CD20 Antibody; ECOG E1496; Suggested Patient Consent Form, 1998, (3 pages).
Rapoport, et al., "Autotransplantation for advanced lymphoma and Hodgkin's disease followed by post-transplant rituxan/GM-CSF or radiotherapy and consolidation chemotherapy," *Bone Marrow Transplant.* 29(4): 303-12 (2002).
Rastetter, et al., "Rituximab: expanding role in therapy for lymphomas and autoimmune diseases," Annu. Rev. Med., 55: 477-503 (2004).
Ravaud, et al., "Adjuvant Bacillus Calmette-Guerin Therapy in Non-Hodgkin's Malignant Lymphomas: Long-Term Results of a Randomized Trial in a Single Institution", J. Clinical Oncology, 1990, vol. 8, pp. 608-614.
Reff M., et al. *I Cell. Biochem. Suppl.* 17E: 260, abst. No. T103, 1993. Depletion of B cells in vivo by a chimeric mouse human monoclonal antibody to CD20.
Reff M.E., et al. *Blood* 83(2): 435-45, 1994. Depletion of B cells in vivo by a chimeric mouse human monoclonal antibody to CD20.
Reilly R.M. *Clin. Pharm.* 10: 359-75, 1991. Radioimmunotherapy of malignancies.
Rituxan (Rituximab) label (Nov. 1997) (2 pages).
Rituxan (Rituximab) label (revised 2014) (44 pages).
Rituxan® (Rituximab) Draft Labeling Text, U.S. BL 103705/5230 Amendment: RITUXAN®(Rituximab)—Genentech, Inc. Sep. 29, 2006, pp. 1-46.
RITUXAN® (Rituximab) ECOG 1496 Trial for Low-grade or Follicular Non-Hodgkin's Lymphoma, 2012, pp. 1-3, http://www.rituxan.com/hem/hcp/non-hodgkin/post-induction/ecog/index.html.
Rituxan® (Rituximab) Labeling Text, U.S. BL 103705 Supplemental Amendment: Rituxan Rheumatoid Arthritis—Genentech , Inc. Feb. 2006, pp. 1-53.
Ritz J, et al., "Serotherapy of acute lymphoblastic leukemia with monoclonal antibody." Blood, 1981, vol. 58, pp. 141-152.
Robertson M. J., et al. *Blood* 79(9): 2229-36, 1992. Human bone marrow depleted of CD33—positive cells mediates delayed but durable reconstitution of hematopoiesis: Clinical trial of MY9 monoclonal antibody-purged autografts for the treatment of acute myeloid leukemia.
Robinson R., et al. *Human Antibody Hybrid* 2: 84-93, 1991. Chimeric mouse-human anti-carcinoma antibodies that mediate different anti-tumor cell biological activities.
Roche press release, Investor Update, Basel, Jun. 7, 2004, "MabThera/Rituxan® maintenance therapy dramatically improves progression-free survival in patients with indolent Non-Hodgkin's Lymphoma (NHL)", pp. 1-3.
Rogers, J., et al., "Analysis of bcl-2 t(14;18) translocation in relapsed B-cell lymphoma patients treated with the chimeric anti-CD20 antibody IDEC-C2B8.", Proc Annu Meet Am Assoc Cancer Res 37:213 (#1456), Mar. 1996.
Rogers, J., et al., "Clearance of bcl-2 (t14;18) from peripheral blood (PB) and bone marrow (BM) in patients (PTS) with relapsed low-grade or follicular (IWF:A-D) lymphoma (NHL) following single-agent therapy with the chimeric anti-CD20 antibody (MAB) IDEC-C2B8.", Ann Oncol 7(3 Suppl):34 (#108), Jun. 1996.
Rohatiner et. al., "Follicular Lymphoma", The Non-Hodgkin's Lymphomas, 2$^{nd}$ edition, Ch. 41, Ian T. MaGrath, Arnold, 1997, pp. 867-895.
Rohatiner et. al., "Meta-Analysis to Evaluate the Role of Interferon in Follicular Lymphoma," J. Clinical Oncology, Apr. 2005, vol. 23, No. 10, pp. 2215-2223.
Rohatiner, et al., "A radomized controlled trial to evaluate the role of interferon as initial and maintenance therapy in patients with follicular lymphoma," British Journal of Cancer, 2001, 85(1), pp. 29-35.
Rosenberg J., "Pharmacokinetics (PK) of the chimeric anti-CD20 antibody (MAB) IDEC-C2B8: Analysis of serum concentrations in patients (PTS) with relapsed B-cell lymphoma." Br J Haematol 93 (2 Suppl):283 (#1071), May 1996.
Rosenberg, "Immunotherapy and Gene Therapy of Cancer," Cancer Research 1991, (Suppl.) 51, 5074s-5079s.
Rosenberg, J., et al., "Pharmacokinetic analysis of serum concentrations of the chimeric anti-CD20 antibody IDEC-C2B8 in patients with relapsed B-cell lymphoma." Proc Am Soc Clin Oncol 15:418 (#1282), May 1996.
Rosenberg, S.A., "The Low-Grade Non-Hodgkin's Lymphomas: Challenges and Opportunities," J. Clin. Oncol. 1985, vol. 3, No. 3, pp. 299-310.
Rottenburger C., et al. *Br. J. Haematol.* 106(2): 545-52, 1999. Clonotypic CD20+ and CD19+ B cells in peripheral blood of patients with multiple myeloma post high-dose therapy and peripheral blood stem cell transplantation.
Rudikoff S., et al. *Proc. Nat'l. Acad. Sci.* 79: 1979-83, 1982. Single amino acid substitution altering antigen-binding specificity.
Ruuls, S.R., et al., "Novel human antibody therapeutics: the age of the Umabs," Biotechnol. J. 2008, vol. 3, pp. 1157-1171.
Sahagan B. G., et al. *J. Immunol.* 137: 1066-74, 1986. A genetically engineered murine/human chimeric antibody retains specificity for human tumor-associated antigen.
Saville, M. W. Statement of M. Wayne Saville, M.D., dated Dec. 20, 2007, submitted by applicant in Taiwan (R.O.C.) patent application No. 088119557.
Scharff M. *Harvey Lectures* 69: 125-42, 1974. The synthesis, assembly, and secretion of immunoglobulin: a biochemical and genetic approach.
Schein et. al., "Non-Hodgkin's Lymphoma: Patterns of Relapse from Complete Remission After Combination Chemotherapy", Cancer, 1975, vol. 35, pp. 354-357.
Schlom J., et al. *J. Natl. Cancer Inst.* 82(9): 763-71, 1990. Advantage of dose fractionation in monoclonal antibody-targeted radioimmunotherapy.
Schmitz, et al., "Clonal selection of CD20-negative non-Hodgkin's lymphoma cells after treatment with anti-CD20 antibody rituximab," Br J Haematol, 1999, 106:571-572.
Schwartz-Albiez R., et al. *J. Immunol.* 140(3): 905-14, 1988. The B cell-associated CD37 antigen (gp40-52). Structure and subcellular expression of an extensively glycosylated glycoprotein.
Seaver S. *Gen. Engr. News.* 19 and 21, 1982. Monoclonal antibodies in industry: more difficult than originally thought.
See-Lasley K., et al. *Manual of Oncology Therapeutics*, St. Louis: C.V. Mosby Co., pp. 44-71, 1981. Hodgkin's disease and non-Hodgkin's lymphoma.
*SEER Stat Fact Sheets: Non-Hodgkin Lymphoma*, National Cancer Institute, http://seer.cancer.gov/statfacts/html/nhl.html pp. 1-9 (retrieved Dec. 2, 2014).
Senter P. D., et al. *Adv. Exp. Med Biol.* 303: 97-105, 1991. Activation of prodrugs by antibody-enzyme conjugates.
Senter P. D., et al. *Cancer Res.* 49: 5789-92, 1989. Enhancement of the in vitro and in vivo antitumor activities of phosphorylated mitomycin C and etoposide derivatives by monoclonal antibody-alkaline phosphatase conjugates.
Senter P. D. *FASEB 1* 4: 188-93, 1990. Activation of prodrugs by antibody-enzyme conjugates: a new approach to cancer therapy.
Shan D., et al. *Clin. Cancer Res.* 7(8): 2490-95, 2001. Synergistic effects of the fenretinide (4-HPR) and anti-CD20 monoclonal antibodies on apoptosis induction of malignant human B cells.
Sharkey R. M., et al. *Cancer Res.* 50(3): 964s-969s, 1990. Biological considerations for radioimmunotherapy.
Shipp et al. *N Engl. I Med.* 329(14): 987-94, 1993. The International Non-Hodgkin's Lymphoma Prognostic Factors Project: A predictive model for aggressive non-Hodgkin's lymphoma.
Shipp, et al., "Section 3: Non-Hodgkin's Lymphomas," in Cancer: Principles & Practice of Oncology, Second Edition, eds. DeVita, Hellman, and Rosenberg, 1985, pp. 2165-2220.
Shipp, et al., "High Dose CHOP as Initial Therapy for Patients with Poor-Prognosis Aggressive Non-Hodgkin's Lymphoma: A Dose-Finding Pilot Study," Journal of Clinical Oncology 1995, vol. 13, No. 12, pp. 2916-2923.
Shulman M., et al. *Nature* 276(5685): 269-70, 1978. A better cell line for making hybridomas secreting specific antibodies.

(56) References Cited

OTHER PUBLICATIONS

Siddhartha, G. and Vijay, P., "R-CHOP versus R-CVP in the treatment of follicular lymphoma: a meta-analysis and critical appraisal of current literature". *J. Hematology & Oncology* 2:14, pp. 1-7 (Mar. 24, 2009) doi: 10.1186/1756-8722-2-14.
Skarin, et al., "Non-Hodgkin's Lymphomas: Current Classification and Management," CA Cancer J Clin 1997, 47:351-372.
Smalley R.V., et al. *N. Engl. I Med.* 327(19): 1336-41, 1992. Interferon alfa combined with cytotoxic chemotherapy for patients with non-Hodgkin's lymphoma.
Smeland E. B., et al. *I Immunol.* 138(10): 3179-84, 1987. Activation of human B cells: alternate options for initial triggering and effects of nonmitogenic concentrations of anti-IgM antibodies on resting and activated cells.
Smith, M. R., "Rituximab (monoclonal anti-CD20 antibody): mechanism of action and resistance," Oncogene 2003, vol. 22, No. 47, pp. 7359-7368.
Soiffer R.J., et al. *Blood* 79(2): 517-26, 1992. Clinical and immunologic effects of prolonged infusion of low-dose recombinant interleukin-2 after autologous and T-celldepleted allogeneic bone marrow transplantation.
Soiffer R.J., et al. *Blood* 84(3): 964-971, 1994. Effect of low-dose interleukin-2 on disease relapse after T-cell-depleted allogeneic bone marrow transplantation.
Solal-Celigny P., et al. *I Clin. Oncol.* 16(7): 2332-38, 1998. Doxorubicin-containing regimen with or without interferon alfa-2b for advanced follicular lymphomas: final analysis of survival and toxicity in the Groupe d'Etude des Lymphomes Folliculaires 86 Trial.
Sonneveld, et al., "Comparison of Doxorubicin and Mitoxantrone in the Treatment of Elderly Patients with Advanced Diffuse Non-Hodgkin's Lymphoma Using CHOP Versus CNOP Chemotherapy," Journal of Clinical Oncology, Oct. 1995, vol. 13, No. 10, pp. 2530-2539.
Sreerma, et al., "Cellular Levels of Class 1 and Class 3 Aldehyde Dehydrogenases and Certain Other Drug-metabolizing Enzymes in Human Breast Malignancies," Clinical Cancer Research, 1997, vol. 3, pp. 1901-1914.
Sriskandan, et al., "Aggressive management of doxorubicin-induced cardiomyopathy associated with 'low' doses of doxorubicin," Postgrad. Med. J. 1994, vol. 70, No. 828, pp. 759-761.
Srivastava S.C., et al. *Nucl. Med. Biol. (LI Rad. Appl. Instrum. B)* 18(6): 589-603, 1991. Progress in research on ligands, nuclides and techniques for labeling monoclonal antibodies.
Stashenko P., et al. *I Immunol.* 125(4): 1678-85, 1980. Characterization of Human B Lymphocyte-Specific Antigen.
Staudt L.M., et al. Manuscript from pubmedcentral at NIH, edited paper published at *Adv. Immunol.* 87: 163-208, 2005. The biology of human lymphoid malignancies revealed by gene expression profiling.
Stenbygaard L. E., et al. *Breast Cancer Res. Treatment* 25: 57-63, 1993. Toremifene and tamoxifen in advanced breast cancer—a double-blind cross-over trial.
Steward et al. "Maintenance Chlorambucil After CVP in the Management of Advanced Stage, Low-Grade Histologic Type Non-Hodgkin's Lymphoma" *Cancer* 61(3) 1988, pp. 441-447.
Stewart J. S. W., et al. *Int. J. Cancer* Suppl. 3: 71-76, 1988. Intraperitoneal $^{131}$I- and $^{9}$°Y-labelled monoclonal antibodies for ovarian cancer: pharmacokinetics and normal tissue dosimetry.
Sun L.K., et al. *Hybridoma* 5(Suppl. 1): S17-20, 1986. Chimeric antibodies with 17-1A-derived variable and human constant regions.
Sweetenham, et al., "Cost-minimization analysis of CHOP, fludarabine and rituximab for the treatment of relapsed indolent B-cell non-Hodgkin's lymphoma in the U.K.", *British Journal of Hematology* 106, 1999, pp. 47-54.
Swenson, et al., "Improved survival of follicular lymphoma patients in the United States," J. Clin Oncol, 2005, 23(22): 5019-5026.
Tan L. K., et al. *J. Immunol.* 135: 3564-67, 1985. A human-mouse chimeric immunoglobulin gene with a human variable region is expressed in mouse myeloma cells.

Tedder T. F., et al. *Eur J Immunol.* 16(8): 881-87, 1986. Antibodies reactive with the B1 molecule inhibit cell cycle progression but not activation of human B lymphocytes.
Tedder T. F., et al. *J Immunol.* 141(12): 4388-94, 1988. Cloning of a complementary DNA encoding a new mouse B lymphocyte differentiation antigen, homologous to the human B1 (CD20) antigen, and localization of the gene to chromosome 19.
Tedder T. F., et al. *J. Immunol.* 135(2): 973-79, 1985. The B cell surface molecule B1 is functionally linked with B cell activation and differentiation.
Tedder T. F., et al., "CD20: A regulator of cell-cycle progression of B lymphocytes." Immunol Today, 1994, vol. 15, pp. 450-454.
Teeling J. L., et al. *Blood* 104: 1793-1800, 2004. Characterization of new human CD20 monoclonal antibodies with potent cytolytic activity against non-Hodgkin lymphomas.
Teeling J. L., et al. *J Immunol.* 277: 362-71, 2006. The biological activity of human CD20 monoclonal antibodies is linked to unique epitopes on CD20.
Thomas, et al., "Clinical Development Success Rates 2006-2015," BIO Industry Analysis, Jun. 2016 (28 pages).
Thompson Reuters Pharma™ "Drug Report: Rituximab", 2011, pp. 1-4.
Title 21 Code of Federal Regulations, Subpart D, section 14.60-14.75, Apr. 1, 1997 ed., pp. 152-154.
Tobinai K., et al. *Ann. Oncol.* 9(5): 527-34, 1998. Feasibility and pharmacokinetic study of a chimeric anti-CD20 monoclonal antibody (IDEC-C2B8, rituximab) in relapsed B-cell lymphoma. The IDEC-C2B8 Study Group.
Treon, et al., "Interferon-Gamma Induces CD20 Expression on Multiple Myeloma Cells via Induction of Pu.1 and Augments Rituximab Binding to Myeloma Cells," Oncology 14(31): Abstract #521 (2000).
Tsai D. E., et al. *Blood* 92(10 Suppl. 1): 415a, abst. No. 1713, Nov. 1998. Progressive intermediate grade non-Hodgkin's lymphoma after high dose therapy and autologous peripheral stem cell transplantation (PSCT) has a high response rate to rituximab.
Tsai D. E., et al. *Bone Marrow Transplant.* 24(5): 521-26, 1999. Rituximab (anti-CD20 monoclonal antibody) therapy for progressive intermediate-grade non-Hodgkin's lymphoma after high-dose therapy and autologous peripheral stem cell transplantation.
Tsai D. E., et al. *Clin. Lymphoma Myeloma* 1(1): 62-66, 2000. Progressive intermediate-grade non-Hodgkin's lymphoma after high-dose therapy and autologous peripheral stem-cell transplantation: changing the natural history with monoclonal antibody therapy.
Uckun F. M., et al. *Cancer Res.* 45(1): 69-75, 1985. Increased efficiency in selective elimination of leukemia cells by a combination of a stable derivative of cyclophosphamide and a human B-cell-specific immunotoxin containing pokeweed antiviral protein.
Uckun F. M., et al., "Combined ex vivo treatment with immunotoxins and mafosfamid: a novel immunochemotherapeutic approach for elimination of neoplastic T cells from autologous marrow grafts", J Immunol., May 1985, vol. 134, No. 5, pp. 3504-3515.
United States Department of Health and Human Services, Food and Drug Administration, "Guidance for Industry: Distributing Scientific and Medical Publications on Unapproved New Uses—Recommended Practices", Revised Draft Guidance, Feb. 2014, pp. 1-17.
Unterhalt, et al., "Significant Prolongation of Disease Free Survival in Advanced Low Grade Non-Hodgkin's Lymphomas (NHL) by Interferon Alpha Maintenance: International Conference on Malignant Lymphoma, Jun. 5-8, 1996, Lugano, Switzerland", Annals of Oncology, 1996, vol. 7, Supplement 3, p. 229.
Unterhalt, et al., "Long Term Interferon Alpha Maintenance Prolongs Remission Duration in Advanced Low Grade Lymphomas and is Related to the Efficacy of Initial Cytoreductive Chemotherapy", Blood, Nov. 1996, vol. 88, No. 10, Suppl. 1, Abstract 1801, pp. 453a.
Urlaub G., et al. *Som. Cell. Mot Genet.* 12(6): 555-66, 1986. Effect of gamma rays at the dihydrofolate reductase locus: deletions and inversions.
US FDA Guidelines for "Clinical Pharmacology Section of Labeling for Human Prescription Drug and Biological Products—Content and Format," Dec. 2006 Labeling, pp. 1-19.

(56) References Cited

OTHER PUBLICATIONS

US FDA Regulations of 2006 (21 CFR Ch. I (Apr. 1, 2006 Edition)), pp. 8-90.
Valentine M.A., et al. *J. Biol. Chem.* 264: 11282-87, 1989. Phosphorylation of the CD20 phosphoprotein in resting B lymphocytes. Regulation by protein kinase C.
van der Kolk L. E., et al. *Blood* 92(10 Suppl. 1): 241b, abst. No. 4037, Nov. 1998. Chimeric anti-CD20 monoclonal antibody (rituximab) plus G-CSF in relapsed B-cell lymphoma: a phase I/II clinical trial.
van der Kolk L. E., et al. *Blood* 92(10 Suppl. 1): 512a-513a, abst. No. 2284, 1997. Phase I/II clinical trial to evaluate the safety and efficacy of a chimeric anti-CD20 monoclonal antibody (rituximab) and G-CSF given weekly to patients with relapsed B-cell lymphoma.
van der Kolk L. E., et al. *Br. I Haematol.* 102(1): 243, abst. No. P-0970, Jul. 1998. Chimeric anti-CD20 monoclonal antibody (rituximab) plus G-CSF in relapsed B-cell lymphoma: a phase I/II clinical trial.
Van Oers, et al., "Rituximab maintenance improves clinical outcome of relapsed/resistant follicular non-Hodgkin lymphoma in patients both with and without rituximab during induction: results of a prospective randomized phase 3 intergroup trial", Blood, 2006, vol. 108, pp. 3295-3301.
van Oers, "Rituximab maintenance therapy: a step forward in follicular lymphoma," Haematologica, 2007, 92:826-833.
van Oers, et al., "Chimeric anti-CD20 monoclonal antibody (Mabthera) in remission, induction and maintenance treatment of relapsed follicular non-Hodgkin's lymphoma: a phase III randomised clinical trial," Intergroup Collaborative Study (EORTC 20981), Aug. 17, 1998, pp. 1-68.
van Oers, et al., "Rituximab Maintenance Treatment of Relapsed/Resistant Follicular Non-Hodgkin's Lymphoma: Long-Term Outcome of the EORTC 20981 Phase III Randomized Intergroup Study," Journal of Clinical Oncology, 2010, vol. 28, No. 17, pp. 2853-2858.
Vartholomatos G., et al. *Acta Haematol.* 102: 94-98, 1999. Rituximab (anti-CD20 monoclonal antibody) administration in a young patient with resistant B-prolymphocytic leukemia.
Venkatesha, et al., "Sensitization of Pancreatic Cancer Stem Cells to Gemcitabine by Chk1 Inhibition," NeoPlasia, 2012, vol. 14, No. 6, pp. 519-525.
Venugopal P., et al. *Blood* 92(10 Suppl. 1): 247a, abst. No. 1009, Nov. 1998. Upregulation of CD20 expression in chronic lymphocytic leukemia (CLL) cells by in vitro exposure to cytokines.
Verkh L.I., et al. Proc. Amer. Soc. Clin. Oncol. 17: abst. No. 154, 1998. Dosimetry results of ONCOLYMTm in the treatment of refractory B cell non-Hodgkin's lymphoma (NHL).
Vey N., et al. *Leuk. Lymphoma* 221(1-2): 107-14, 1996. A pilot study of autologous bone marrow transplantation followed by recombinant interleukin-2 in malignant lymphomas.
Vose et. al., "Diagnosis and Treatment of Non-Hodgkin's Lymphoma of Adults", Neoplastic Diseases of the Blood, 3$^{rd}$ edition, Ch. 44, Wiernik, Canellos, Dutcher, & Kyle, Churchill Livingstone, 1996, pp. 907-924.
Vose J. M., et al. *J Clin. Oncol.* 19(2): 389-97, 2001. Phase II study of rituximab in combination with chop chemotherapy in patients with previously untreated, aggressive non-Hodgkin's lymphoma.
Vose, et al., "Long-te in update of a phase II study of rituximab in combination with previously untreated, aggressive non-Hodgkin's lymphoma," Leukemia & Lymphoma, Nov. 2005, vol. 46, No. 11, pp. 1569-1573.
Voso, et al., "In vivo depletion of B cells using a combination of high-dose cytosine arabinoside/mitoxantrone and rituximab for autografting in patients with non-Hodgkin's lymphoma," *Br. J Haematol* 109(4): 729-35 (2000).
Wadler S., et al. *Semin. Oncol.* 19(2 Suppl. 3): 45-48, 1992. Principles in the biomodulation of cytotoxic drugs by interferons.
Wadler, et al., "New Advances in Interferon Therapy of Cancer," The Oncologist 1997, 2:254-267.
Wahl R. L., et al. *J Nucl. Med.* 31(5): 852, abst. No. 622, 1990. Radioimmunotherapy of B-cell lymphoma with 1131 MB-1 monoclonal antibody.
Wahl R. L., et al. *Proc. Amer. Soc. Clin. Oncol.* 17: 40a, abst. No. 156, May 1998. Successful retreatment of non-Hodgkin's lymphoma (NHL) with iodine-131 anti-BI antibody.
Wang, et al., "The Synergistic in Vitro and in Vivo Antitumor Effect of Combination Therapy with Salinomycin and 5-Fluorouracil against Hepatocellular Carcinoma," PLOS One 2014, vol. 9, No. 5, pp. 1-10.
Weiner, "Rituximab: mechanism of action," Semin Hematol., 2010, 47(2), pp. 115-123.
Weisdorf, Daniel, et al., "Survival After Relapse of Low-Grade Non-Hodgkin's Lymphoma: Implications for Marrow Transplantation"; *J. Clin Oncol* 1992; 10(6): pp. 942-947.
Welte K., et al. *Blood* 64: 380-85, 1984. Defective interleukin 2 production in patients after bone marrow transplantation and in vitro restoration of defective T lymphocyte proliferation by highly purified interleukin 2.
Wessels B.W., et al. *Med. Phys.* 11(5): 638-45, 1984. Radionuclide selection and model absorbed dose calculations for radiolabeled tumor associated antibodies.
White, "Rituximab immunotherapy for non-Hodgkin's lymphoma," Cancer Biother Radiopharm, 1999, 14(4), pp. 241-250, with UCLA Medical Library stamped received date of Sep. 2, 1999. (13 pages).
White C. A., et al. *Ann. Oncol.* 10(3 Suppl): 64, abst. No. 215, 1999. Radioimmunotherapy of relapsed or refractory non-Hodgkin's lymphoma (NHL): IDEC-Y2B8 phase I/II $^{90}$yttrium trial.
White C. A., et al. *Ann. Rev. Med.* 52: 125-45, 2001. Antibody-targeted immunotherapy for treatment of malignancy.
White C. A., et al. *Blood* 87(9): 3640-49, 1996. Radioimmunotherapy of relapsed B-cell lymphoma with Yttrium 90 anti-idiotype monoclonal antibodies.
White C. A., et al. *Eur. J. Cancer* 35: S57, abst. No. 107, 1999. ZevalinTM radioimmunotherapy of relapsed or refractory non-Hodgkin's lymphoma.
White C. A., et al., "Anti-Cd20 Monoclonal Antibodies as Novel Treatments for Non-Hodgkin's Hodgkin's Lymphoma." Pharm. Sci. Tech. Today 2(3): 95-101 (Mar. 1999).
White C. A., et al., "Idec-C2b8-Induced B Cell Depletion is not Associated With Significant Immune Suppression or Infection." Eur. J. Cancer, Sep. 1997, vol. 33, Suppl. 8, Abstract 1203, p. 5266.
White, C. A., et al., "Anti-CD20 antibody (MAB) IDEC-C2B8 in relapsed low-grade/follicular (LG/F) B-cell non-Hodgkin's lymphoma (NHL). Expanded efficacy and safety results.", J Immunotherapy 19(6):458, Nov. 1996.
White, C. A., et al., "IDEC-C2B8: Improved tolerance correlated with pharmacodynamic effects in patients with B-cell NHL.", Proc Annu Meet Am Assoc Cancer Res 36:638 (#3799), Mar. 1995.
White, C. A., et al., "Review of single agent IDEC-C2B8 safety and efficacy results in low-grade or follicular non-Hodgkin's lymphoma.", Eur J Cancer, Jun. 1997, vol. 33, Suppl. 5, Abstract #91, p. S40.
White, Cancer Biother Radiophaim. Aug. 1999; 14(4): pp. 241-250, "Rituximab immunotherapy for non-Hodgkin's lymphoma."
White, et al., "Anti-Cd20 Monoclonal Antibodies As Novel Treatments for Non-Hodgkin's Lymphoma," Pharm. Sci. Tech. Today, Mar. 1999, vol. 2, No. 3, pp. 95-101.
Williams, et al., Chapter 2: Examination of the Blood in Williams Hematology, Fifth Edition, 8-15 (Beutler, et al., eds., 1995).
Winkler U., et al. *Blood* 92(10 Suppl. 1): 285b, abst. No. 4228, Nov. 1998. Severe side effects in patients with B-cell chronic lymphocytic leukemia (CLL) and lymphocytosis treated with the monoclonal anti-CD20 antibody rituximab.
Winkler U., et al. *Blood* 94: 2217-24, 1999. Cytokine-release syndrome in patients with B-cell chronic lymphocytic leukemia and high lymphocyte counts after treatment with an antiCD20 monoclonal antibody (rituximab, IDEC-C2B8).
Wiseman G., et al. *1.1 Rad. Oncol. Biol. Phys.* 45(10 Suppl): 390, abst. No. 260, 1999. Radioimmunotherapy of relapsed or refractory non-Hodgkin's Lymphoma (NHL) with IDEC-Y2B8.

(56) References Cited

OTHER PUBLICATIONS

Wiseman G., et al. *Blood* 92(10 Suppl. 1): 417a, abst. No. 1721, Nov. 1998. IDEC-Y2B8 radioimmunotherapy: baseline bone marrow involvement and platelet count are better predictors of hematologic toxicity than dosimetry.
Wiseman G., et al. Cancer Biother. Radiopharm. 13(1): 59, abst. No. 22, 1998. Radioimmunotherapy of relapsed non-Hodgkin's lymphoma (NHL) with IDEC-Y2B8 90yttrium anti-CD20 monoclonal antibody.
Wiseman G., et al. *Cancer Biother. Radiopharm.* 13(4): 317, abst. No. 51, 1998. IDECY2B8, radioimmunotherapy of relapsed non-Hodgkin's lymphoma (NHL): interim analysis.
Wiseman G., et al. *Cancer Biother. Radiopharm.* 14(4): 315, abst. No. 2, 1999. 90Yttrium labelled IDEC Y2B8 anti-CD20 radioimmunotherapy.
Wiseman G., et al. *Proc. Amer. Soc. Clin. Oncol.* 17, 1998. Radioimmunotherapy of relapsed non-Hodgkin's lymphoma (NHL) with IDEC-Y2B8 $^{90}$yttrium radioimmunotherapy.
Wiseman G. A., et al. *Blood* 92(10 Suppl. 1): 510a, abst. No. 2273, Nov. 1998. IDEC-Y2B8 ($^{90}$Y conjugated anti-CD20) dosimetry calculated from $^{111}$In anti-CD20 in patients with low and intermediate grade B-cell non-Hodgkin's lymphoma (NHL) emphasis on bone marrow (BM).
Wiseman G. A., et al. *Blood* 94(10 Suppl. 1): 92a, abst. No. 403, 1999. ZEVALIN$^M$ biodistribution and dosimetry estimated normal organ absorbed radiation doses are not affected by prior therapy with rituximab.
Wiseman G. A., et al. *Clin. Cancer Res.* 5(Suppl.): 3281s-3286s, 1999. Radioimmunotherapy of relapsed non-Hodgkin's lymphoma with Zevalin, a 90Y-labeled anti-CD20 monoclonal antibody.
Wiseman G. A., et al. *J NucL Med.* 39(5 Suppl.): 69P, abst. No. 267, 1998. Non-Hodgkin's lymphoma tumor and bone marrow radiation doses from radioimmunotherapy with IDECY2B8 yttrium-90 anti-CD20 monoclonal antibody.
Wiseman G. A., et al. *J NucL Med.* 40(1 Suppl.): 64P, abst. No. 260, 1999. Final dosimetry results of IDEC-Y2B8 phase I/II $^{90}$yttrium radioimmunotherapy trial in non-Hodgkin's lymphoma (NHL).
Wiseman G. A., et al. *I.J. Oncol. Biol. Phys.* 42(1 Suppl.): 130, abst. No. 11, 1998. IDECY2B8 ($^{90}$yttrium ibritumomab tiuxetan) radioimmunotherapy safety results in relapsed or chemotherapy refractory non-Hodgkin's lymphoma patients treated at reduced doses because of pre-existing thrombocytopenia.
Wiseman G. A., et al. I.J. Oncol. Biol. Phys. 45(3 Suppl.): 390, abst. No. 2217, 1999. IDECY2B8 (90yttrium(90yttriumibritumomab tiuxetan) radioimmunotherapy safety results in relapsed or chemotherapy refractory non-Hodgkin's lymphoma patients treated at reduced doses because of preexisting thrombocytopenia.
Wiseman G. A., et al. *J NucL Med.* 38(5 Suppl.): 251, abst. No. 1062, 1997. Y-90 anti-CD20 monoclonal antibody (IDEC-Y2B8) dosimetry calculated from In-111 anti-CD20 in patients with low and intermediate grade B-cell non-Hodgkin's lymphoma.
Wiseman G. A., et al. *J NucL Med.* 39(5 Suppl.): 185P, abst. No. 836, 1998. Whole-body gamma camera image quantification from multiple camera types for radioisotope therapy dosimetry.
Wiseman G. A., et al. *Proc. Amer. Soc. Clin. Oncol.* 18: 4a, abst. No. 13, 1999. Therapeutic index of IDEC-Y2B8 radioimmunotherapy: up to 850 fold greater radiation dose to tumor than normal organs.
Witherspoon R.P., et al. *Semin. Hematol.* 21(1): 2-10, 1984. Immunologic reconstitution after human marrow grafting.
Witzig T., et al. *Blood* 90(10 Suppl. 1): 586a, abst. No. 2606, 1997. IDEC-Y2B8 $^{90}$yttrium anti-CD20 radioimmunotherapy of relapsed non-Hodgkin's lymphoma (NHL): interim results of a phase I/II trial.
Witzig T., et al. *Blood* 92(10 Suppl. 1): 417a, abst. No. 1722, Nov. 1998. IDEC-Y2B8 radioimmunotherapy: responses in patients with splenomegaly.
Witzig T. E., et al. *Am. J. Clin. Pathol.* 101: 312-17, 1994. Measurement of the intensity of cell surface antigen expression in B-cell chronic lymphocytic leukemia.

Witzig T. E., et al. *Blood* 94(10 Suppl. 1): 631a, abst. No. 2805, 1999. Prospective randomized controlled study of ZEVALIN™ (IDEC-Y2B8) radioimmunotherapy compared to rituximab immunotherapy for B-cell NHL: report of interim results.
Witzig T. E., et al. *Blood* 94(10 Suppl. 1): 92a, abst. No. 400, 1999. Reduced-dose ZEVALIN™ radioimmunotherapy for relapsed or refractory B-cell non-Hodgkin's lymphoma (NHL) patients with pre-existing thrombocytopenia: report of interim results of a phase II trial.
Witzig T. E., et al. *J Clin. Oncol.* 17(12): 3793-3803, 1999. Phase I/II trial of IDEC-Y2B8 radioimmunotherapy for treatment of relapsed or refractory CD20(+) B-cell non-Hodgkin's lymphoma.
Witzig T. E., et al. *I Immunotherapy.* 21(6): 463, abst. No. 2805, 1998. IDEC-Y2B8 radioimmunotherapy of relapsed or refractory non-Hodgkin's lymphoma.
Witzig T. E., et al. *J. Clin. Oncol.* 20(15): 3262-69, 2002. Treatment with ibritumomab tiuxetan radioimmunotherapy in patients with rituximab-refractory follicular non-Hodgkin's lymphoma.
Witzig T. E., et al. *J. Clin. Oncol.* 20: 2453-63, 2002. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.
Witzig T. E., et al. *Proc. Amer. Soc. Clin. Oncol.* 18: 41a, abst. No. 152, 1999. Commonly used response criteria for non-Hodgkin's lymphoma (NHL) applied to IDEC-Y2B8 radioimmunotherapy trial: importance of "normal" lymph node size.
Yakoub-Agha, et al., "Allogeneic bone marrow transplantation in patients with follicular lymphoma: a single center study," *Bone Marrow Transplant* 30(4): 229-34 (2002).
Yang H., et al. *Am. J. Hematol.* 62: 247-50, 1999. Tumor lysis syndrome occurring after the administration of rituximab in lymphoproliferative disorders: high-grade non-Hodgkin's lymphoma and chronic lymphocytic leukemia.
Yokota S., et al. *Cancer Res.* 50: 32-37, 1990. Synergistic potentiation of in vivo antitumor activity of anti-human T-leukemia immunotoxins by recombinant a-interferon and daunorubicin.
Young, et al., "The treatment of indolent lymphomas: watchful waiting v aggressive combined modality treatment," Semin Hematol, 1988, 25 (2 Suppl 2): 11-16.
Zhou L-J, et al., "CD20 Workshop Panel Report" in Schlossman SF. Boumsell L., Gilks W., et al. (eds): *Leucocyte Typing V* (White Cell Differentiation Antigens. Proceedings of the Fifth International Workshop and Conference Held in Boston, USA Nov. 3-7, 1993) Oxford, United Kingdom, Oxford University, 1995, vol. 1, pp. 511-514.
Zhou X., et al. *Chinese Pharm. J.* 30(8): 453-54, 1995. (English translation of abstract provided.).
Zinzani, et al., "Elderly Aggressive-Histology Non-Hodgkin's Lymphoma: First-Line VNCOP-B Regimen Experience on 350 patients," Blood, Jul. 1999, Vo. 94, No. 1, pp. 33-38.
"What is a Stem Cell Transplant (Bone Marrow Transplant)?," Cancer.Net, Jan. 2016 (downloaded on Feb. 14, 2018), from https://www.cancer.net/navigating-cancer-care/howcancer-treated/bone-marrowstem-cell-transplantation/what-stem-cell-transplant-bone-marrow-transplant. (Feb. 14, 2018) (6 pages).
Affidavit of Christopher Butler with Exhibit A dated Sep. 28, 2016 (7 pages).
Al-Ismail et al., "Combination Chemotherapy Including Epirubicin for the Management of Non-Hodgkin's Lymphoma" Eur J Cancer Clin Oncol 23(9):1379-1384 (1987).
Armitage, J., "Treatment of Non-Hodgkin's Lymphoma" The New England Journal of Medicine 328(14):1023-1030 (1993).
Buske et al., "Monoclonal Antibody Therapy for B Cell Non-Hodgkin's Lymphomas: Emerging Concepts of a Tumour-targeted Strategy" European Journal of Cancer 35(4):549-557 (1999).
Curriculum Vitae of Brad S. Kahl, M.D. (Jan. 9, 2018) (30 pages).
Decision of Norwegian District Court dated Feb. 7, 2018 regarding Norwegian Patent No. 332893 (45 pages) with English translation thereof (43 pages).

(56) References Cited

OTHER PUBLICATIONS

Declaration of Brad S. Kahl, M.D., dated Feb. 26, 2018 (55 pages) in IPR2017-01168 re: U.S. Pat. No. 8,821,873 B2, White, et al., "Treatment of diffuse large-cell lymphoma with anti-CD20 antibody".
Declaration of David Gindler, dated Oct. 24, 2017 (5 pages) in IPR2017-01095 re: U.S. Pat. No. 9,296,821, Grillo-Lopez, "Combination therapies for B-cell lymphomas comprising administration of anti-CD20 antibodies".
Declaration of Megan Raymond, dated Feb. 7, 2018 (8 pages) in IPR2017-01095 re: U.S. Pat. No. 9,296,821, Grillo-Lopez, "Combination therapies for B-cell lymphomas comprising administration of anti-CD20 antibodies".
Declaration of Peter McLaughlin, M.D., dated Feb. 7, 2018 (104 pages) in IPR2017-01095 re: U.S. Pat. No. 9,296,821, Grillo-Lopez, "Combination therapies for B-cell lymphomas comprising administration of anti-CD20 antibodies".
Declaration of Sharon Song, dated Feb. 26, 2018 (3 pages) in IPR2017-01168 re: U.S. Pat. No. 8,821,873 B2, White et al., "Treatment of diffuse large-cell lymphoma with anti-CD20 antibody".
Declaration of Sharon Song, dated Jul. 10, 2017 (3 pages) in IPR2017-01095 re: U.S. Pat. No. 9,296,821, Grillo-Lopez, "Combination therapies for B-cell lymphomas comprising administration of anti-CD20 antibodies".
Deposition Transcript of Howard Ozer, M.D., Ph.D., (90 pages) in IPR2017-01168 re: U.S. Pat. No. 8,821,873 B2, White et al., "Treatment of diffuse large-cell lymphoma with anti-CD20 antibody" (Feb. 15, 2018).
Deposition Transcript of Petitioner's Expert Dr. Izidoie Lossos, (116 pages) IPR 2017-01095 re: U.S. Pat. No. 9,296,821, Grillo-Lopez, "Combination therapies for B-cell lymphomas comprising administration of anti-CD20 antibodies" (Jan. 25, 2018).
Eastern Cooperative Oncology Group (ECOG) Phase III Trial of Rituxan Maintenance Therapy in Indolent Non-Hodgkin's Lymphoma Reaches Pre-Specified Efficacy Endpoint Early (Nov. 2003) (p. 1).
Embace entry for White, C. "Rituximab Immunotherapy for Non-Hodgkin's Lymphoma" Cancer Biotherapy & Radiopharmaceuticals, 14(4): 241-250 (1999) (1 page).
EP 2990054A1 from Google Patents downloaded May 25, 2017, pp. 1-26.
Ezdinli et al., "Chlorambucil Therapy for Lymphomas and Chronic Lymphocytic Leukemia" Journal of American Medical Association 191(6):444-450 (1965).
Goss, P., "Non-Hodgkin's Lymphomas in Elderly Patients" Leukemia and Lymphoma 10:147-156 (1993).
Gribben et al., "Effectiveness of High-Dose Combination Chemotherapy and Autologous Bone Marrow Transplantation for Patients With Non-Hodgkin's Lymphomas Who Are Still Responsive to Conventional-Dose Therapy" Journal of Clinical Oncology, 7(11):1621-1629 (1989).
Grossbard et al. Malignant Lymphomas "18 Monoclonal Antibody Therapy of Lymphoma" BC Decker Inc., vol. 1:301-315 (2002).
Haioun et al., "Benefit of Autologous Bone Marrow Transplantation Over Sequential Chemotherapy in Poor-Risk Aggressive Non-Hodgkin's Lymphoma: Updated Results of the Prospective Study LNH87-2" Journal of Clinical Oncology 15(3):1131-1137 (1997).
Han et al., "Chlorambucil vs. Combined Chlorambucil-Corticosteroid Therapy in Chronic Lymphocytic Leukemia" Cancer 31(3):501-508 (1973).
Korsmeyer, S., "Bcl-2 Initiates a New Category of Oncogenes: Regulators of Cell Death" Blood 80(4):879-886 (1992).
McLaughlin et al., "CHOP-BLEO Plus α-Interferon (IFN) in Stage IV Low Grade Lymphoma (LGL)" American Society of Clinical Oncology (Abstract 1109), 11 (Mar. 1992) (1 page).
McLaughlin et al., "Stage III Follicular Lymphoma: Durable Remissions with a Combined Chemotherapy-Radiotherapy Regimen" Journal of Clinical Oncology 5(6):867-874 (1987).
Pamimolli et al., "The productivity crisis in pharmaceutical R&D" Nature 10:428-438 (2011).
Parlier et al., "Combination Chemotherapy with Cyclophosphamide Vincristine, Prednisone and the Contribution of Adriamycin in the Treatment of Adult Non-Hodgkin's Lymphomas A Report of 131 Cases" Cancer 50:401-409 (1982).
Patent Owner Response (POR) filed Feb. 26, 2018 by Biogen in IPR2017-01168 re: U.S. Pat. No. 8,821,873, White, et al., "Treatment of diffuse large-cell lymphoma with anti-CD20 antibody" (Feb. 26, 2018) (68 pages).
Patent Owner Response (POR) filed Feb. 7, 2018 by Biogen in IPR2017-01095 re: U.S. Pat. No. 9,296,821, Grillo-Lopez, "Combination therapies for B-cell lymphomas comprising administration of anti-CD20 antibodies" regarding U.S. Pat. No. 9,296,821 (Feb. 7, 2018) (83 pages).
Peterson et al., "Nodular Mixed Lymphoma (NML): A Composite Trial of Cyclophosphamide (CTX) and Cyclophosphamide, Adriamycin, Vincristine, Prednisone and Bleomycin (CAVPB)" Blood (abstract #749) 66(5 SUPPL1): 216a (Nov. 1985).
Phase II Pilot Study of Rituxan with Chemotherapy Showed 97% Response Rate in Type of Non-Hodgkin's Lymphoma, May 18, 1998, (downloaded on Apr. 3, 2018), https://www.gene.com/media/press-releases/4781/1998-05-18/phase-ii-pilot-study-of-rituxan-with-che (4 pages).
Philip et al., "High-Dose Therapy and Autologous Bone Marrow Transplantation After Failure of Conventional Chemotherapy in Adults With Intermediate-Grade or High-Grade Non-Hodgkin's Lymphoma" The New England Journal of Medicine 316(24):1493-1498 (1987).
Raphael et al., "Comparison of Chlorambucil and Prednisone Versus Cyclophosphamide, Vincristine, and Prednisone as Initial Treatment for Chronic Lymphocytic Leukemia: Long-Term Follow-Up of an Eastern Cooperative Oncology Group Randomized Clinical Trial" Journal of Clinical Oncology 9(5): 770-776 (1991).
Rigacci et al., "The Role of Anthracyclines in Combination Chemotherapy for the Treatment of Follicular Lymphoma: Retrospective Study of the Intergruppo Italiano Linfomi on 761 Cases" Leukemia & Lymphoma, 44(11):1911-1917 (2003).
Rituxan® (Rituximab) Prescribing Information dated Apr. 2016 (Apr. 2016), pp. 1-39.
Transcript of Recorded Testimony of Nancy Turman (via telephone), Oslo District Court, Oslo, Norway regarding Norwegian Patent No. 332893 (Dec. 12, 2017), pp. 1-13.
Transcript of Recorded Testimony of Prof. Marinus H. J. Van Oers, Oslo District Court, Oslo, Norway regarding Norwegian Patent No. 332893 (Dec. 14, 2017), pp. 1-44.
Transcript of Recorded Testimony of Professor Walter Longo, MD, Oslo District Court, Oslo, Norway regarding Norwegian Patent No. 332893 (Dec. 13, 2017), pp. 1-26.
Transcript of Recorded Testimony of Thomas Cerny, Oslo District Court, Oslo, Norway regarding Norwegian Patent No. 332893 (Dec. 14, 2017), pp. 1-37.
White, C. "Rituximab Immunotherapy for Non-Hodgkin's Lymphoma" Cancer Biotherapy & Radiopharmaceuticals, 14(4): 241-250 (1999) (NRCC date received: Aug. 23, 1999).
White, C. "Rituximab Immunotherapy for Non-Hodgkin's Lymphoma" Cancer Biotherapy & Radiopharmaceuticals, 14(4): 241-250 (1999) (University of Michigan date received: Aug. 24, 1999).
White, C. "Rituximab Immunotherapy for Non-Hodgkin's Lymphoma" Cancer Biotherapy & Radiopharmaceuticals, 14(4): 241-250 (1999) (University of Minnesota date received: Aug. 23, 1999).
White, C. "Rituximab Immunotherapy for Non-Hodgkin's Lymphoma" Cancer Biotherapy & Radiopharmaceuticals, 14(4): 241-250 (1999)—(Espacenet entry Feb. 24, 2017), p. 1.
DeVita et al., "Advanced Diffuse Histiocytic Lymphoma, A Potentially Curable Disease" The Lancet, pp. 248-250 (Feb. 1975).
Dillman, "Magic bullets at last! Finally—approval of a monoclonal antibody for the treatment of cancer!!!" Cancer Biotherapy Radiopharmaceuticals, 12(4): pp. 223-225 (1997).
Fisher et al., "Clinical Practical Guidelines: Non-Hodgkin's Lymphomas" Cleveland Clinic Journal of Medicine 62 (SUPPL 1): pp. 441-477 (1995).
Köhler and Milstein, Nature 256: pp. 495-497 (Aug. 7, 1975).

(56) References Cited

OTHER PUBLICATIONS

Piro et al., "Rituximab in Patients (pts) with Relapsed Low-Grade or Follicular Non-Hodgkin's Lymphoma (LG/F NHL): Response Rate and Duration with a Weekly Times 8 Dosing Regimen [abstract No. 49]" Proceedings of American Society of Clinical Oncology 18(14a) (1999).

* cited by examiner

TREATMENT OF DIFFUSE LARGE-CELL LYMPHOMA WITH ANTI-CD20 ANTIBODY

CROSS REFERENCE TO RELATED APPLICATIONS

This application is a continuation of U.S. application Ser. No. 15/334,234, filed Oct. 25, 2016, which is a continuation of U.S. application Ser. No. 14/310,167, filed Jun. 20, 2014, now U.S. Pat. No. 9,504,744, which is a continuation application of U.S. application Ser. No. 14/045,375 filed Oct. 3, 2013, now U.S. Pat. No. 8,821,873, which is a divisional of U.S. application Ser. No. 09/628,187 filed Jul. 28, 2000, now U.S. Pat. No. 8,557,244, which claims priority under 35 USC Section 119(e) and the benefit of U.S. Provisional Application Ser. No. 60/148,286 filed Aug. 11, 1999, the entire disclosures of which are incorporated herein by reference in their entireties.

FIELD OF THE INVENTION

The present invention concerns methods of treating intermediate- and high-grade non-Hodgkin's lymphomas, and lymphomas associated with a high level of bone marrow involvement with anti-CD20 monoclonal antibodies and fragments thereof.

BACKGROUND OF THE INVENTION

Non-Hodgkin's lymphoma is characterized by the malignant growth of B lymphocytes. According to the American Cancer Society, an estimated 54,000 new cases will be diagnosed, 65% of which will be classified as intermediate- or high-grade lymphoma. Patients diagnosed with intermediate-grade lymphoma have an average survival rate of 2-5 years, and patients diagnosed with high-grade lymphoma survive an average of 6 months to 2 years after diagnosis.

Intermediate- and high-grade lymphomas are much more aggressive at the time of diagnosis than are low-grade lymphomas, where patients may survive an average of 5-7 years with conventional therapies. Intermediate- and high-grade lymphomas are often characterized by large extranodal bulky tumors and a large number of circulating cancer cells, which often infiltrate the bone marrow of the patient.

Conventional therapies have included chemotherapy and radiation, possibly accompanied by either autologous or allogeneic bone marrow or stem cell transplantation if a suitable doner is available, and if the bone marrow contains too many tumor cells upon harvesting. While patients often respond to conventional therapies, they usually relapse within several months.

A relatively new approach to treating non-Hodgkin's lymphoma has been to treat patients with a monoclonal antibody directed to a protein on the surface of cancerous B cells. The antibody may be conjugated to a toxin or radiolabel thereby affecting cell death after binding. Alternatively, an antibody may be engineered with human constant regions such that human antibody effector mechanisms are generated upon antibody binding which result in apoptosis or death of the cell.

One antibody currently being investigated for the treatment of intermediate- and high-grade lymphomas is ONCOLYM® ($^{131}$I-Lym-1) (Techniclone Corp.), which is a murine IgG2a monoclonal antibody which recognizes the HLA-Drl 0 protein which is present on the surface of over 80% of lymphoma cells. Only 2% of normal B cells (noncancerous) express the HLA-Drl 0 molecule. ONCOLYM® IgG2a monoclonal antibody is conjugated to a Iodine-[131] ($^{131}$I), a radioactive isotope of iodine which emits beta irradiation for a distance of several millimeters, and is thereby thought to be an effective approach to targeting the outer rim of tumors and halting the progression of bulky disease However, a potential disadvantage in using ONCOLYM® IgG2a monoclonal antibody in advanced forms of non-Hodgkin's lymphoma is that such lymphomas are often characterized by bone marrow involvement. Thus, administration of a radiolabeled antibody to such patients often results in unwanted myelosuppression and damage to healthy progenitor cells.

It would be advantageous if alternative therapies and other monoclonal antibodies could be administered to patients with intermediate- and high-grade lymphomas which circumvent some of the deficiencies associated with current treatments and decrease the frequency of relapse.

SUMMARY OF THE INVENTION

The present invention concerns the use of anti-CD20 antibodies for the treatment of intermediate- and high-grade lymphomas, particularly those which are characterized by bone marrow involvement and bulky disease. In particular, the present inventors have surprisingly found that rituximab, a chimeric anti-CD20 antibody already approved for the treatment of low-grade follicular non-Hodgkin's lymphoma, may be effective to treat more aggressive lymphomas as well.

DETAILED DESCRIPTION OF THE INVENTION

The present invention relates to methods for treating or alleviating the symptoms of intermediate- or high-grade non-Hodgkin's lymphoma, or other lymphomas associated with a high degree of bone marrow involvement, comprising administering to a patient a therapeutically effective amount of an anti-CD20 antibody or other lymphoma cell depleting antibody, e.g. anti-CD19 and anti-CD22 antibodies, or a therapeutically effective fragment thereof. The present invention also includes administering anti-CD20 antibodies, or other lymphoma cell depleting antibodies, as part of a transplant regimen (autologous bone marrow transplant or allogeneic bone marrow transplant or peripheral blood stem cell transplant) to improve the survival of transplant recipients.

Therapeutically effective antibody "fragments" refers to any portion of or derivative of an antibody that is capable of delivering substantially the same therapeutic effect as the whole antibody when administered to a patient having intermediate- or high-grade non-Hodgkin's lymphoma (NHL), or when used as part of a transplant regimen.

As the understanding of lymphoma improves and new histopathologic variations are diagnosed, new classification systems for the different types of lymphoma have emerged. In general, for the purposes of the methods described herein, intermediate- and high-grade lymphomas are defined as those designated in the "Working Formulation" established in 1982. This system includes as intermediate-grade lymphomas follicular large cell (FL), diffuse small cleaved cell (DSC), diffuse mixed small and large cell (DM), and diffuse large cell, cleaved or noncleaved (DL). As high-grade lymphomas, the system recognizes immunoblastic large cell (IBL), lymphoblastic, convoluted or nonconvoluted (LL), and small noncleaved cell, Burkitt's or non-Burkitt's (SNC).

Several classification systems have emerged since the proposed Working Formulation. For instance, a recent-classification system proposed by European and American pathologists is called the Revised European American Lymphoma (REAL) Classification. Although this classification system does not use the terms "intermediate-" and "high-grade" NHL, it will be understood by those of skill in the art which lymphomas are typically characterized as "intermediate-" and "high-grade." For instance, "mantle cell lymphoma" as defined in the REAL classification system may appear as both indolent and more aggressive forms, and depending on the severity may be classified as an intermediate- or high-grade lymphoma.

For instance, the U.S. National Cancer Institute (NCI) has in turn divided some of the REAL classes into more clinically useful "indolent" or "aggressive" lymphoma designations. "Aggressive" lymphomas include diffuse mixed and large cell lymphoma, Burkitt's lymphoma/diffuse small noncleaved cell lymphoma, Lymphoblastic lymphoma, Mantle cell lymphoma and AIDS-related lymphoma. These lymphomas would therefor be considered at least "intermediate" or "high-grade," and would therefor benefit from the therapeutic methods of the present invention.

While strict classifications of some lymphomas may be difficult, the lymphomas treatable by the present invention are generally characterized by a high number of circulating B cells, possible bone marrow involvement, bulky disease, or the involvement of extralymphatic organ or sites.

Often, the patients which will most benefit from the disclosed therapeutic methods are those patients who are refractory to other types of treatments, or who have relapsed following other types of treatments, such as chemotherapy or radiotherapy. However, the monoclonal antibody treatments disclosed in the present invention will be beneficial also to newly diagnosed patients, and may have a synergistic effect in decreasing the chance of relapse if administered in conjunction with other conventional therapies.

For instance, the methods of the present invention include methods comprising the administration of both monoclonal antibodies (or fragments thereof) to CD20 along with a chemotherapeutic regimen. Depending on the particular patient, said chemotherapy may be administered simultaneously or sequentially in either order. "Simultaneously" means either concurrently or during the same time period such that the circulating half-lives of the therapeutic agents overlaps.

Chemotherapeutic regimens which may be combined with the antibody treatments of the present invention include CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP. The most preferred chemotherapeutic regimen is CHOP.

The primary anti-CD20 antibodies of the present invention are preferably human antibodies, or chimeric or humanized antibodies which are engineered with human constant region domains, such that the antibodies are able to stimulate human effector functions. A preferred antibody to be used in the methods of the present invention is RITUXAN® rituximab (IDEC Pharmaceuticals, Inc.).

Rituximab is one of a new generation of monoclonal antibodies developed to overcome limitations encountered with murine antibodies, including short half-life, limited ability to stimulate human effector functions, and immunogenicity. Rituximab is a genetically engineered monoclonal antibody with murine light- and heavy-chain variable regions and human gamma I heavy-chain and kappa light-chain constant regions. The chimeric antibody is composed of two heavy chains of 451 amino acids and two light chains of 213 amino acids and has an approximate molecular weight of 145 kD.

Rituximab is more effective than its murine parent in fixing complement and mediating ADCC, and it mediates CDC in the presence of human complement. The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner. In humans, the half-life of the antibody is approximately 60 hours after the first infusion and increases with each dose to 174 hours after the fourth infusion. The immunogenicity of the antibody is low; of 355 patients in seven clinical studies, only three (<1%) had a detectable anti-chimeric antibody (HACA) response.

The methods of the present invention may comprise administration of a radiolabeled antibody which binds to a protein on the surface of cancerous B cells. Such radiolabeled antibodies are preferably administered following administration of the human, chimeric or humanized antibody, which will decrease the amount of cancerous B cells in the bone marrow and lessen the likelihood of unwanted myeloablative suppression due to antibody binding to tumor cells in the marrow. Moreover, while CD20 is an ideal target for the immunotherapy of the present invention, it is possible that radiolabeled antibodies directed to other B cell surface antigens may also be used in the methods of the present invention. In particularly preferred embodiments, the radiolabeled antibodies are used in conjunction with unlabeled antibodies.

Approximately 80% of non-Hodgkin's lymphomas are B-cell-malignancies and >95% of these express the CD20 antigen on the cell surface. This antigen is an attractive target for immunotherapy because it is found exclusively on B cells, and not on hematopoietic stem cells, pro-B cells, normal plasma cells, or other normal tissues. It is not shed from the cell surface and does not modulate upon antibody binding.

The radiolabeled antibodies of the present invention may be labeled with any alpha or beta emitting radioisotope. However, a preferred isotope is $^{90}$Y, and a preferred antibody is Y2B8. Y2B8 was engineered from the same murine antibody, 2B8, as was rituximab. The 2B8 antibody has also been conjugated to different radiolabels for diagnostic and therapeutic purposes. To this end, copending application Ser. Nos. 08/475,813, 08/475,815 and 08/478,967, herein incorporated by reference in their entirety, disclose radiolabeled anti-CD20 conjugates for diagnostic "imaging" of B cell lymphoma tumors before administration of therapeutic antibody. For instance, the "In2B8" conjugate comprises the murine monoclonal antibody, 2B8, attached to Indium[111] ($^{111}$In) via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. Nos. 08/475,813, 08/475,815 and 08/478,967 was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in application Ser. Nos. 08/475,813, 08/475,815 and 08/478,967 are radiolabeled therapeutic antibodies for the targeting and destruction of B cell lymphomas and tumor cells. In particular, the Y2B8 conjugate comprises the same anti-human CD20 murine monoclonal antibody, 2B8, attached to yttrium-[90] ($^{90}$Y) via the same bifunctional chelator. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Because the $^{90}$Y radionuclide was attached to the 2B8 antibody using the same bifunctional chelator molecule MX-DTPA, the Y288 conjugate possesses the same advantages discussed above, e.g., increased retention of radionuclide at a target site (tumor). However, unlike $^{131}$In, it cannot be used for imaging purposes due to the lack of gamma radiation associated therewith. Thus, a diagnostic "imaging" radionuclide, such as $^{111}$In, can be used for determining the location and relative size of a tumor prior to and/or following administration of therapeutic chimeric or $^{90}$Y-labeled antibodies in the combined regimens of the invention. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}$I, $^{125}$I, $^{123}$I, $^{99}$Tc, $^{67}$Ga, as well as $^{111}$In. Antibodies have also been labeled with a variety of radionuclides for potential use in targeted immunotherapy (Peirersz et al., 1987). The use of monoclonal antibody conjugates for the diagnosis and treatment of cancer. Immunol. Cell Biol. 65: 111-125). These radionuclides include $^{188}$Re and $^{186}$Re as well as $^{90}$Y, and to a lesser extent $^{199}$Au and $^{67}$Cu. U.S. Pat. No. 5,460,785 provides a listing of such radioisotopes and is herein incorporated by reference.

As reported in copending application Ser. Nos. 08/475,813, 08/475,815 and 08/478,967 administration of the radiolabeled Y2B8 conjugate, as well as unlabeled chimeric anti-CD20 antibody (rituximab), resulted in significant tumor reduction in mice harboring a B cell lymphoblastic tumor. Moreover, human clinical trials reported therein showed significant B cell depletion in low-grade NHL lymphoma patients infused with rituximab. In fact, rituximab has recently been heralded the nation's first FDA-approved anti-cancer monoclonal antibody.

In addition, U.S. application Ser. No. 08/475,813, herein incorporated by reference, discloses sequential administration of RITUXAN® (rituximab), a chimeric anti-CD20, with both or either indium-labeled or yttrium-labeled murine monoclonal antibody for the treatment of low-grade NHL. Although the radiolabeled antibodies used in these combined therapies are murine antibodies, initial treatment with chimeric anti-CD20 sufficiently depletes the B cell population such that the HAMA response is decreased, thereby facilitating a combined therapeutic and diagnostic regimen. Moreover, it was shown in U.S. application Ser. No. 08/475,813 that a therapeutically effective dosage of the yttrium-labeled anti-CD20 antibody following administration of rituximab is sufficient to (a) clear any remaining peripheral blood B cells not cleared by the chimeric anti-CD20 antibody; (b) begin B cell depletion from lymph nodes; or (c) begin B cell depletion from other tissues.

Autologous bone marrow transplantation is often a successful accompaniment to myeloablative therapy in helping to restore the immune system to patients who have undergone radiotherapy or chemotherapy. However, as discussed above, the patients who will benefit by the methods disclosed herein will often have lymphoma accompanied by bone marrow involvement. For such patients, there are often too many cancerous cells in the marrow to perform autologous transplantation.

When there is bone marrow involvement accompanying the intermediate- or high-grade lymphoma, such patients may benefit by prior treatment with human, chimeric or humanized anti-CD20 antibody before bone marrow harvesting in order to decrease the quantity of tumor cells in the bone marrow or stem cell preparation. In fact, rituximab can be administered at induction, in vivo purging, mobilization, conditioning, post-transplant reinfusion and at any other time during bone marrow or stem cell transplant for the purpose of improving the survival rate of transplant recipients. "Induction" is meant to refer to the initial therapies aimed at achieving induction of remission. Typically, induction involves the administration of some type of chemotherapy, i.e., CHOP.

The phrase "in vivo purging" is meant to refer to treatment particularly geared toward purging tumor cells from the bone marrow within the patient, although certainly such treatment might be beneficial for tumor cells in the peripheral blood and at other sites as well. Such a step may precede the harvest of bone marrow as a means of decreasing the number of tumor cells therein. Rituximab and other chimeric lymphoma cell-depleting antibodies provide an advantage in this regard over radiolabeled antibodies in that they may be used to purge the bone marrow of cancerous cells without damaging healthy progenitors.

"Mobilization" refers to the process by which stem cells are mobilized to leave the bone marrow and enter the circulatory system, and provides an alternative to bone marrow harvest per se as a source of stem cells for transplantation. Mobilization is typically achieved by administering a short burst of chemotherapy and/or growth factors. The growth factor G-CSF is commonly used, but others may be used according to the knowledge of the skilled artisan.

Typically, during mobilization, stem cells are separated from blood (which is then put back into the patient), and the stem cells are frozen until the patient is ready to be reinfused. Ex vivo purging with rituximab, or other antibodies known in the art to be useful for this purpose, may then be used to deplete tumor cells in the stem cell preparation.

Conditioning" refers to a process by which the patient is prepared to receive the autologous bone marrow reinfusion or allogeneic transplant. This is typically accomplished with a very high dose of chemotherapy in order to deplete all bone marrow cells, i.e., both healthy cells and tumor cells, from the bone marrow. Chemotherapeutic drugs that may be given at sufficiently high doses without risking the patient's life, e.g. cyclophosphamide, are known in the art.

Thus, with rituximab treatment at the various stages of transplantation, marrow may be harvested prior to myeloablative radiotherapy, and reintroduced subsequent to such therapy with less concern about reintroducing tumor cells originally harvested with the marrow back into the patient. Of course, the patient may then benefit by additional or subsequent treatment with chimeric anti-CD20 antibody as part of a maintenance regimen, or by administration of a radiolabeled antibody such as Y2B8 to further decrease the chance of relapse.

The methods of the present invention also encompass combined therapy comprising administration of at least one cytokine along with an anti-CD20 antibody or fragment thereof. Such a cytokine may be administered simultaneously or sequentially in any order. In particular, cytokines may be useful in upregulating the expression of CD20 on the surface of cancerous B cells prior to administration of the anti-CD20 antibody. Cytokines useful for this purpose include IL-4, GM-CSF and TNF-alpha, and possibly others.

Cytokines may also be administered simultaneously or within the same time frame in order to increase or control certain effector functions mediated by the therapeutic antibody. Cytokines useful for this purpose include interferon alpha, G-CSF and GM-CSF, and possibly others.

Preferred dosage regimens and exemplary embodiments will now be illustrated by way of the following data.

Single-Agent Studies

In a study conducted in Europe and Australia, alternative dosing schedules were evaluated in 54 relapsed or refractory intermediate- or high-grade NHL patients (Coiffier B, Haioun C, Ketterer N, Engert A, Tilly H, Ma D, Johnson P, Lister A, Feuring-Buske M, Radford J A, Capdeville R, Diehl V, Reyes F. Rituximab (anti-CD20 monoclonal antibody) for the treatment of patients with relapsing or refractory aggressive lymphoma: a multicenter phase H study. *Blood* 1998; 92:1927-1932).

Rituximab was infused at 375 mg/m2 weekly for 8 doses or at 375 mg/m2 once followed by 500 mg/m2 weekly for 7 doses. The ORR was 31%; (CR 9%, PR 22%) no significant difference between the dosing regimens was observed. Patients with diffuse large-cell lymphoma (N=30) had an ORR of 37% and those with mantle-cell lymphoma (N=12) had an ORR of 33%.

Treatment of Bulky Disease

Contrary to early assumptions about antibody therapy being useful only in micrometastatic disease, rituximab is quite active in high bulk disease. In a separate study, 31 patients with relapsed or refractory, bulky low-grade NHL (single lesion of >10 cm in diameter) received 375 mg/m$^2$ rituximab as four weekly infusions. Twelve of 28 evaluable patients (43%) demonstrated a CR (1, 4%) or PR (11, 39%) (Davis T, White C, Grillo-Lopez A, Velasquez W, Link B, Maloney D, Dillman R, Williams M, Mohrbacher A, Weaver R, Dowden S, Levy R. Rituximab: First report of a Phase II (PII) trial in NHL patients (pts) with bulky disease. *Blood* 1998; 92 (10 Suppl 1):414a).

This suggests that with the appropriate dosages depending on the extent of disease and the number of circulating tumor cells (i.e., such as the increased dosages described above), rituximab therapy will also be useful for more aggressive intermediate- or high-grade NHLs accompanied by bulky disease.

Combination of Rituximab and CHOP Chemotherapy

In another study, 31 patients with intermediate- or high-grade NHL (19 females, 12 males, median age 49) received rituximab on Day 1 of each of six 21-day cycles of CHOP: Link B, Grossbard M, Fisher R, Czuczman M, Gilman P, Lowe A, Vose J. Phase II pilot study of the safety and efficacy of rituximab in combination with CHOP chemotherapy in patients with previously untreated- or high-grade NHL. *Proceedings of the American Society of Clinical Oncology* 1998; 17:3a). Of 30 evaluable patients, there were 19 CR (63%) and 10 PR (33%), for an ORR of 96%. This regimen was considered well tolerated and may result in higher response rates than with rituximab or CHOP alone.

The NCI Division of Cancer Treatment and Diagnosis is collaborating with IDEC Pharmaceuticals Corporation to explore rituximab treatment in other indications. A Phase II trial of CHOP versus CHOP and rituximab is being conducted by ECOG, CALGB, and SWOG in older patients (>60 years) with mixed, diffuse large cell, and immunoblastic large cell histology NHL (N=630 planned). This study includes a secondary randomization to maintenance with rituximab versus nonmaintenance.

A Phase III trial of rituximab and CHOP in 40 patients with previously untreated mantle-cell lymphoma is also ongoing at the Dana Farber Institute. Rituximab is administered on Day 1 and CHOP is given on Days 1-3 every 21 days for 6 cycles. Accrual for this study has been completed. A Phase II trial of CHOP followed by rituximab in newly diagnosed follicular lymphoma conducted by SWOG has also been completed. Results of these two trials are being analyzed.

A Phase II trial of CHOP and rituximab versus CHOP alone in HIV-related NHL conducted by the AIDS Malignancy Consortium is ongoing; 120 patients are planned.

Rituximab after Myeloablative Therapy Relapse

Rituximab has shown promising early results in patients with relapsed intermediate-grade NHL after high-dose therapy with autologous PBSC support. Six of seven patients responded (1 CR and 5 PR) and one patient had stable disease; therapy was well tolerated (Tsai, D, Moore H, Porter D, Vaughn D, Luger S, Loh R, Schuster S, Stadtmauer E. Progressive intermediate grade non-Hodgkin's lymphoma after high dose therapy and autologous peripheral stem cell transplantation (PSCT) has a high response rate to rituximab. *Blood* 1998; 92:415a, #1713).

The invention claimed is:

1. A method of treating a human patient with diffuse large cell lymphoma comprising administering rituximab and CHOP (cyclophosphamide, hydroxydaunorubicin/doxorubicin, vincristine, and prednisone/prednisolone) to the patient, wherein the rituximab is administered on Day 1 of each chemotherapy cycle and the CHOP is administered on Day 1 of each chemotherapy cycle, wherein the patient is >60 years old and has bulky disease (tumor>10 cm in diameter).

* * * * *